US008979928B2

(12) United States Patent
Donner

(10) Patent No.: US 8,979,928 B2
(45) Date of Patent: Mar. 17, 2015

(54) SACROILIAC JOINT FIXATION FUSION SYSTEM

(75) Inventor: Edward Jeffrey Donner, Fort Collins, CO (US)

(73) Assignee: JCBD, LLC, Fort Collins, CO (US)

( * ) Notice: Subject to any disclaimer, the term of this patent is extended or adjusted under 35 U.S.C. 154(b) by 0 days.

(21) Appl. No.: 12/998,712

(22) PCT Filed: Jan. 13, 2011

(86) PCT No.: PCT/US2011/000070
§ 371 (c)(1),
(2), (4) Date: May 23, 2011

(87) PCT Pub. No.: WO2011/087912
PCT Pub. Date: Jul. 21, 2011

(65) Prior Publication Data
US 2013/0035723 A1 Feb. 7, 2013

Related U.S. Application Data

(60) Provisional application No. 61/335,947, filed on Jan. 13, 2010.

(51) Int. Cl.
*A61F 2/44* (2006.01)
*A61F 2/30* (2006.01)
(Continued)

(52) U.S. Cl.
CPC .......... *A61F 2/30988* (2013.01); *A61B 17/025* (2013.01); *A61B 17/7043* (2013.01); *A61F 2002/30622* (2013.01); *A61F 2002/30995* (2013.01); *A61B 17/1739* (2013.01); *A61B 17/7055* (2013.01); *A61B 17/1757* (2013.01); *A61B 17/8645* (2013.01)
USPC ...................................... 623/17.11

(58) Field of Classification Search
CPC ......... A61B 17/70; A61F 2/44; A61F 2/4405; A61F 2/4455–2/447
USPC .................. 606/246–321; 623/17.11–17.16; 411/452, 451.4, 487
See application file for complete search history.

(56) References Cited

U.S. PATENT DOCUMENTS 4,488,542 A 12/1984 Helland
4,569,338 A 2/1986 Edwards
(Continued)

FOREIGN PATENT DOCUMENTS

AU 1753200 8/2000
CN 2265765 Y 10/1997
(Continued)

OTHER PUBLICATIONS

International Search Report and Written Opinion, PCT Application No. PCT/US2011/000070, dated Mar. 21, 2011, 13 pages.
(Continued)

*Primary Examiner* — Mary Hoffman
*Assistant Examiner* — Michelle C Eckman
(74) *Attorney, Agent, or Firm* — Polsinelli PC; Samuel Wade Johnson; Joshua J. Pranckun

(57) ABSTRACT

A sacroiliac joint fixation fusion system that provides a method of fixation and fusion of the sacroiliac joint and a sacroiliac joint implant which upon placement within the articular region of the sacroiliac joint facilitates stability and fusion of the sacroiliac joint.

37 Claims, 29 Drawing Sheets

(51) Int. Cl.
*A61B 17/02* (2006.01)
*A61B 17/70* (2006.01)
*A61B 17/17* (2006.01)
*A61B 17/86* (2006.01)

(56) References Cited

U.S. PATENT DOCUMENTS

| | | | |
|---|---|---|---|
| 4,590,928 A | 5/1986 | Hunt et al. | |
| 4,622,959 A | 11/1986 | Marcus | |
| 4,714,469 A | 12/1987 | Kenna | |
| 4,773,402 A | 9/1988 | Asher et al. | |
| 4,794,918 A | 1/1989 | Wolter | |
| 4,881,535 A | 11/1989 | Sohngen | |
| 4,911,153 A | 3/1990 | Border | |
| 4,920,958 A | 5/1990 | Walt et al. | |
| 4,950,270 A | 8/1990 | Bowman et al. | |
| 5,026,373 A | 6/1991 | Ray et al. | |
| 5,052,375 A | 10/1991 | Stark et al. | |
| 5,112,337 A | 5/1992 | Paulos et al. | |
| 5,176,681 A | 1/1993 | Lawes et al. | |
| 5,192,327 A | 3/1993 | Brantigan | |
| 5,242,444 A | 9/1993 | MacMillan | |
| 5,282,861 A | 2/1994 | Kaplan | |
| 5,334,192 A | 8/1994 | Behrens | |
| 5,334,205 A | 8/1994 | Cain | |
| 5,336,225 A | 8/1994 | Zang | |
| 5,368,546 A | 11/1994 | Stark et al. | |
| 5,368,593 A | 11/1994 | Stark | |
| 5,437,674 A | 8/1995 | Worcel et al. | |
| 5,443,509 A | 8/1995 | Boucher et al. | |
| 5,456,267 A | 10/1995 | Stark | |
| 5,480,402 A | 1/1996 | Kim | |
| 5,484,389 A | 1/1996 | Stark et al. | |
| 5,593,407 A | 1/1997 | Reis | |
| 5,607,424 A | 3/1997 | Tropiano | |
| 5,609,635 A | 3/1997 | Michelson | |
| 5,609,636 A * | 3/1997 | Kohrs et al. | 623/17.16 |
| 5,626,434 A | 5/1997 | Cook | |
| 5,658,337 A | 8/1997 | Kohrs et al. | |
| 5,669,909 A | 9/1997 | Zdeblick et al. | |
| 5,688,284 A | 11/1997 | Chervitz et al. | |
| 5,743,914 A | 4/1998 | Skiba | |
| 5,772,594 A | 6/1998 | Barrick | |
| 5,823,975 A | 10/1998 | Stark et al. | |
| 5,888,224 A | 3/1999 | Beckers et al. | |
| 5,891,150 A | 4/1999 | Chan | |
| 5,919,193 A | 7/1999 | Slavitt | |
| 5,928,239 A | 7/1999 | Mirza | |
| 5,929,782 A | 7/1999 | Stark et al. | |
| 5,993,463 A | 11/1999 | Truwit | |
| 6,045,552 A | 4/2000 | Zucherman et al. | |
| 6,053,916 A | 4/2000 | Moore | |
| 6,056,749 A | 5/2000 | Kuslich | |
| 6,063,442 A | 5/2000 | Cohen et al. | |
| 6,175,758 B1 | 1/2001 | Kambin | |
| 6,184,797 B1 | 2/2001 | Stark et al. | |
| 6,236,891 B1 | 5/2001 | Ingle et al. | |
| 6,241,771 B1 * | 6/2001 | Gresser et al. | 623/17.16 |
| 6,296,595 B1 | 10/2001 | Stark et al. | |
| 6,302,885 B1 * | 10/2001 | Essiger | 606/329 |
| 6,322,562 B1 | 11/2001 | Wolter | |
| 6,371,123 B1 | 4/2002 | Stark et al. | |
| 6,413,278 B1 | 7/2002 | Marchosky | |
| 6,432,107 B1 * | 8/2002 | Ferree | 606/247 |
| 6,432,140 B1 | 8/2002 | Lin | |
| 6,515,593 B1 | 2/2003 | Stark et al. | |
| 6,540,707 B1 | 4/2003 | Stark et al. | |
| 6,547,795 B2 | 4/2003 | Schneiderman | |
| 6,547,823 B2 * | 4/2003 | Scarborough et al. | 623/17.16 |
| 6,565,605 B2 | 5/2003 | Goble et al. | |
| 6,579,318 B2 | 6/2003 | Varga et al. | |
| 6,607,487 B2 | 8/2003 | Chang et al. | |
| 6,635,059 B2 | 10/2003 | Randall et al. | |
| 6,663,669 B1 | 12/2003 | Reiley | |
| 6,669,698 B1 | 12/2003 | Tromanhauser et al. | |
| 6,682,563 B2 | 1/2004 | Scharf | |
| 6,682,567 B1 | 1/2004 | Schroeder | |
| 6,716,245 B2 | 4/2004 | Pasquet et al. | |
| 6,723,099 B1 * | 4/2004 | Goshert | 606/329 |
| 6,743,256 B2 | 6/2004 | Mason | |
| 6,746,451 B2 | 6/2004 | Middleton et al. | |
| 6,824,564 B2 | 11/2004 | Crozet | |
| 6,827,670 B1 | 12/2004 | Stark et al. | |
| 6,835,208 B2 | 12/2004 | Marchosky | |
| 6,855,167 B2 | 2/2005 | Shimp et al. | |
| 6,860,902 B2 | 3/2005 | Reiley | |
| 6,872,187 B1 | 3/2005 | Stark et al. | |
| 6,875,236 B2 | 4/2005 | Reiley | |
| 6,902,567 B2 | 6/2005 | Del Medico | |
| 6,908,465 B2 | 6/2005 | von Hoffmann et al. | |
| 6,945,448 B2 | 9/2005 | Medlin et al. | |
| 6,972,019 B2 | 12/2005 | Michelson | |
| 6,974,461 B1 | 12/2005 | Wolter | |
| 7,011,660 B2 | 3/2006 | Sherman et al. | |
| 7,087,056 B2 | 8/2006 | Vaughan | |
| 7,087,058 B2 | 8/2006 | Cragg | |
| 7,108,828 B2 | 9/2006 | Lefebvre et al. | |
| 7,144,399 B2 | 12/2006 | Hayes et al. | |
| 7,192,447 B2 | 3/2007 | Rhoda | |
| 7,208,222 B2 | 4/2007 | Rolfe et al. | |
| 7,217,291 B2 | 5/2007 | Zucherman et al. | |
| 7,229,448 B2 | 6/2007 | Goble et al. | |
| 7,235,101 B2 | 6/2007 | Berry et al. | |
| 7,235,105 B2 * | 6/2007 | Jackson | 623/17.16 |
| 7,247,157 B2 | 7/2007 | Prager et al. | |
| 7,255,712 B1 | 8/2007 | Steinberg | |
| 7,331,995 B2 | 2/2008 | Eisermann et al. | |
| 7,396,360 B2 | 7/2008 | Lieberman | |
| 7,410,501 B2 | 8/2008 | Michelson | |
| 7,416,537 B1 | 8/2008 | Stark et al. | |
| 7,458,991 B2 | 12/2008 | Wang et al. | |
| 7,465,317 B2 | 12/2008 | Malberg et al. | |
| 7,520,898 B2 | 4/2009 | Re et al. | |
| 7,575,600 B2 | 8/2009 | Zucherman et al. | |
| 7,621,939 B2 | 11/2009 | Zucherman et al. | |
| 7,635,447 B2 | 12/2009 | Hamman et al. | |
| 7,637,954 B2 | 12/2009 | Michelson | |
| 7,641,697 B2 | 1/2010 | Reiley | |
| 7,648,509 B2 | 1/2010 | Stark | |
| 7,666,209 B2 | 2/2010 | Zucherman et al. | |
| 7,670,383 B1 | 3/2010 | Brown et al. | |
| 7,713,290 B2 | 5/2010 | Vaughan | |
| 7,740,795 B2 | 6/2010 | Wang et al. | |
| 7,771,441 B2 | 8/2010 | Cerundolo | |
| 7,794,465 B2 | 9/2010 | Marik et al. | |
| 7,819,869 B2 | 10/2010 | Godara et al. | |
| 7,824,404 B2 | 11/2010 | Godara et al. | |
| 7,837,732 B2 | 11/2010 | Zucherman et al. | |
| 7,846,162 B2 | 12/2010 | Nelson et al. | |
| 7,850,690 B2 | 12/2010 | Frigg et al. | |
| 7,909,871 B2 | 3/2011 | Abdou | |
| 7,918,891 B1 | 4/2011 | Curran et al. | |
| 7,922,765 B2 | 4/2011 | Reiley | |
| 7,963,970 B2 | 6/2011 | Marino et al. | |
| 7,972,363 B2 | 7/2011 | Moskowitz et al. | |
| 8,034,114 B2 | 10/2011 | Reiley | |
| 8,034,115 B2 | 10/2011 | Reiley | |
| 8,048,164 B2 | 11/2011 | Reiley | |
| 8,070,782 B2 | 12/2011 | Mckay | |
| 8,075,561 B2 | 12/2011 | Wolter | |
| 8,083,796 B1 * | 12/2011 | Raiszadeh et al. | 623/17.11 |
| 8,128,666 B2 | 3/2012 | Falahee | |
| 8,162,981 B2 | 4/2012 | Vestgaarden | |
| 8,202,305 B2 | 6/2012 | Reiley | |
| 8,231,661 B2 | 7/2012 | Carls et al. | |
| 8,308,779 B2 | 11/2012 | Reiley | |
| 8,308,794 B2 | 11/2012 | Martinson et al. | |
| 8,317,862 B2 | 11/2012 | Troger et al. | |
| 8,343,219 B2 | 1/2013 | Allain et al. | |
| 8,388,667 B2 | 3/2013 | Reiley | |
| 8,414,648 B2 | 4/2013 | Reiley | |
| 8,425,570 B2 | 4/2013 | Reiley | |
| 8,425,603 B2 | 4/2013 | Reichen et al. | |
| 8,444,693 B2 | 5/2013 | Reiley | |

(56) References Cited

U.S. PATENT DOCUMENTS

| | | |
|---|---|---|
| 8,470,004 B2 | 6/2013 | Reiley |
| 8,480,755 B2 | 7/2013 | Reiley |
| 8,491,572 B2 | 7/2013 | Martinson et al. |
| 8,496,712 B2 | 7/2013 | Reiley |
| 8,501,690 B2 | 8/2013 | Stark |
| 8,585,744 B2 | 11/2013 | Duggal et al. |
| 8,808,305 B2 | 8/2014 | Kleiner |
| 8,808,336 B2 | 8/2014 | Duggal et al. |
| 8,808,377 B2 | 8/2014 | Donner |
| 8,808,380 B2 | 8/2014 | Fox et al. |
| 8,808,389 B2 | 8/2014 | Reiley |
| 8,821,546 B2 | 9/2014 | Vaughan |
| 8,840,651 B2 | 9/2014 | Reiley |
| 2001/0005796 A1 | 6/2001 | Zdeblick et al. |
| 2001/0011191 A1* | 8/2001 | Kohrs ................ 623/17.16 |
| 2001/0016775 A1* | 8/2001 | Scarborough et al. ..... 623/17.16 |
| 2001/0018616 A1 | 8/2001 | Schwab |
| 2001/0020143 A1 | 9/2001 | Stark et al. |
| 2002/0029784 A1 | 3/2002 | Stark et al. |
| 2002/0032484 A1 | 3/2002 | Hyde, Jr. |
| 2002/0082701 A1 | 6/2002 | Zdeblick et al. |
| 2002/0087161 A1 | 7/2002 | Randall et al. |
| 2002/0147461 A1 | 10/2002 | Aldrich et al. |
| 2002/0147496 A1 | 10/2002 | Belef et al. |
| 2002/0183846 A1 | 12/2002 | Kuslich et al. |
| 2003/0044301 A1 | 3/2003 | Lefebvre et al. |
| 2003/0114931 A1 | 6/2003 | Lee et al. |
| 2003/0124486 A1 | 7/2003 | McDevitt |
| 2003/0181981 A1 | 9/2003 | Lemaire |
| 2003/0208202 A1 | 11/2003 | Falahee |
| 2004/0073216 A1 | 4/2004 | Lieberman |
| 2004/0127988 A1 | 7/2004 | Goble et al. |
| 2004/0186482 A1 | 9/2004 | Kolb et al. |
| 2004/0186578 A1* | 9/2004 | Mason ................ 623/17.16 |
| 2004/0199256 A1* | 10/2004 | Wang ................ 623/17.12 |
| 2004/0220668 A1 | 11/2004 | Eisermann et al. |
| 2004/0228901 A1 | 11/2004 | Trieu |
| 2004/0230305 A1* | 11/2004 | Gorensek et al. .......... 623/17.11 |
| 2004/0249675 A1 | 12/2004 | Stark et al. |
| 2005/0043660 A1 | 2/2005 | Stark et al. |
| 2005/0101887 A1 | 5/2005 | Stark et al. |
| 2005/0113652 A1 | 5/2005 | Stark et al. |
| 2005/0131539 A1* | 6/2005 | Kohrs ................ 623/17.11 |
| 2005/0149192 A1* | 7/2005 | Zucherman et al. ........ 623/17.11 |
| 2005/0149193 A1* | 7/2005 | Zucherman et al. ........ 623/17.11 |
| 2005/0154391 A1 | 7/2005 | Doherty et al. |
| 2005/0203515 A1 | 9/2005 | Doherty et al. |
| 2005/0216088 A1* | 9/2005 | McKinley et al. ......... 623/17.16 |
| 2005/0240264 A1 | 10/2005 | Tokish, Jr. et al. |
| 2005/0245925 A1 | 11/2005 | Iki et al. |
| 2005/0267482 A1 | 12/2005 | Hyde, Jr. |
| 2005/0273099 A1 | 12/2005 | Baccelli et al. |
| 2006/0052787 A1* | 3/2006 | Re et al. .................. 606/72 |
| 2006/0054171 A1 | 3/2006 | Dall |
| 2006/0058876 A1 | 3/2006 | McKinley |
| 2006/0069438 A1 | 3/2006 | Zucherman et al. |
| 2006/0069439 A1 | 3/2006 | Zucherman et al. |
| 2006/0085068 A1* | 4/2006 | Barry ................ 623/17.11 |
| 2006/0089716 A1* | 4/2006 | Felix ................ 623/17.11 |
| 2006/0095134 A1 | 5/2006 | Trieu et al. |
| 2006/0106382 A1 | 5/2006 | Gourmay et al. |
| 2006/0147332 A1 | 7/2006 | Jones et al. |
| 2006/0161154 A1 | 7/2006 | McAfee |
| 2006/0167547 A1* | 7/2006 | Suddaby ................ 623/17.11 |
| 2006/0241621 A1 | 10/2006 | Moskowitz et al. |
| 2007/0027543 A1 | 2/2007 | Gimble et al. |
| 2007/0055316 A1 | 3/2007 | Godara et al. |
| 2007/0055374 A1 | 3/2007 | Copf, Jr. et al. |
| 2007/0155588 A1 | 7/2007 | Stark et al. |
| 2007/0156241 A1* | 7/2007 | Reiley et al. ............ 623/17.11 |
| 2007/0162134 A1 | 7/2007 | Marnay et al. |
| 2007/0179621 A1 | 8/2007 | McClellan, III et al. |
| 2007/0191955 A1 | 8/2007 | Zucherman et al. |
| 2007/0198093 A1 | 8/2007 | Brodke et al. |
| 2007/0239164 A1 | 10/2007 | Prager et al. |
| 2007/0265621 A1 | 11/2007 | Matthis et al. |
| 2007/0270879 A1 | 11/2007 | Isaza et al. |
| 2007/0293949 A1 | 12/2007 | Salerni et al. |
| 2007/0299525 A1* | 12/2007 | Binotto ................ 623/17.16 |
| 2008/0009861 A1 | 1/2008 | Stark |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0039843 A1 | 2/2008 | Abdou |
| 2008/0065215 A1 | 3/2008 | Reiley |
| 2008/0140082 A1 | 6/2008 | Erdem et al. |
| 2008/0140200 A1 | 6/2008 | Heinz |
| 2008/0154305 A1 | 6/2008 | Foley et al. |
| 2008/0154306 A1 | 6/2008 | Heinz |
| 2008/0154377 A1 | 6/2008 | Voellmicke |
| 2008/0183293 A1 | 7/2008 | Parry et al. |
| 2008/0228276 A1 | 9/2008 | Mathews et al. |
| 2008/0262621 A1* | 10/2008 | Gorek ................ 623/17.16 |
| 2008/0288081 A1 | 11/2008 | Scrafton et al. |
| 2008/0300685 A1 | 12/2008 | Carls et al. |
| 2009/0018660 A1 | 1/2009 | Roush |
| 2009/0024174 A1* | 1/2009 | Stark ................ 606/321 |
| 2009/0036927 A1* | 2/2009 | Vestgaarden ................ 606/247 |
| 2009/0043394 A1 | 2/2009 | Zdeblick et al. |
| 2009/0076553 A1 | 3/2009 | Wolter |
| 2009/0088849 A1 | 4/2009 | Armstrong et al. |
| 2009/0099610 A1 | 4/2009 | Johnson et al. |
| 2009/0105833 A1 | 4/2009 | Hovda et al. |
| 2009/0105834 A1 | 4/2009 | Hovda et al. |
| 2009/0131986 A1* | 5/2009 | Lee et al. ............ 606/247 |
| 2009/0132035 A1 | 5/2009 | Roth et al. |
| 2009/0138053 A1 | 5/2009 | Assell et al. |
| 2009/0149957 A1 | 6/2009 | Burd et al. |
| 2009/0192621 A1 | 7/2009 | Winslow et al. |
| 2009/0216238 A1 | 8/2009 | Stark |
| 2009/0216276 A1 | 8/2009 | Pasquet |
| 2009/0248163 A1 | 10/2009 | King et al. |
| 2009/0259261 A1 | 10/2009 | Reiley |
| 2009/0259316 A1 | 10/2009 | Ginn et al. |
| 2009/0287254 A1 | 11/2009 | Nayet et al. |
| 2009/0306671 A1 | 12/2009 | McCormack et al. |
| 2010/0010496 A1 | 1/2010 | Isaza et al. |
| 2010/0094290 A1 | 4/2010 | Vaidya |
| 2010/0100135 A1 | 4/2010 | Phan |
| 2010/0106200 A1 | 4/2010 | Stark |
| 2010/0121160 A1 | 5/2010 | Stark et al. |
| 2010/0131011 A1 | 5/2010 | Stark |
| 2010/0137910 A1* | 6/2010 | Cawley et al. ................. 606/247 |
| 2010/0137919 A1 | 6/2010 | Wolter |
| 2010/0152785 A1 | 6/2010 | Forton et al. |
| 2010/0179552 A1 | 7/2010 | Wolter |
| 2010/0268228 A1 | 10/2010 | Petersen |
| 2010/0286785 A1* | 11/2010 | Grayson ................ 623/17.16 |
| 2010/0292800 A1 | 11/2010 | Zubok |
| 2010/0305702 A1* | 12/2010 | Michelson ................ 623/17.11 |
| 2010/0331981 A1 | 12/2010 | Mohammed |
| 2011/0009869 A1 | 1/2011 | Marino et al. |
| 2011/0022176 A1* | 1/2011 | Zucherman et al. ........ 623/17.11 |
| 2011/0034957 A1 | 2/2011 | Biedermann |
| 2011/0046737 A1* | 2/2011 | Teisen ................ 623/17.11 |
| 2011/0071568 A1 | 3/2011 | Ginn et al. |
| 2011/0071635 A1 | 3/2011 | Zhang et al. |
| 2011/0087294 A1 | 4/2011 | Reiley |
| 2011/0098816 A1 | 4/2011 | Jacob et al. |
| 2011/0098817 A1 | 4/2011 | Eckhardt et al. |
| 2011/0118796 A1 | 5/2011 | Reiley |
| 2011/0166575 A1 | 7/2011 | Assell et al. |
| 2011/0184518 A1 | 7/2011 | Trieu |
| 2011/0184519 A1 | 7/2011 | Trieu |
| 2011/0184520 A1 | 7/2011 | Trieu |
| 2011/0230966 A1 | 9/2011 | Trieu |
| 2011/0238181 A1 | 9/2011 | Trieu |
| 2011/0264229 A1 | 10/2011 | Donner |
| 2011/0264233 A1 | 10/2011 | Song |
| 2011/0295272 A1 | 12/2011 | Assell et al. |
| 2012/0010714 A1 | 1/2012 | Moskowitz et al. |
| 2012/0022535 A1 | 1/2012 | Mayer et al. |
| 2012/0022595 A1 | 1/2012 | Pham et al. |
| 2012/0029641 A1 | 2/2012 | Curran et al. |

(56) References Cited

U.S. PATENT DOCUMENTS

| | | |
|---|---|---|
| 2012/0083883 A1 | 4/2012 | Ginn |
| 2012/0095560 A1 | 4/2012 | Donner |
| 2012/0116454 A1 | 5/2012 | Edidin et al. |
| 2012/0116806 A1 | 5/2012 | Stark et al. |
| 2012/0150300 A1 | 6/2012 | Nihalani |
| 2012/0209388 A1 | 8/2012 | Curran et al. |
| 2012/0253398 A1 | 10/2012 | Metcalf et al. |
| 2012/0259370 A1 | 10/2012 | Vaidya |
| 2012/0271200 A1 | 10/2012 | Martinson et al. |
| 2012/0271424 A1 | 10/2012 | Crawford |
| 2012/0296428 A1 | 11/2012 | Donner |
| 2012/0316565 A1 | 12/2012 | Stark |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0035727 A1 | 2/2013 | Datta |
| 2013/0053854 A1 | 2/2013 | Schoenefeld et al. |
| 2013/0053902 A1 | 2/2013 | Trudeau |
| 2013/0053964 A1 | 2/2013 | Talwar |
| 2013/0060337 A1 | 3/2013 | Petersheim et al. |
| 2013/0066426 A1 | 3/2013 | Martinson et al. |
| 2013/0085535 A1 | 4/2013 | Greenhalgh et al. |
| 2013/0090735 A1 | 4/2013 | Mermuys et al. |
| 2013/0116790 A1 | 5/2013 | Seifert |
| 2013/0123923 A1 | 5/2013 | Pavlov et al. |
| 2013/0144343 A1 | 6/2013 | Arnett et al. |
| 2013/0197590 A1 | 8/2013 | Assell et al. |
| 2013/0218215 A1 | 8/2013 | Ginn et al. |
| 2013/0226181 A1 | 8/2013 | Assell et al. |
| 2013/0231746 A1 | 9/2013 | Ginn et al. |
| 2013/0282012 A1 | 10/2013 | Stark |
| 2013/0295202 A1 | 11/2013 | Stark |
| 2013/0297035 A1 | 11/2013 | Reiley |
| 2014/0012330 A1 | 1/2014 | Johnson, II et al. |
| 2014/0039628 A1 | 2/2014 | DeLurio et al. |
| 2014/0200618 A1 | 7/2014 | Donner et al. |
| 2014/0336775 A1 | 11/2014 | Reiley |

FOREIGN PATENT DOCUMENTS

| | | |
|---|---|---|
| CN | 201073333 Y | 6/2008 |
| CN | 201139628 Y | 10/2008 |
| CN | 201275132 | 7/2009 |
| CN | 201275133 | 7/2009 |
| CN | 201275134 | 7/2009 |
| CN | 202235633 U | 5/2012 |
| EP | 1663037 B1 | 6/2006 |
| EP | 2182865 | 5/2010 |
| JP | 2007-275592 | 10/2007 |
| KR | 10-1037206 B1 | 5/2011 |
| RU | 2364359 | 8/2009 |
| WO | WO/93/08745 | 5/1993 |
| WO | WO/93/08745 A1 | 5/1993 |
| WO | WO 95/23559 | 9/1995 |
| WO | WO 95/31947 | 11/1995 |
| WO | WO 01/30264 A2 | 5/2001 |
| WO | WO/01/95823 | 12/2001 |
| WO | WO/01/95823 A1 | 12/2001 |
| WO | WO02/03895 | 1/2002 |
| WO | WO/02/03895 A1 | 1/2002 |
| WO | WO/02/067759 | 9/2002 |
| WO | WO/02/067759 A2 | 9/2002 |
| WO | WO/02/067759 A3 | 9/2002 |
| WO | WO/2006/020463 | 2/2006 |
| WO | WO/2006/020463 A1 | 2/2006 |
| WO | WO 2006/099270 | 9/2006 |
| WO | WO 2007/022790 A1 | 3/2007 |
| WO | WO/2007/115295 | 10/2007 |
| WO | WO/2007/115295 A2 | 10/2007 |
| WO | WO/2007/115295 A3 | 10/2007 |
| WO | WO/2008/011410 | 1/2008 |
| WO | WO/2008/011410 A2 | 1/2008 |
| WO | WO/2008/011410 A3 | 1/2008 |
| WO | WO 2008/088685 A2 | 7/2008 |
| WO | WO 2008/089537 | 7/2008 |
| WO | WO/2008/089537 A1 | 7/2008 |
| WO | WO/2009/011774 | 1/2009 |
| WO | WO/2009/011774 A2 | 1/2009 |
| WO | WO/2009/011774 A3 | 1/2009 |
| WO | WO/2009/029074 | 3/2009 |
| WO | WO/2009/029074 A1 | 3/2009 |
| WO | WO/2009/108318 | 9/2009 |
| WO | WO/2009/108318 A2 | 9/2009 |
| WO | WO/2009/108318 A3 | 9/2009 |
| WO | WO 2010/045749 A1 | 4/2010 |
| WO | WO/2010/065015 | 6/2010 |
| WO | WO/2010/065015 A1 | 6/2010 |
| WO | WO 2010/108166 A1 | 9/2010 |
| WO | WO 2011014135 A2 | 2/2011 |
| WO | WO/2011/056690 | 5/2011 |
| WO | WO/2011/056690 A2 | 5/2011 |
| WO | WO 2011/066053 A2 | 6/2011 |
| WO | WO 2011/087912 A1 | 7/2011 |
| WO | WO 2011/091349 A2 | 7/2011 |
| WO | WO 2012/015976 A1 | 2/2012 |
| WO | WO 2012/174485 A1 | 12/2012 |
| WO | WO 2013/020123 A2 | 2/2013 |
| WO | WO 2013/043584 A1 | 3/2013 |

OTHER PUBLICATIONS

Buchowski, et al. Functional and Radiographic Outcome of Sacroiliac Arthrodesis for the Disorders of the Sacroiliac Joint. The Spine Journal, 5, 2005, pp. 520-528.

Ebraheim, et al. A Posterior Approach for Inspection of Reduction of Sacroiliac Joint Disruption. Surg. Radiol. Anat., 1999, 21(5), pp. 305-307.

Ebraheim, et al. Anatomic Considerations for Posterior Approach to the Sacroiliac Joint. Spine, 21(23), Dec. 1, 1996, pp. 2709-2712.

Giannikas, et al. Sacroiliac Joint Fusion for Chronic Pain: A Simple Technique Avoiding the Use of Metalwork. Eur. Spine J, 13, 2004, pp. 253-256.

Güner, et al. Anterior Sacroiliac Fusion. A New Video-Assisted Endoscopic Technique. Surgical Laparoscopy & Endoscopy, 8(3), pp. 233-236.

Puhakka, et al. MR Imaging of the Normal Sacroiliac Joint with Correlation to Histology. Skeletal Radiol., 33, 2004, pp. 15-28.

Stark. The Diagnosis and Treatment of Sacroiliac Joint Abnormalities. Current Orthopedic Practice, 21(4), Jul./Aug. 2010, pp. 336-347.

Szadek, et al. Possible Nociceptive Structures in the Sacroiliac Joint Cartilage: An Immunohistochemical Study. Clinical Anatomy, 23, 2010, pp. 192-198.

Ugur, et al. New Needle Holder Facilitates Percutaneous Fluoroscopy-Guided Sacroiliac Puncture. Acta Radiologica, 2006, 47(5), pp. 481-483.

Vanelderen, et al. Evidence-Based Medicine. Evidence-Based Interventional Pain Medicine According to Clinical Diagnoses. 13. Sacroiliac Joint Pain. Pain Practice, 10(5), 2010.

Waisbrod, et al. Sacroiliac Joint Arthrodesis for Chronic Lower Back Pain. Arch Orthop Trauma Surg, 106, 1987, pp. 238-240.

Wise, et al. Minimally Invasive Sacroiliac Arthrodesis. Outcomes of a New Technique. Spinal Disord. Tech., 21(8), Dec. 2008, pp. 579-584.

U.S. Appl. No. 13/475,695, filed May 18, 2012, Donner.

Arman et al. The Human Sacrum and Safe Approaches for Screw Placement. *Journal of Clinical Neuroscience* 2008 Elsevier Inc.;16(2009):1046-1049.

Atlihan et al. Anatomy of the Posterior Illiac Crest as a Reference to Sacral Bar Insertion. *Clin Orthop* 2004;418:141-145.

Cecil et al. Projection of the S2 Pedicle Onto the Posterolateral Surface of the Ilium: A Technique for Lag Screw Fixation, Sacral Fractures or Sacroiliac Joint Dislocations. *Spine* 1996;21(7):875-878.

Chang et al. Low Profile Pelvic Fixation. *Spine* 2009;34(5):436-440.

Lee et al. Trajectory of Transsacral Iliac Screw for Lumbopelvic Fixation. *J Spinal Disord Tech* 2011;24(3):151-156.

(56) References Cited

OTHER PUBLICATIONS

Lehman, Jr. et al. Advantage of Pedicle Screw Fixation Directed Into the Apex of the Sacral Promontory Over Bicortical Fixation. *Spine* 2002;27(8):806-811.
Luk et al. A Stronger Bicortical Sacral Pedicle Screw Fixation Through the S1 Endplate. *Spine* 2005;30(5):525-529.
Martin et al. Sacropelvic Fixation: Two Case Reports of a New Percutaneous Technique. *Spine* 2011;36(9):E618-21.
Mendel et al. The Lateral Sacral Triangle—A Decision Support for Secure Transverse Sacroiliac Screw Insertion. *Injury J. Care Injured* 2010;42(2011):1164-1170.
Moshirfar et al. Pelvic Fixation in Spine Surgery. *The Journal of Bone & Joint Surgery* 2005;87-A(2 Suppl):89-106.
O'Brien et al. An Anatomic Study of the S2 Iliac Technique for Lumbopelvic Screw Placement. *Spine* 2009;34(12):E439-E442.
O'Brien et al. Feasibility of Minimally Invasive Sacropelvic Fixation. *Spine* 2010;35(4):460-464.
O'Brien et al. Sacropelvic Instrumentation: Anatomic and Biomechanical Zones of Fixation. *Seminars in Spine Surgery* 2004;16(2):76-90.
Ouellet et al. Surgical Anatomy of the Pelvis, Sacrum, and Lumbar Spine Relevant to Spinal Surgery. *Seminars in Spine Surgery* 2004 Elsevier Inc.;16:91-100.
U.S. Appl. No. 13/135,381, filed Jul. 1, 2011, Donner.
U.S. Appl. No. 13/236,411, filed Sep. 19, 2011, Donner.
Non-Final Office Action, U.S. Appl. No. 13/135,381, mailed Nov. 5, 2012, 19 pages.
International Search Report and Written Opinion, PCT application No. PCT/US2012/042823, dated Nov. 5, 2012, 16 pages.
U.S. Appl. No. 13/945,053, filed Jul. 18, 2013, Donner.
Advisory Action, U.S. Appl. No. 13/135,381, mailed Jul. 23, 2013, 3 pages.
Baria, Dinah, "Sacroiliac Joint Biomechanics and Effects of Fusion" (2010). Open Access Dissertations. Paper 466. http://scholarlyrepository.miami.edu/oa_dissertations, 179 pages.
Belanger, et al. "Sacroiliac Arthrodesis Using a Posterior Midline Fascial Splitting Approach and Pedicle Screw Instrumentation: A New Technique." Journal of Spinal Disorders, vol. 14 No. 2, pp. 118-124, 2001.
Dayer R. et al. Pelvic fixation for neuromuscular scoliosis deformity correction. *Curr Rev Musculoskelet Med* (2012) 5:91-101.
DePuy Spine. ISOLA® Spinopelvic System, Surgical Technique. c. 2003 DePuy Spine, Inc., 28 pages.
Final Rejection, U.S. Appl. No. 13/135,381, mailed May 9, 2013, 14 pages.
Garrido B.J. et al. Navigated placement of iliac bolts: description of a new technique. *The Spine Journal* 11 (2011) 331-335.
Globus Medical. REVERE® ADDITION® Sacroiliac Components, Surgical Technique. c. 2012 Globus Medical, 64 pages.
Globus Medical. SI-LOK™ Sacroiliac Joint Fixation System, Surgical Technique. c. 2011 Globus Medical, 44 pages.
International Search Report and Written Opinion, PCT Application No. PCT/US2012/055892, dated Mar. 25, 2013, 22 pages.
LDR. Avenue® L Lateral Lumbar Cage. Sep. 2011, 3 pages.
LDR. ROI-A™ Anterior Approach Implant. Apr. 2008, 2 pages.
LDR. Surgical Technique ROI-C™ Anterior Cervical Cage. Apr. 2010, 15 pages.
Marotta N. et al. A novel minimally invasive presacral approach and instrumentation technique for anterior L5-S1 intervertebral disectomy and fusion. *Neurosurg Focus*, vol. 20, Jan. 2006, 8 pages.
McLauchlan, et al. "Sacral and Iliac Articular Cartilage Thickness and Cellularity: Relationship to Subchondral Bone End-Plate Thickness and Cancellous Bone Density." Rheumatology 2002; 41:375-380.
Pan W. et al. The invention of an iliosacral screw fixation guide and its preliminary clinical application. *Orthopaedic Surgery* (2012), vol. 4, No. 1, pp. 55-59.
Response to Advisory Action, U.S. Appl. No. 13/135,381, filed Aug. 20, 2013, 12 pages.
Response to Final Office Action, U.S. Appl. No. 13/135,381, filed Jul. 9, 2013, 11 pages.
Response to Non-Final Office Action, U.S. Appl. No. 13/135,381, filed Feb. 4, 2013, 7 pages.
Response to Restriction, U.S. Appl. No. 13/236,411, filed Jun. 10, 2013, 13 pages.
Restriction Requirement, U.S. Appl. No. 13/236,411, mailed May 10, 2013, 5 pages.
SI-BONE iFuse Implant System, Surgical Technique Manual. c. 2011 SI-BONE, Inc., 35 pages.
Signus Medizintechnik GmbH. DIANA Operationstechnik. Rev. May 1, 2010, 20 pages.
Sponseller P.D. et al. Low profile pelvic fixation with the sacral alar iliac technique in the pediatric population improves results at two-year mninimum follow-up. *Spine* vol. 35, No. 20, pp. 1887-1892.
Stark J. G. et al. The history of sacroiliac joint arthrodesis: a critical review and introduction of a new technique. *Current Orthopaedic Practice*, vol. 22, No. 6, Nov./Dec. 2011, pp. 545-557.
Synthes Spine. SynFix-LR System. Instruments and implants for stand-alone anterior lumbar interbody fusion (ALIF). Technique Guide. © 2008 Synthes, Inc., 45 pages.
Synthes Spine. Universal Spinal System (USS) Polyaxial and Iliosacral Spine Fixation. A versatile system for posterior stabilization of spinal segments. Technique Guide, c. 2009 Synthes, Inc., 61 pages.
Tifix® Technology Pressure Plate Technology: Multidirectional Locking Technology Titanium Plate and Screw Systems, General & Specific Instructions. Iitos/GmbH & Co. KG, Rev: Sep. 9, 2008.
Tobler W.D. et al. The presacral retroperitoneal approach for axial lumbar interbody fusion. *J Bone Joint Surg* [*Br*], vol. 93-B, No. 7, Jul. 2011, pp. 955-960.
Yin, et al. "Sensory Stimulation-Guided Sacroiliac Joint Radiofrequency Neurotomy: Technique Based on Neuroanatomy of the Dorsal Sacral Plexus." Spine, 28(20), pp. 2419-2425.
Zyga Technology, Inc. Slmmetry Sacroiliac Joint Fusion System, Surgeon Didactic, c. 2012 Zyga Technology, Inc., 45 pages.
Zyga Technology, Inc. Slmmetry Sacroiliac Joint Fusion System, Technique Guide, known at least as early as Mar. 1, 2013, 20 pages.
Appeal Brief, U.S. Appl. No. 13/135,381, dated Dec. 23, 2013, 20 pages.
European Search Report, EP Appl. No. 11733183.5, dated Dec. 18, 2013, 4 pages.
International Search Report and Written Opinion, PCT Application No. PCT/US2013/051381, dated Nov. 4, 2013, 16 pages.
Response to Restriction, U.S. Appl. No. 13/236,411, filed Nov. 12, 2013, 14 pages.
Restriction Requirement, U.S. Appl. No. 13/236,411, mailed Oct. 16, 2013, 7 pages.
Singapore Search Report and Written Opinion, SG Appl. No. 201205104-1, dated Oct. 31, 2013, 29 pages.
Liebergall, Meir (IRI) M.D., *Lumbosacral and Spinopelvic Fixation*, Lippincott-Raven, Philadelphia, PA, 1996, Chap. 48, "Sacroiliac Joint Fusion," pp. 611-618.
Margulies, J.Y. et al., *Movement, Stability & Low Back Pain, The essential role of the pelvis*, Churchill Livingstone, London, 1997, Chapters 44-47, "Surgical Fusion of the Spine to the Sacrum, etc.," pp. 555-593.
Non-Final Office Action, U.S. Appl. No. 13/236,411, dated Apr. 11, 2014.
Notice of Allowance, U.S. Appl. No. 13/135,381, dated Apr. 17, 2014.
Synthes Spine. ProDisc-C Total Disc Replacement. Product Information. © 2008 Synthes, Inc., 14 pages.
International Search Report and Written Opinion, PCT/US2014/030889, dated Jul. 16, 2014.
European Search Report, EP Appl. No. 12799773.2, dated Oct. 29, 2014.
Examination Report, SG Application No. 201205104-1, dated Jul. 17, 2014, Intellectual Property Office of Singapore.
Japanese Office Action, JP2012-548960, dated Oct. 7, 2014.

(56) References Cited

OTHER PUBLICATIONS

Restriction Requirement, U.S. Appl. No. 13/945,053, dated Sep. 25, 2014.
Tenon Medical, *Catamaran SI Joint Implant*, http://tctig.com/projects (last visited Nov. 19, 2014).
U.S. Appl. No. 14/447,612, filed Jul. 31, 2014.
Response to Non-Final Office Action, U.S. Appl. No. 13/236,411, dated Sep. 11, 2014.
International Search Report and Written Opinion, PCT/US2014/048990, dated Nov. 18, 2014.
Response to Restriction, U.S. Appl. No. 13/945,053, dated Nov. 19, 2014.

\* cited by examiner

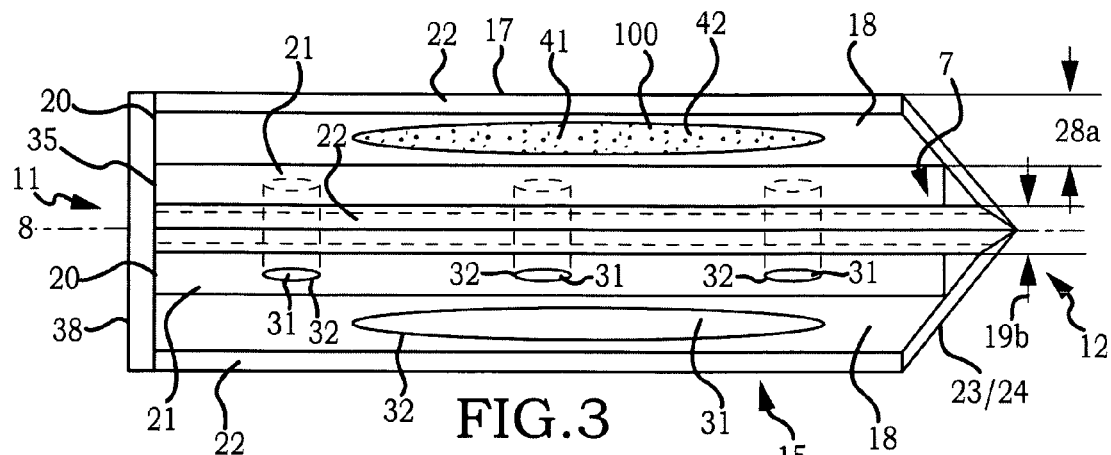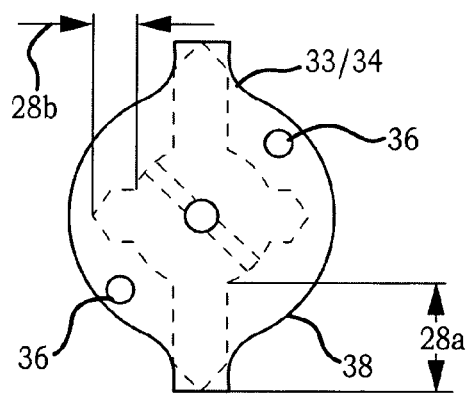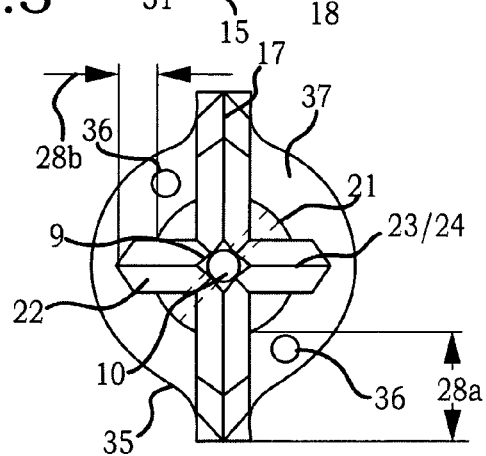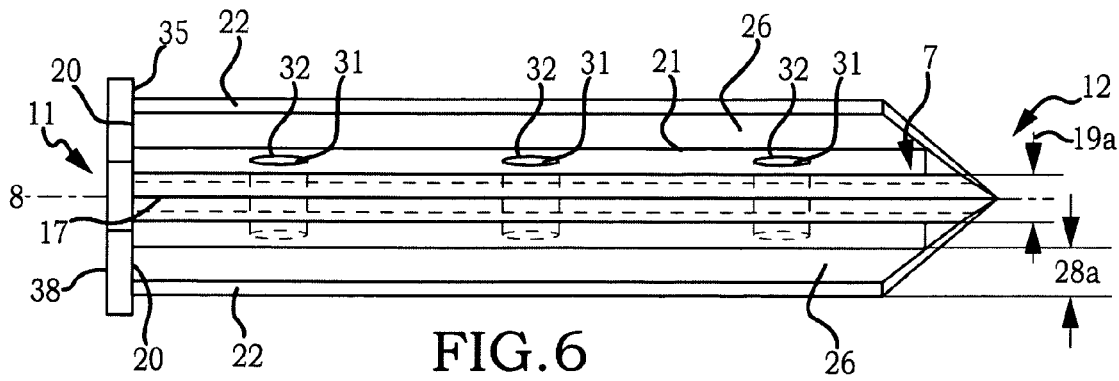

SACROILIAC JOINT FIXATION FUSION SYSTEM

This application is the U.S. National Stage of International Patent Cooperation Treaty Application No. PCT/US11/00070, filed Jan. 13, 2011, which claims the benefit of U.S. Provisional Patent Application No. 61/335,947, filed Jan. 13, 2010, each hereby incorporated by reference herein.

I. TECHNICAL FIELD

Generally, a sacroiliac joint fixation fusion system that provides a method of fixation and fusion of the sacroiliac joint and a sacroiliac joint implant which upon placement within the articular space of the sacroiliac joint facilitates stability and fusion of the sacroiliac joint.

II. BACKGROUND

The sacroiliac joint is the joint between the sacrum and the ilium of the pelvis, which are joined by ligaments. In humans, the sacrum supports the spine and is supported in turn by an ilium on each side. The sacroiliac joint is a synovial joint with articular cartilage and irregular elevations and depressions that produce interlocking of the two bones.

Pain associated with the sacroiliac joint can be caused by traumatic fracture dislocation of the pelvis, degenerative arthritis, sacroiliitis an inflammation or degenerative condition of the sacroiliac joint, osteitis condensans ilii, or other degenerative conditions of the sacroiliac joint. Currently, sacroiliac joint fusion is most commonly advocated as a surgical treatment for these conditions. Fusion of the sacroiliac joint can be accomplished by several different conventional methods encompassing an anterior approach, a posterior approach, and a lateral approach with or without percutaneous screw or other type implant fixation. However, while each of these methods have been utilized for fixation and fusion of the sacroiliac joint over the past several decades, substantial problems with respect to the fixation and fusion of the sacroiliac joint remain unresolved.

A significant problem with certain conventional methods for fixation and fusion of the sacroiliac joint including the anterior approach, posterior approach, or lateral approach may be that the surgeon has to make a substantial incision in the skin and tissues for direct access to the sacroiliac joint involved. These invasive approaches allow the sacroiliac joint to be seen and touched directly by the surgeon. Often referred to as an "open surgery", these procedures have the attendant disadvantages of requiring general anesthesia and can involve increased operative time, hospitalization, pain, and recovery time due to the extensive soft tissue damage resulting from the open surgery. A danger to open surgery using the anterior approach can be damage to the L5 nerve root which lies approximately two centimeters medial to the sacroiliac joint or damage to the major blood vessels. Additionally, these procedures typically involve fixation of the sacroiliac joint (immobilization of the articular surfaces of the sacroiliac joint in relation to one another) by placement of one or more screws or by placement of one or more trans-sacroiliac implants (as shown by the non-limiting example of FIG. 1) or by placement of implants into the S1 pedicle and iliac bone. Use of trans-sacroiliac and S1 pedicle-iliac bone implants can also involve the risk of damage to the lumbosacral neurovascular elements. Damage to the lumbosacral neurovascular elements as well as delayed union or non-union of the sacroiliac joint by use of these procedures may require revision surgery to remove all or a portion of the implants or repeat surgery as to these complications.

Another significant problem with conventional procedures utilizing minimally invasive small opening procedures can be that the procedures are technically difficult requiring biplanar fluoroscopy of the articular surfaces of the sacroiliac joint and extensive surgical training and experience. Despite the level of surgical training and experience, there is a substantial incidence of damage to the lumbosacral neurovascular elements. Additionally, sacral anomalies can further lead to malplacement of implants leading to damage of surrounding structures. Additionally, these procedures are often performed with out fusion of the sacroiliac joint which does not remove the degenerative joint surface and thereby does not address the degenerative condition of the sacroiliac joint which may lead to continued or recurrent sacroiliac joint pain.

Another significant problem with conventional procedures can be the utilization of multiple trans-sacroiliac elongate implants, which do not include a threaded surface. This approach requires the creation of trans-sacroiliac bores in the pelvis and nearby sacral foramen which can be of relatively large dimension and which are subsequently broached with instruments which can result in bone being impacted into the pelvis and neuroforamen.

The creation of the trans-sacroiliac bores and subsequent broaching of the bores requires a guide pin which may be inadvertently advanced into the pelvis or sacral foramen resulting in damage to other structures. Additionally, producing the trans-sacroiliac bores, broaching, or placement of the elongate implants may result in damage to the lumbosacral neurovascular elements, as above discussed. Additionally, there may be no actual fusion of the articular portion of the sacroiliac joint which may result in continued or recurrent pain requiring additional surgery.

Another substantial problem with conventional procedures can be that placement of posterior extra-articular distracting fusion implants and bone grafts as described for example in U.S. patent application Ser. No. 10/797,481 of Stark may be inadequate with respect to removal of the articular surface or preparation of cortical bone, the implant structure and fixation of the sacroiliac joint. The method may not remove sufficient amounts of the articular surfaces or cortical surfaces of the sacroiliac joint to relieve pain in the sacroiliac joint. The implant structures described may have insufficient or avoid engagement with the articular surfaces or cortical bone of the sacroiliac joint for adequate fixation or fusion. The failure to sufficiently stabilize and fuse the sacroiliac joint with the implant structures and methods described by the Stark application may result in a failure to relieve the condition of sacroiliac joint being treated. Additionally, the method of driving apart a sacrum and ilium as described by Stark may lead to mal-alignment of the sacroiliac joint and increased pain.

The inventive sacroiliac fusion system described herein addresses the problems associated with conventional methods and apparatuses used in fixation and fusion of the sacroiliac joint.

III. DISCLOSURE OF INVENTION

Accordingly, a broad object of the invention can be to provide an inventive sacroiliac joint implant for fixation and fusion of the sacroiliac joint. Embodiments of the sacroiliac joint implant can provide an elongate body, which can further include at least one radial member, or a pair of members which extend distance radially outward from the longitudinal axis of the elongate body adapted for non-transverse placement between the articular surfaces of the sacroiliac joint and as to certain embodiments can further provide a third radial member and additionally a fourth radial member each adapted to extend a distance radially outward from the longitudinal axis of the elongate body into the bone of the sacrum or the ilium.

Another broad object of the invention can be to provide an inventive method for fixation and fusion of the sacroiliac joint which utilizes the inventive sacroiliac implant. The inventive method comprising the steps of performing a minimally invasive posterior surgery that allows access to the posterior aspect of the sacroiliac joint for removing a sufficient portion of the articular cartilage or tissue between the articular surfaces of the sacroiliac joint which can be replaced by embodiments of the above described sacroiliac implant. A portion of the subcondral bone of the sacroiliac joint can be removed to provide an implant receiving space in the plane of the sacroiliac joint (non-trans-sacroiliac) configured to allow interference fitting of the elongate member, or the elongate member with at least a first radial member between the opposed surfaces of the implant receiving space. The inventive method can further include the step of providing the implant receiving space with one or more radial member receiving channels cut into the bone (including one or more of the subchondral, cortical, or cancellous) and thereby locating one or more radial members in the bone of the sacrum or the bone of the ilium. The inventive method avoids conventional trans-sacroiliac placement of fixation elements or S1 pedicle and intrailiac screws joined by a rod while providing immediate fixation of the sacroiliac joint.

Another broad object of the invention can be to provide one or more bone ingrowth aperture elements which communicate between the opposed surfaces of one or more radial members or through the generally linear elongate body each having a configuration which allows the bone of the sacrum and ilium to grow into or through the implant to facilitate fusion of the sacrum to the ilium and fixation of the sacroiliac joint.

Another broad object of the invention can be to provide particular embodiments of the inventive fixation fusion implant with an amount of curvature along the length of the implant which allows placement of embodiments of the fixation fusion implant which have an increased surface area which remain within or substantially within the articular portion of the sacroiliac joint.

Naturally, further objects of the invention are disclosed throughout other areas of the specification, drawings, photographs, and claims.

IV. BRIEF DESCRIPTION OF THE DRAWINGS

FIG. 3 is a first side view of a particular embodiment of the sacroiliac joint implant.

FIG. 4 is a first implant end view of a particular embodiment of the sacroiliac joint implant.

FIG. 5 is a second implant end view of a particular embodiment of the sacroiliac joint implant.

FIG. 6 is second side view of the particular embodiment of the sacroiliac joint implant shown in FIG. 3 rotated about 90 degrees about the longitudinal axis.

Figure 26A:
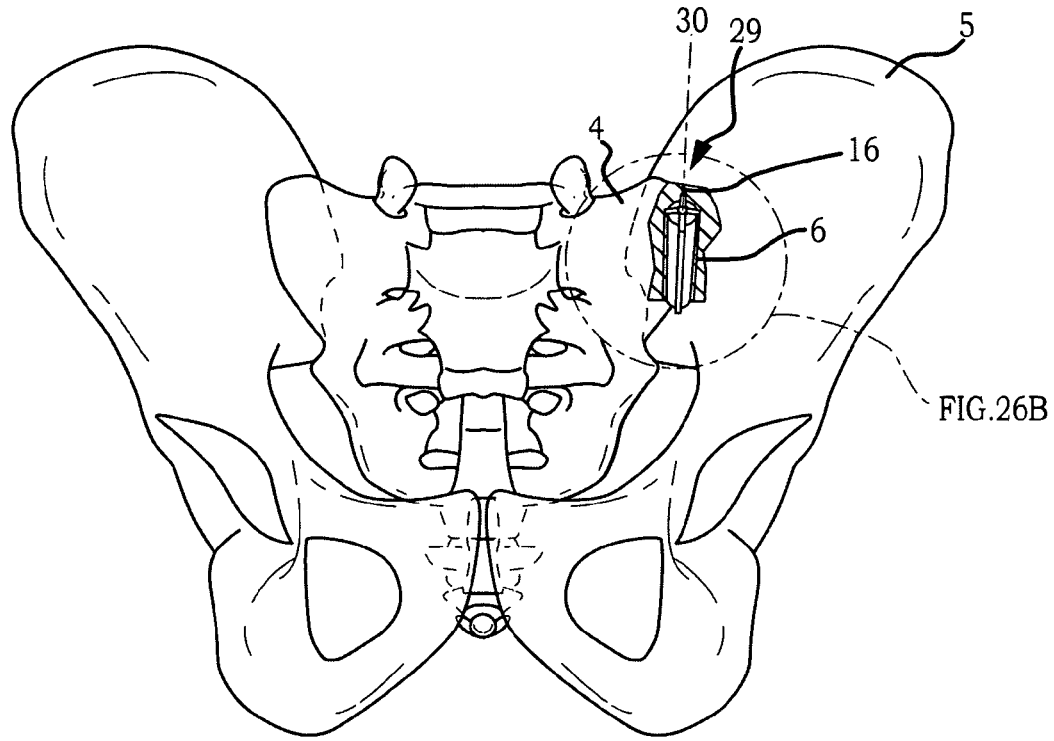

FIG. 26A provides a cutaway view of the sacroiliac joint showing placement of a particular embodiment of the fixation fusion implant in the implant receiving space produced by the method illustrated in FIGS. 16-24.

Figure 26B:
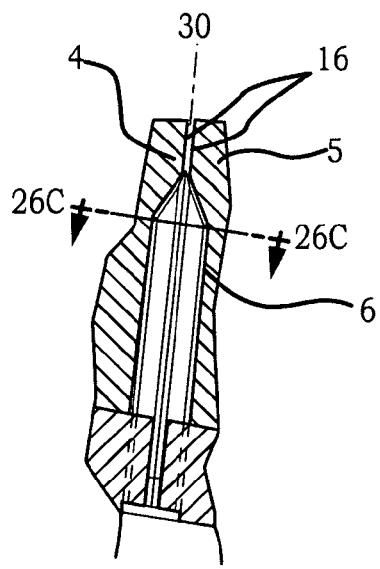

FIG. 26B is an enlarged view of a portion of FIG. 26A showing placement of a particular embodiment of the fixation fusion implant in the implant receiving space produced by the method illustrated in FIGS. 16-24.

Figure 24:
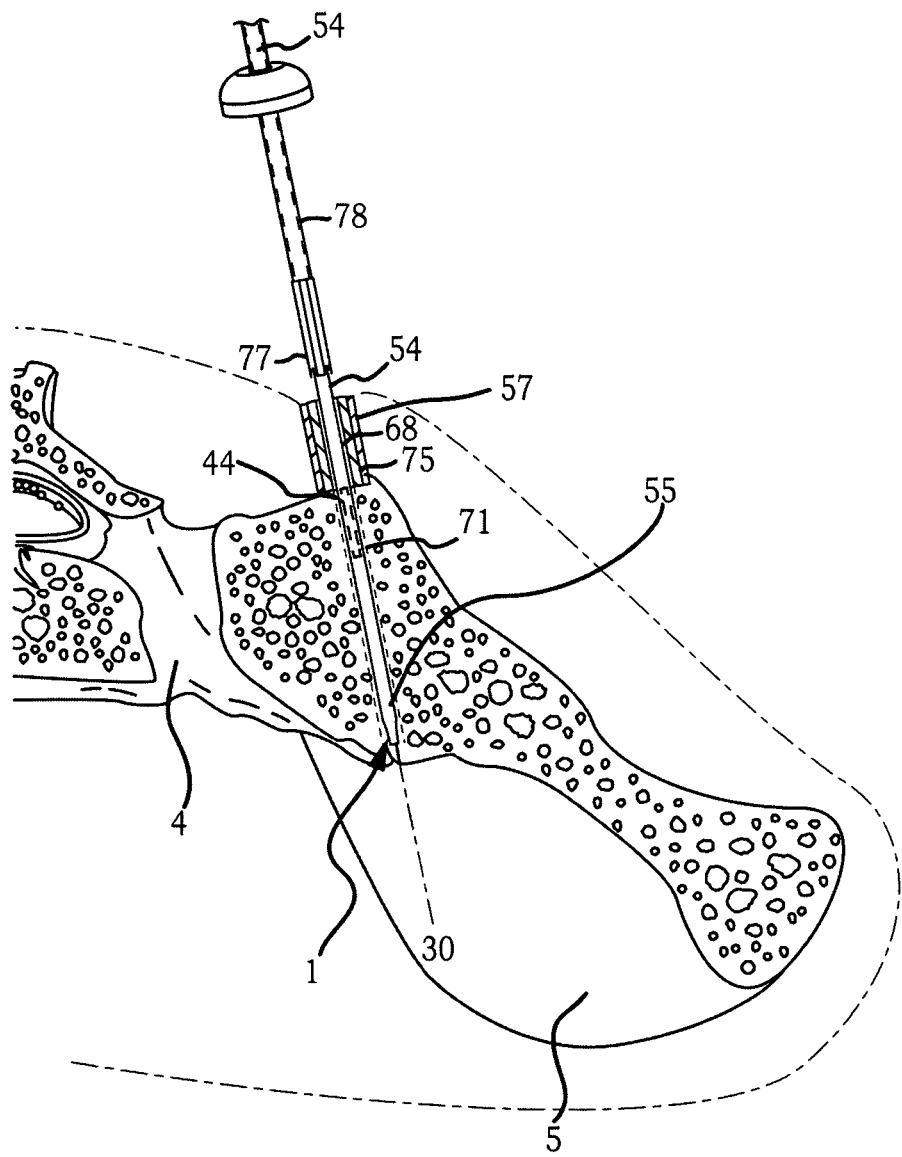
FIG. 24 is a cross section view through the sacroiliac joint which illustrates a method of implanting an embodiment of the fixation fusion implant the step including replacement of the second drill jig (or the first drill jig depending on the method) with a broach jig which receives a cannulated broach which can be advanced into the sacroiliac joint to produce an implant receiving space.
Figure 25:
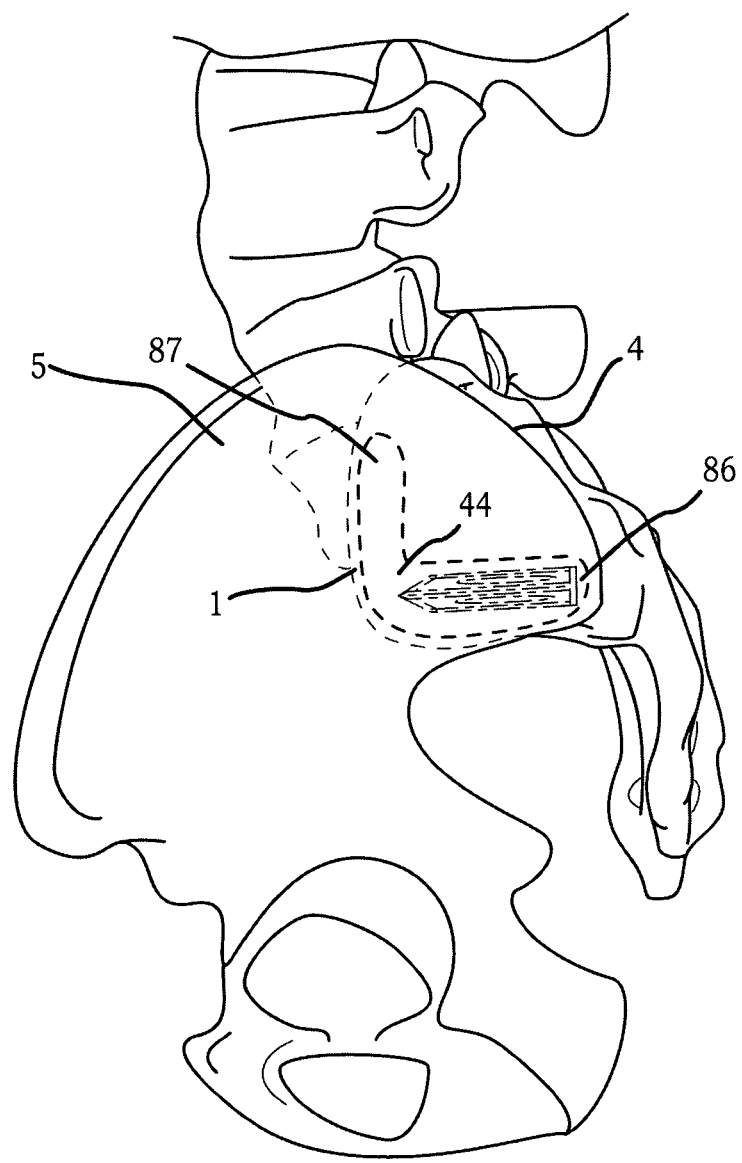
FIG. 25 is a lateral view of the pelvic region which shows an embodiment of the sacroiliac joint implant located between the caudal articular surfaces (shown in broken line) of the sacroiliac joint.
Figure 26C:
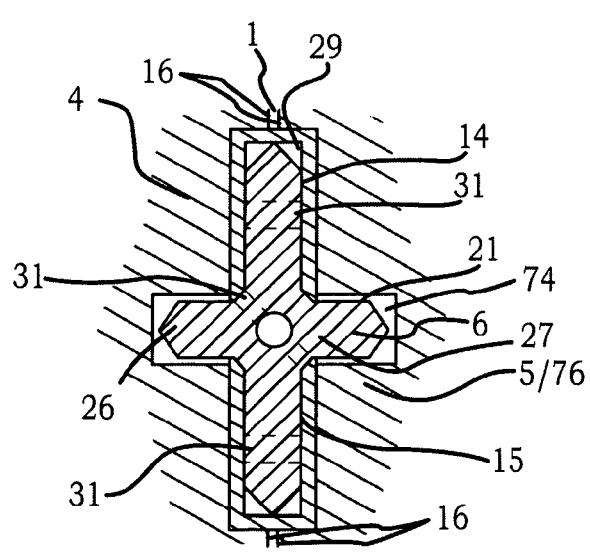

FIG. 26C is a cross section view 26C-26C shown in FIG. 26B which shows the configuration of the implant receiving space produced by the method illustrated in FIGS. 16-25 and a particular embodiment of the fixation fusion implant implanted therein implanted.

Figure 27:
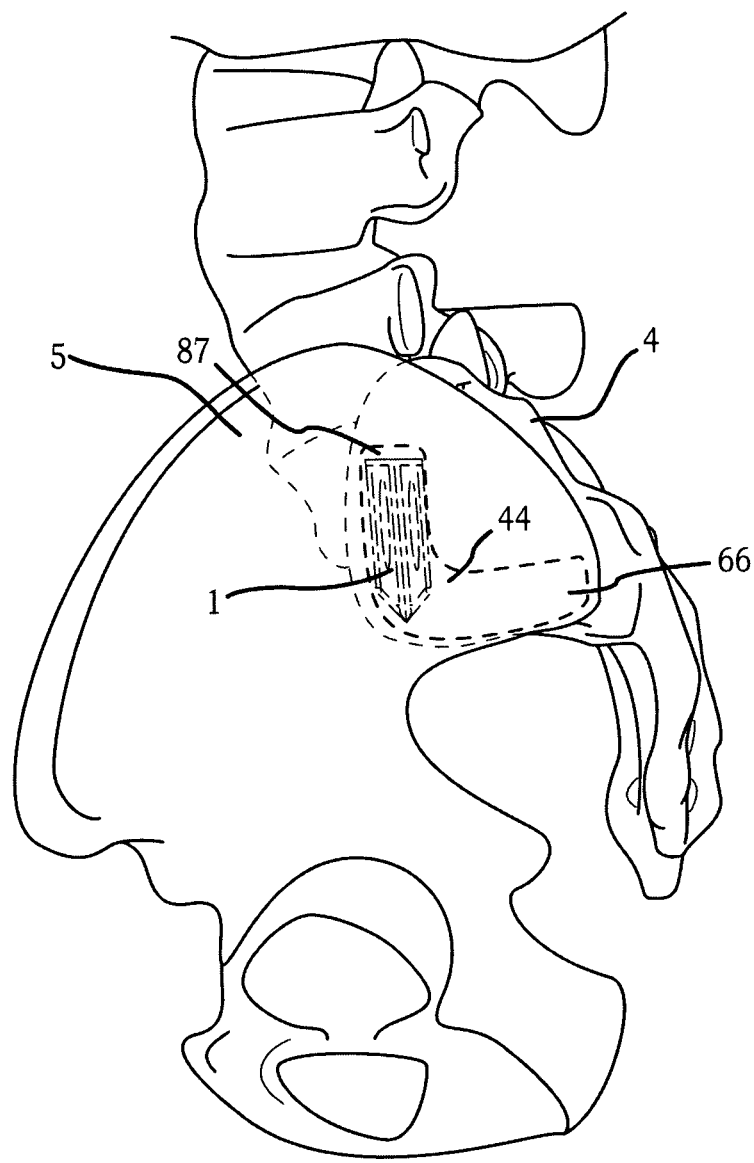

FIG. 27 provides a lateral view of the pelvis showing an embodiment of the sacroiliac implant located between the cranial articular surfaces (shown in broken line) within articular plane of the sacroiliac joint.

Figure 28A:
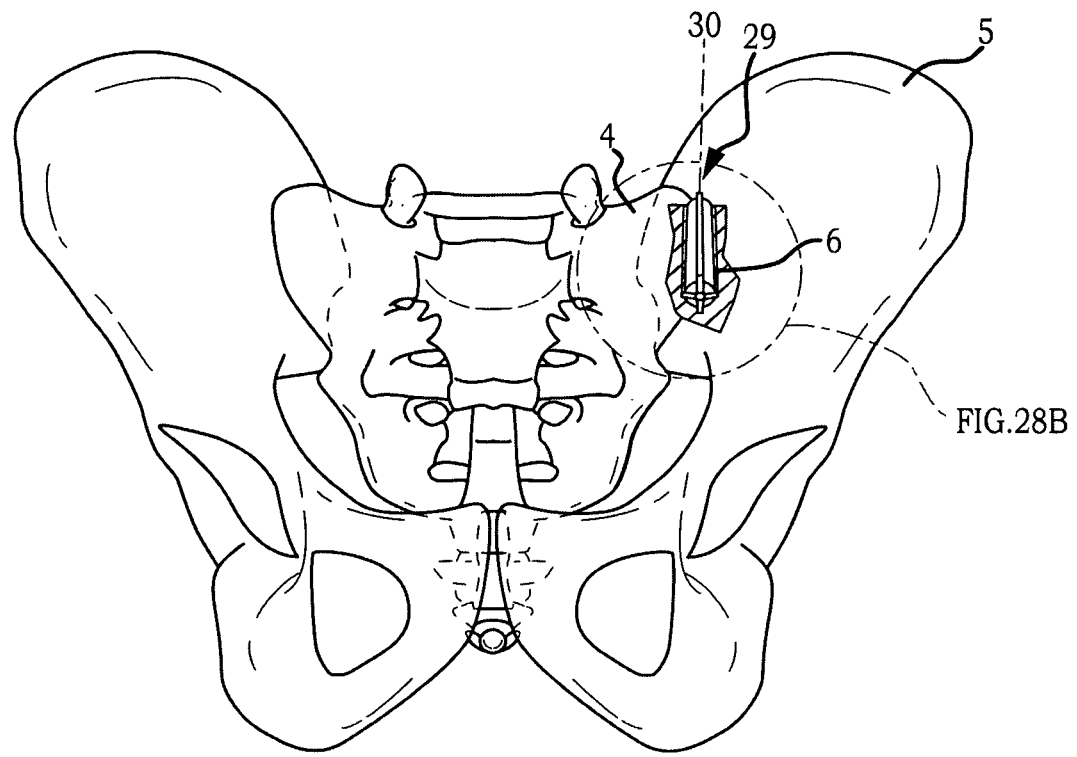

FIG. 28A provides a cutaway view of the sacroiliac joint showing placement of a particular embodiment of the fixation fusion implant in the implant receiving space produced by the method illustrated in FIGS. 16-24.

Figure 28B:
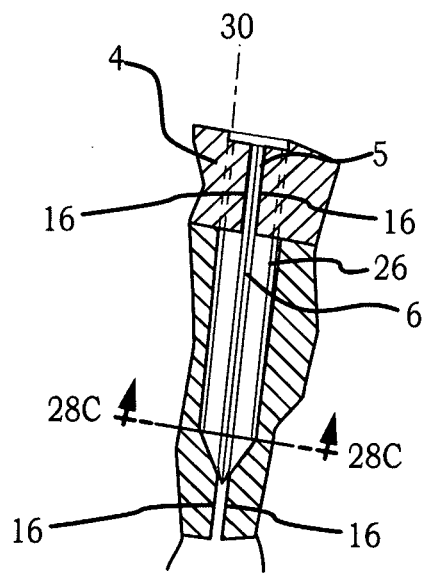

FIG. 28B is an enlarged view of a portion of FIG. 26A showing placement of a particular embodiment of the fixation fusion implant in the implant receiving space produced by the method illustrated in FIGS. 16-24.

Figure 28C:
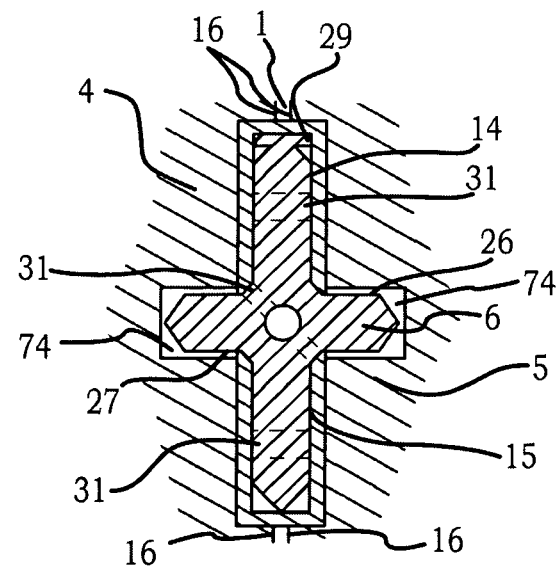

FIG. 28C is a cross section view 28C-28C shown in FIG. 28B which shows the configuration of the implant receiving space produced by the method illustrated in FIGS. 16-24 and a particular embodiment of the fixation fusion implant implanted therein implanted.

Figure 29:
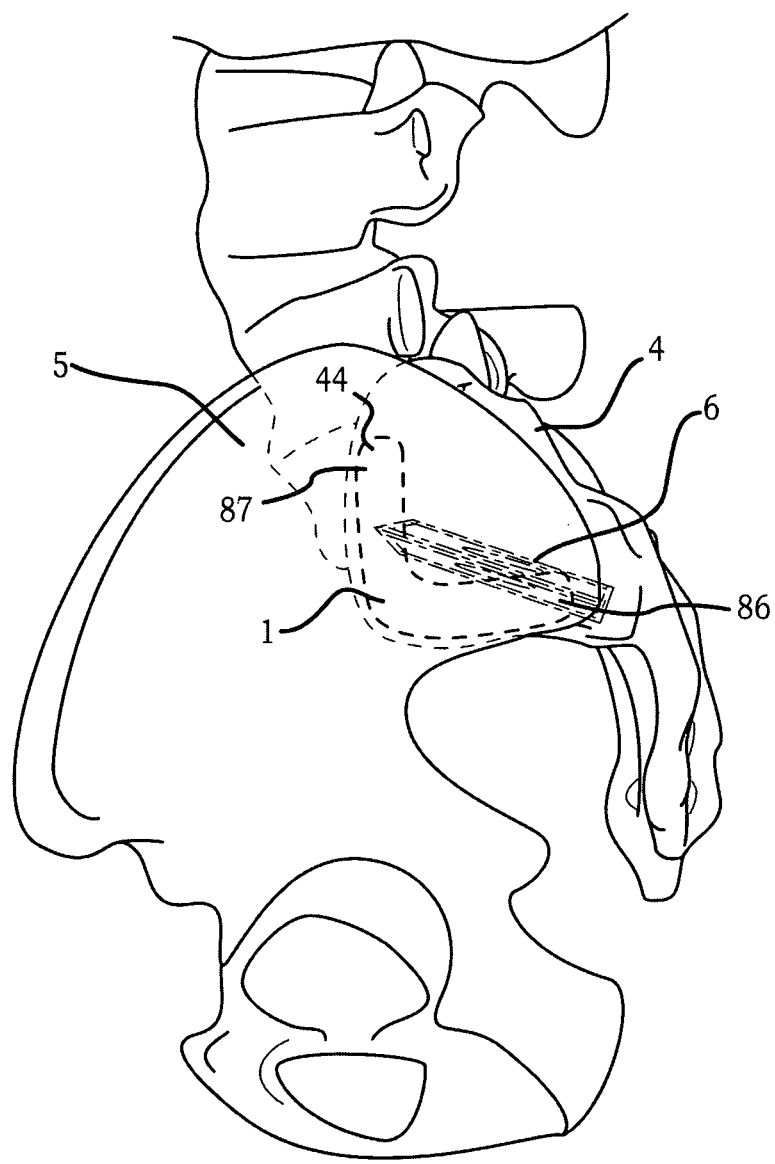

FIG. 29 provides a lateral view of the pelvis with an embodiment of the fixation fusion implant located substantially between the cranial and caudal articular surfaces (shown in broken line) and to a limited extent extra-articular of the sacroiliac joint.

Figure 30:
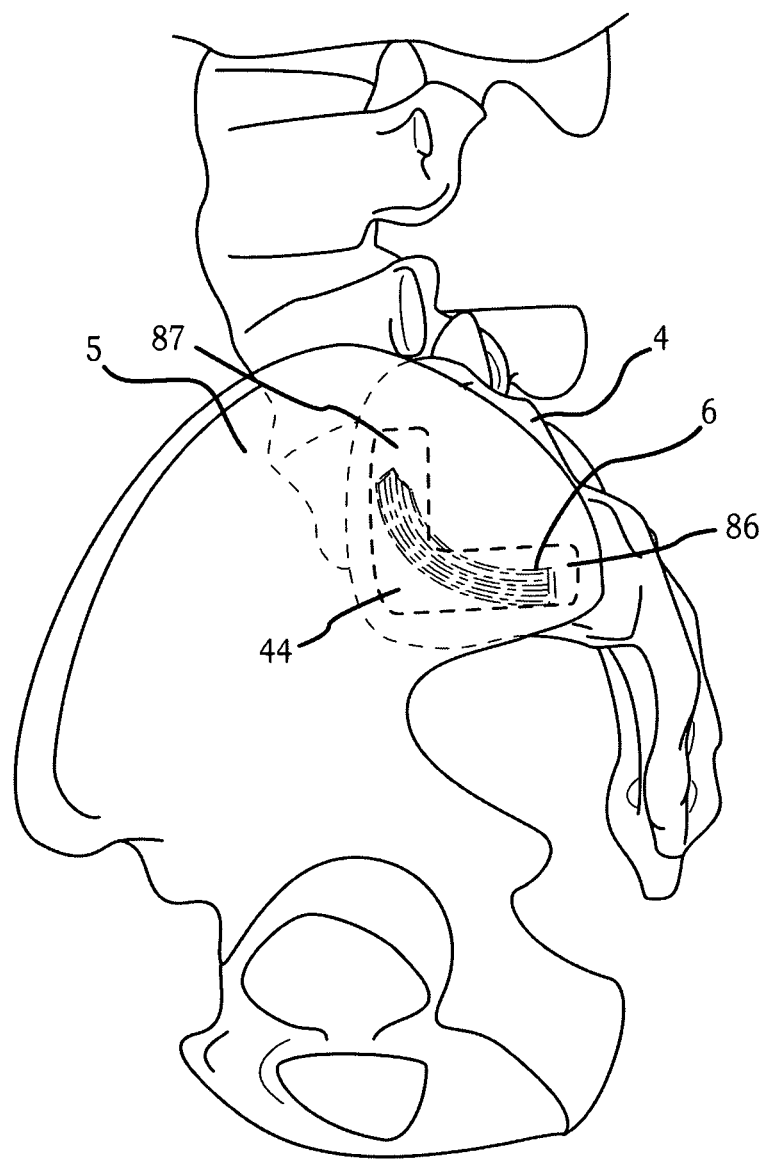

FIG. 30 provides a lateral view of the pelvis with an embodiment of the fixation fusion implant located between the cranial and caudal articular surfaces (shown in broken line) within the articular plane of the sacroiliac joint.

Figure 31:
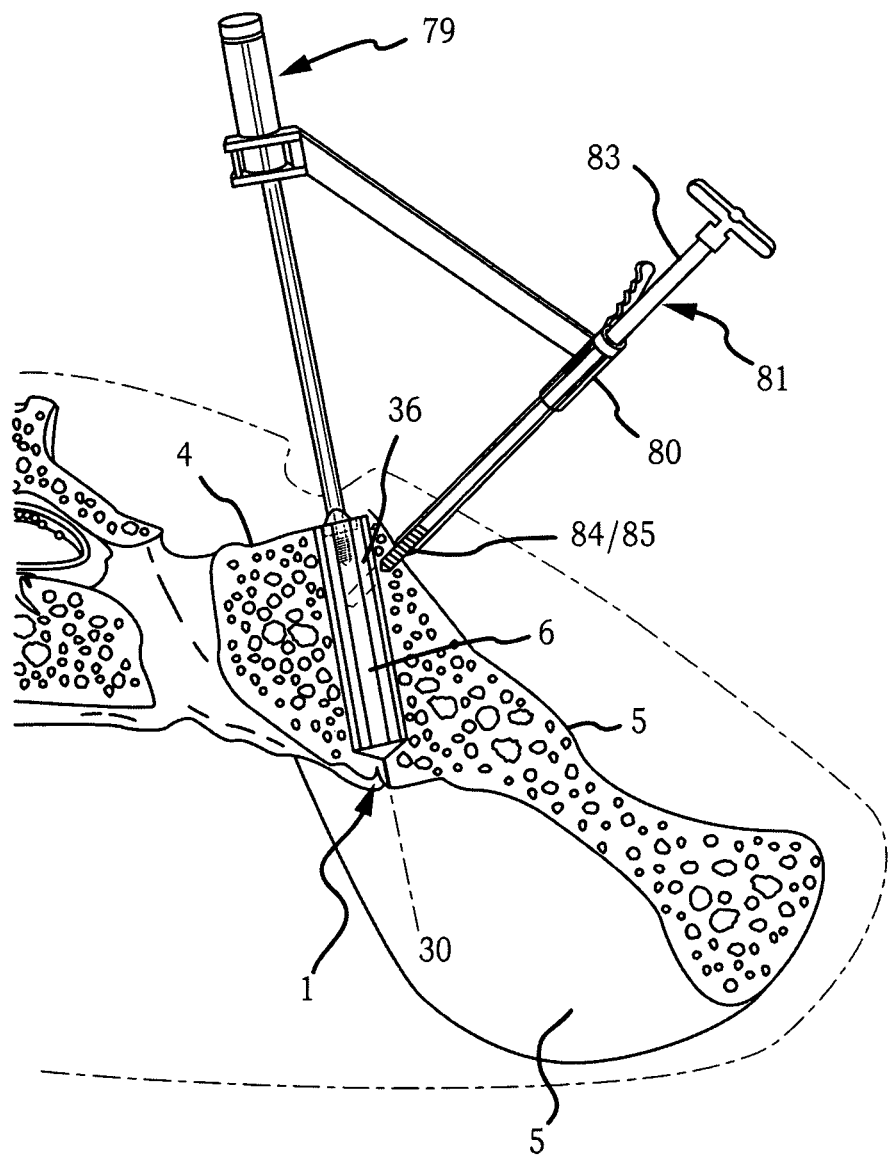

FIG. 31 is a cross section view through the sacroiliac joint which illustrates an alignment tool attachable to an implanted sacroiliac joint implant which aligns an elongate member to pass through the sacroiliac joint implant.

Figure 32:
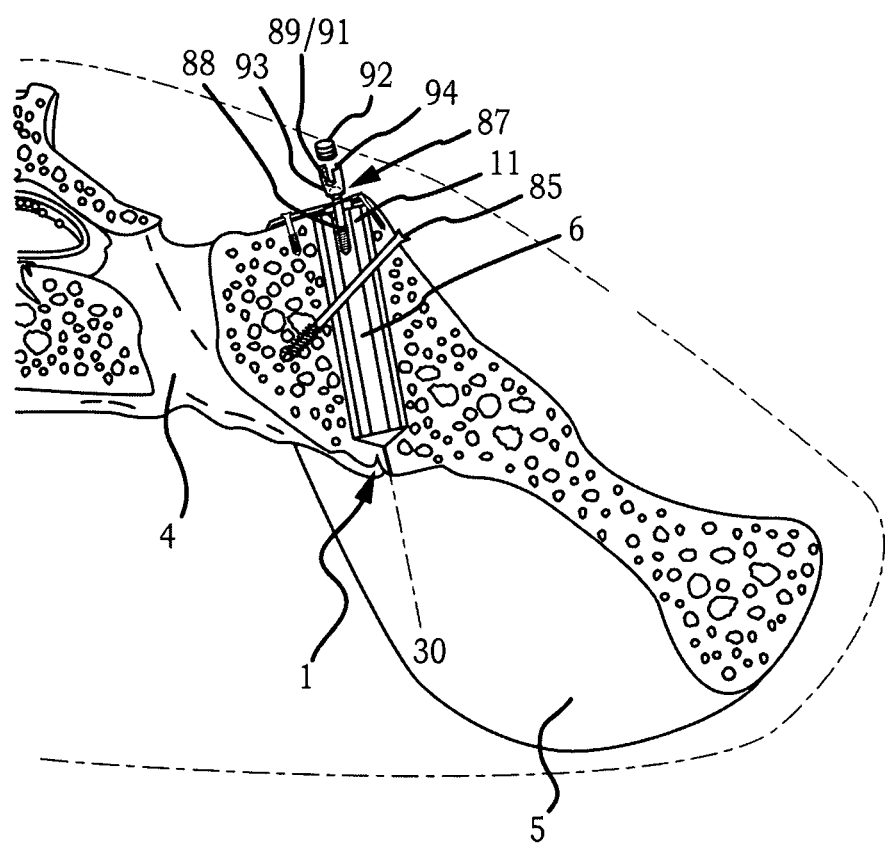

FIG. 32 is a cross section view through the sacroiliac joint which illustrates a coupling element joined to the first end of an implanted sacroiliac joint implant.

Figure 33:
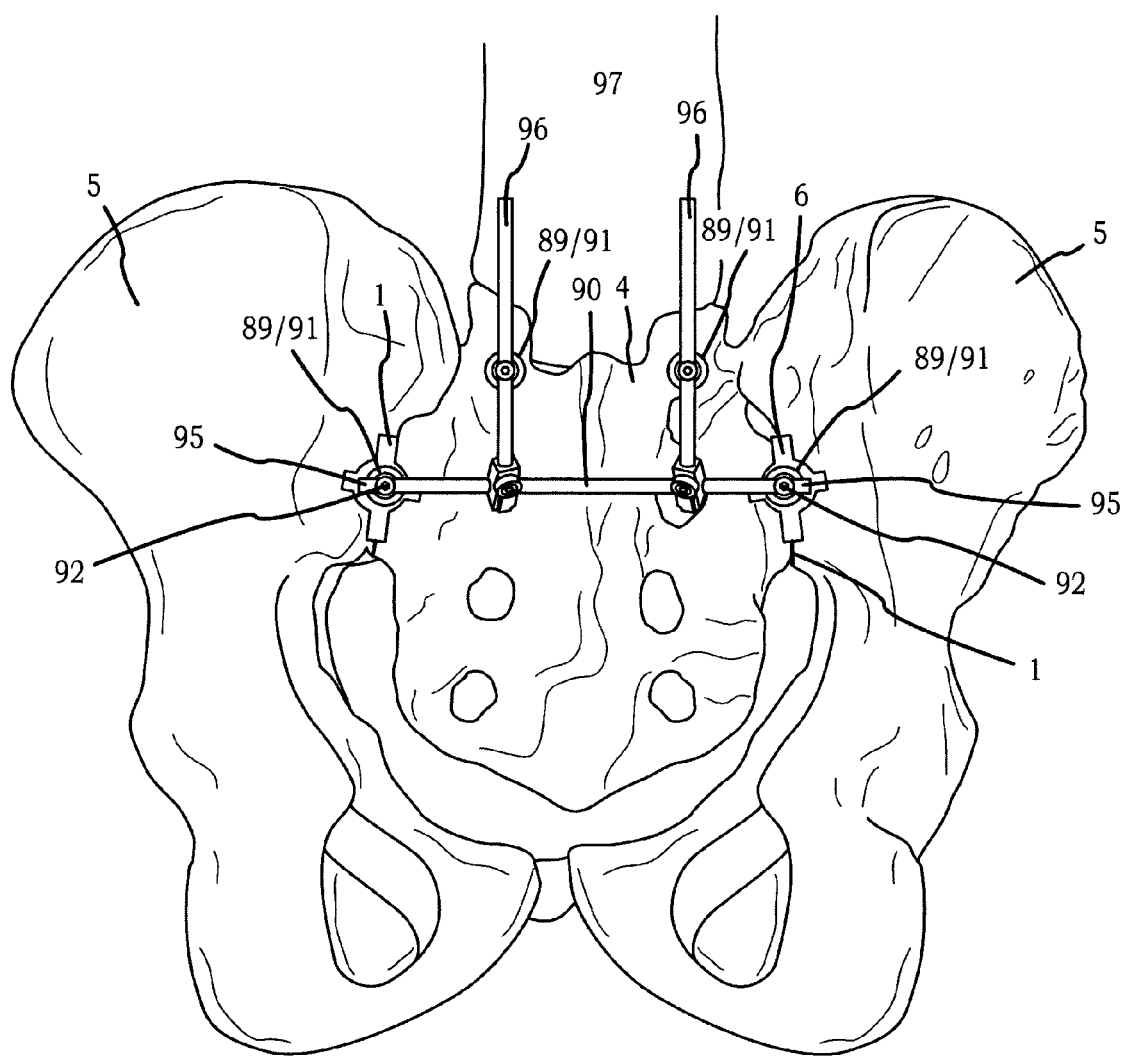

FIG. 33 is a posterior view of the pelvic region which shows a spanning member joined to a corresponding pair of coupling elements correspondingly joined to the first end of a pair of implanted sacroiliac joint implants.

Figure 34:
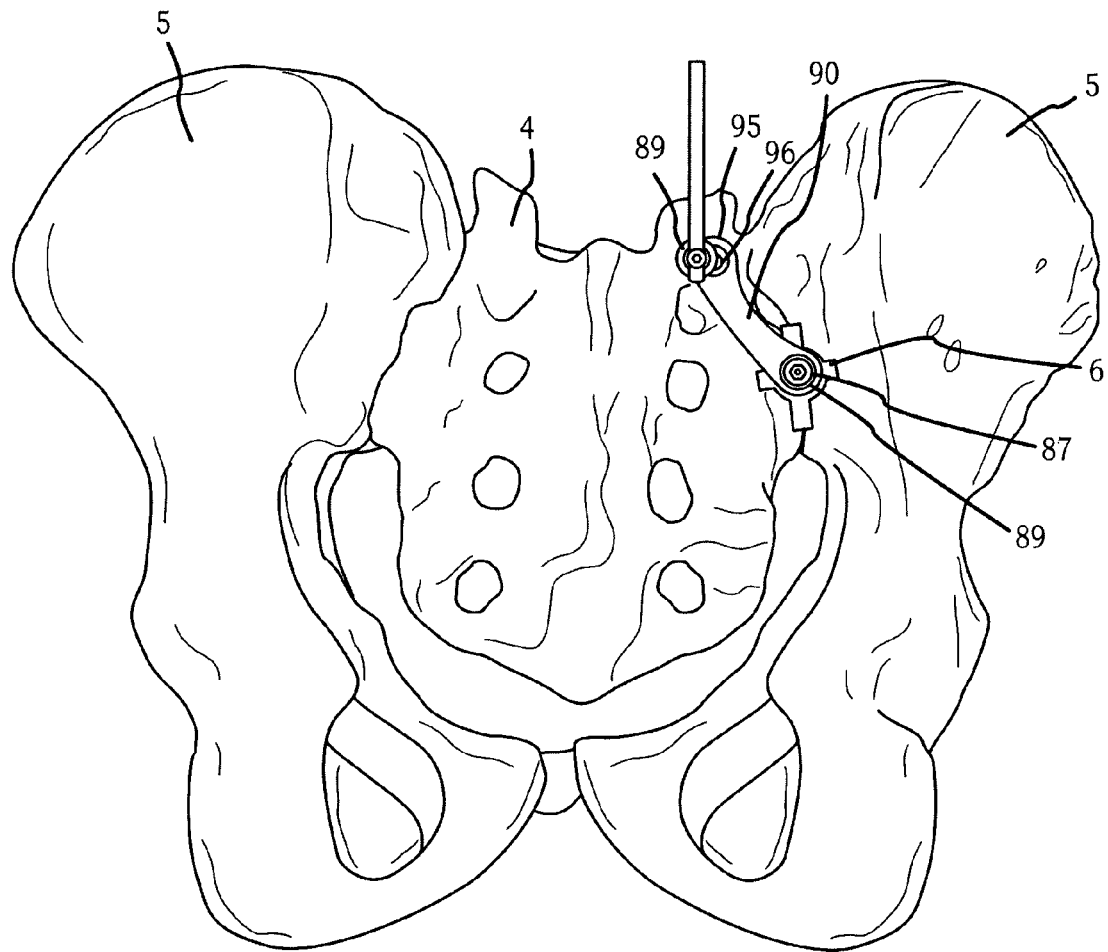

FIG. 34 is a posterior view of the pelvic region which shows a spanning member joined to a corresponding pair of coupling elements correspondingly joined to an implanted sacroiliac joint implant and directly engaged to the sacrum.

V. MODE(S) FOR CARRYING OUT THE INVENTION

Generally, a sacroiliac joint fixation fusion system that provides a method of fixation and fusion of the sacroiliac joint and a sacroiliac joint implant which upon placement within the articular region of the sacroiliac joint facilitates stability and fusion of the sacroiliac joint.

Figure 1:
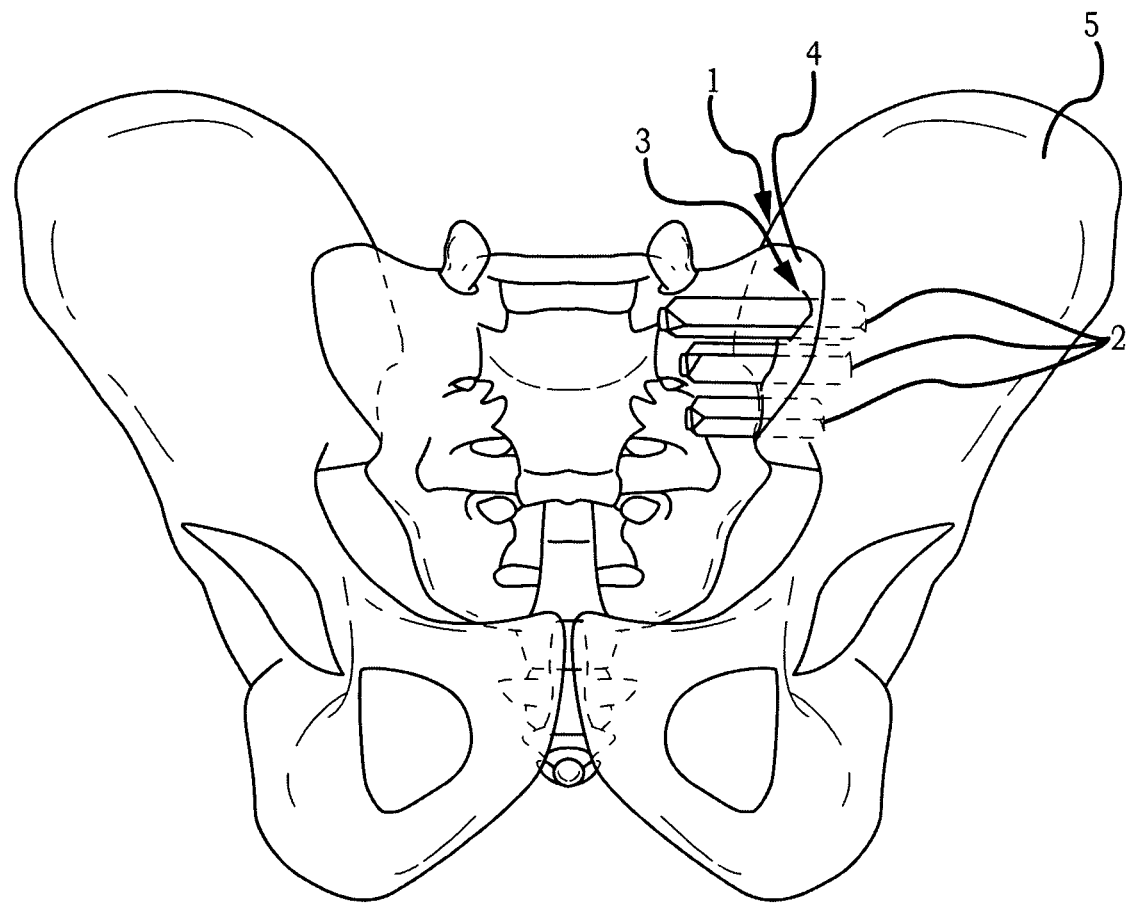
FIG. 1 is an anterior view of the pelvic region and a conventional method and device for stabilizing the sacroiliac joint.

Now referring primarily to FIG. 1 which shows one commonly utilized conventional method and device for fixation of the sacroiliac joint (1). The conventional device shown comprises one or more substantially linear elongate members (2) which can be inserted into correspondingly dimensioned trans-iliac bores (3) with a first portion extending into the bone of sacrum (4) and a second portion extending into the bone of the ilium (5), thereby extending across the sacroiliac joint (1). The one or more substantially linear elongate members (2) (which can be configured as cylindrical rods which can further include an amount of taper or further include a spiral thread coupled to the exterior surface to avoid the need for generating trans-iliac bores) in trans-iliac placement can locate the ilium (5) in fixed relation to the sacrum (4). However, this trans-iliac placement of such substantially linear elongate members (2) can have the disadvantages described above. Additionally, conventional placement of the trans-iliac bores (3) and the elongate members (2) can be outside of that region defined by the boundary of the paired articular surfaces (16)(also commonly referred to as the "auricular surfaces") of the sacroiliac joint (1), as further described below.

Now referring primarily to FIGS. 2-6, an embodiment of an inventive sacroiliac joint implant (6) is shown which in part can include an elongate body (7) which having a longitudinal axis (8). The elongate body (7) can have a configuration of sufficient dimension to avoid deformation under the normal forces of surgical placement and fixation of the ilium (5) in relation to the sacrum (4). Accordingly, while the embodiment of the sacroiliac joint implant (6) shown in FIGS. 2-6 can be generally cylindrical or circular in cross section; the invention is not so limited, and the elongate body (7) can have any of a numerous and varied configurations in cross section consistent with the method herein after described such as oval, triangular, rectangular, square, diamond, or the like. As one non-limiting example, the generally cylindrical elongate body (7) shown in FIG. 2 can depending on the application have a diameter of in the range of about 0.5 centimeters ("cm") to about 1 cm and a length disposed between a first implant end (11) and a second end (12) in the range of about 3 cm and about 6 cm.

As to particular embodiments of the invention, the elongate body (7) can further include an axial bore (9) that bounds an axial pathway (10) which communicates between a first implant end (11) and a second implant end (12) of the elongate body (7). The axial bore (9) allows for placement within the axial pathway (10) a guide pin (13) (or other guide member) about which embodiments of the sacroiliac joint implant (6) can be guided for insertion and placement in the sacroiliac joint (1), as further described below.

Again referring primarily to FIGS. 2-6, embodiments of the sacroiliac joint implant (6) can further include a first radial member (14) coupled to the external surface of the elongate body (7) extending radially outward generally along the longitudinal axis (8). As to certain embodiments of the sacroiliac joint implant (6) as shown in the Figures, the first radial member (14) can extend along the longitudinal axis (8) substantially the entire length of the elongate body (7); however, the invention is not so limited, and embodiments of the inventive sacroiliac joint implant (6) can have a first radial member

(14) which can in part or in a plurality of discontinuous parts extend along the longitudinal axis (8) or the elongate body (7).

Again referring to FIGS. 2-6, embodiments of the sacroiliac joint implant (6) can further include a second radial member (15). Each of the first radial member (14) and the second radial member (15) can extend radially outward from the elongate body (7) generally in opposed relation (about 180 degrees apart about the longitudinal axis (8) of the elongate body (7); however, the invention is not so limited, and the first radial member (14) and the second radial member (15) can be spaced about the elongate body (7) a greater or lesser number of degrees. The configuration of each of the first radial member (14) or second radial member (15)(or both) can be adapted to non-transversely locate between the articular surfaces (16) of the sacroiliac joint (1) to dispose the sacrum (4) and the ilium (5) in substantially immobilized, immobilized, or fixed relation. The term "non-transversely" as used herein means not lying or extended across the joint between the sacrum (4) and the ilium (5) and in particular does not include trans-iliac placement of a sacroiliac joint implant as above described and shown in FIG. 1. The term "articular surfaces" includes the two paired L-shaped surfaces formed between the surfaces of the sacrum (4) and the ilium (5) having a cranial portion (87) and a caudal portion (86) as shown for example in FIGS. 25, 27, and 29 (broken line) and as used herein does not include structures or regions of the sacrum (4) or the ilium (5) outside of the articular surfaces (16), such as, the paired iliac tuberosity and sacral fossa.

Each of the first radial member (14) and the second radial member (15) can each provide a pair of opposed faces (17)(18) disposed a thickness (19A) apart and having an area bound by a top edge (20), a pair of side edges (21)(22) and a bottom edge (23). The first of the pair of side edges (21) can be connected as above described to the elongate body (7) locating the second side edge (22) a distance outward from the longitudinal axis (8) of the elongate body (7). As a non-limiting example, each of the first radial member (14) and the second radial member (15) can be substantially rectangular in configuration having a height (28a) between the first of the pair of side edges (21) and the second of the pair of side edges (22) in the range of about 0.2 cm and about 1 cm. Understandably, a lesser diameter elongate body (7) may include a first radial member (14) and a second radial member (15)(or other radial members) having greater height (28a) and a greater diameter elongate body (7) may require a first radial member (14) and a second radial member (15)(or other radial members) having lesser height (28a).

Figure 2:
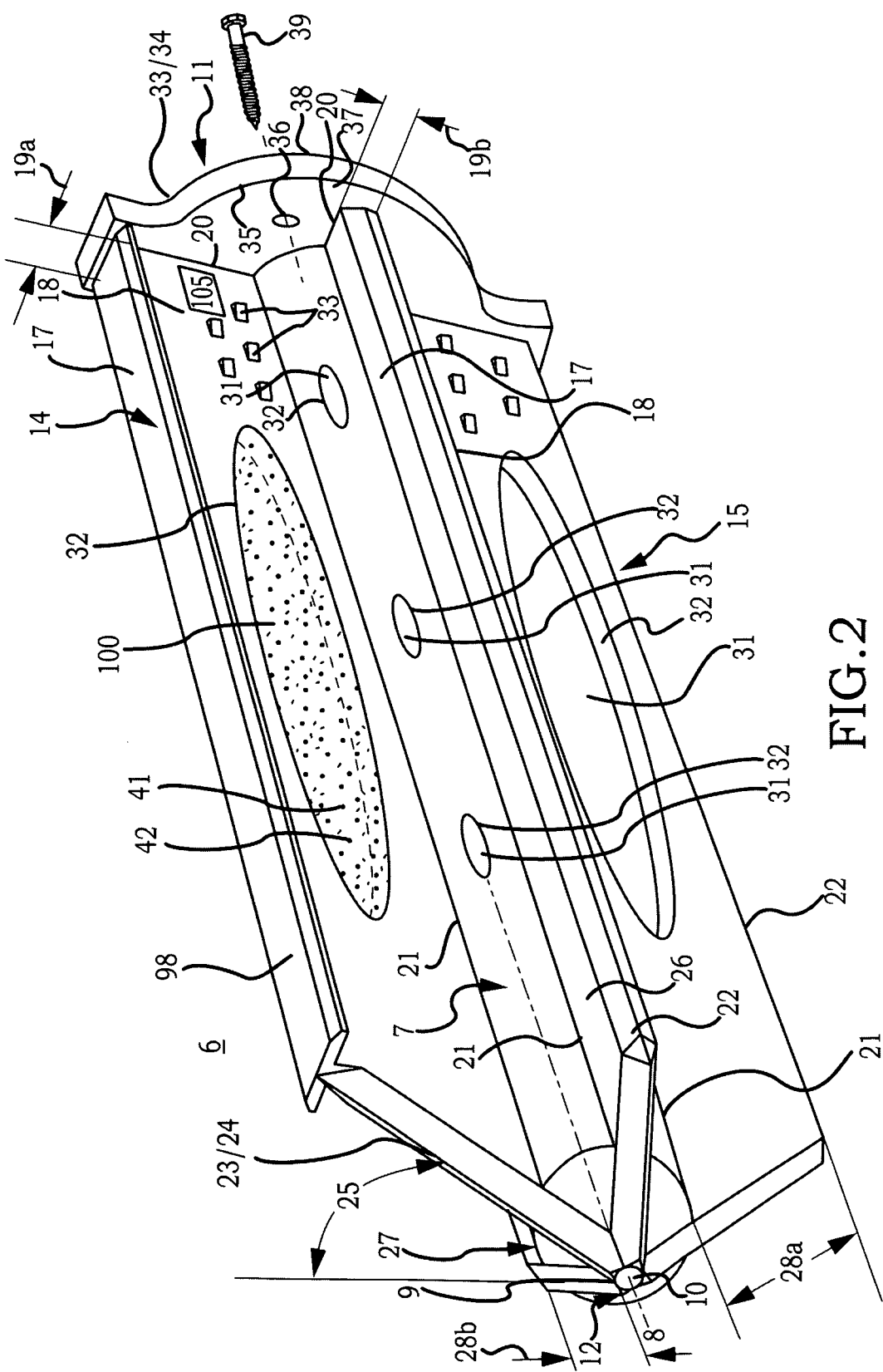
FIG. 2 is a perspective view of a particular embodiment of the sacroiliac joint implant.

The top edge (20) of each of the first radial member (14) and the second radial member (15) can terminate substantially in alignment with the first implant end (11) of the elongate body (7). The bottom edge (23) of the first radial member (14) and the second radial member (15) can terminate substantially in alignment with second implant end (12) of the elongate body (7). As to certain embodiments, the bottom edge (23) can further include an angle element (24) which angles outward from the elongate body (7) commencing at the second implant end (12) and joining the second of pair of side edges (22) a distance toward the first implant end (11). The angle element (24) can have a degree angle (25) from the perpendicular with the longitudinal axis (8) in a range of about fifteen degrees to about thirty degrees, as shown in FIG. 2; however, the invention is not so limited and the angle element (24) can be a radius element, tapered element or other element to ease insertion into the sacroiliac joint (1).

Again referring primarily to FIG. 2-6, certain embodiments of the sacroiliac joint implant (6) can further include a third radial member (26) extending along the longitudinal axis (8) of said elongate body (7) adapted to extend into the cortical bone of the ilium (5). Certain embodiments can further include a fourth radial member (27) extending along the longitudinal axis (8) of said elongate body (7) adapted to extend into the cortical bone of said sacrum (4). Certain embodiments of the third radial member (26) and the fourth radial member (27) can be adapted to extend into the bone of the sacrum (4) and the ilium (5) respectively.

As to the non-limiting embodiment of the sacroiliac joint implant (6) shown in FIG. 3, the third radial member (26) and the fourth radial member (27) can be connected generally in line with the longitudinal axis (8) of the elongate body (7). Each of the third radial member (26) and the fourth radial member (27) can extend radially outward from the elongate body (7) substantially in opposed relation (about 180 degrees apart) and in perpendicular relation (about 90 degrees) to the first radial member (14) and the second radial member (15) (see also FIGS. 8 and 9C); however, the invention is not so limited, and the third radial member (26) and the fourth radial member (27)(if the embodiment includes a fourth radial member (27)) can be spaced about the elongate body (7) in relation to each other and in relation to the first radial member (14) and the second radial member (15) a greater or lesser number of degrees depending on the application and the amount of desired engagement with the bone of the sacrum (4) or ilium (5).

The configuration of each of the third radial member (26) or the fourth radial member (27) can vary as necessary to provide an amount of surface area engagable with the bone of the sacrum (4) and ilium (5) sufficient for facilitating substantial immobilization, immobilization, or to fix, the sacrum (4) in relation to the ilium (5) upon implantation of the sacroiliac joint implant (6) and to further provide a resistance to rotation or other undesired movement of the sacroiliac joint implant (6) at the implant location within the region bounded by the articulating surfaces (16) of the sacroiliac joint (1). Accordingly, embodiments of the sacroiliac joint implant (6) having a third radial member (26) and the fourth radial member (27) can provide a pair of opposed faces (17)(18) disposed a thickness (19b) apart and have an area bound by a top edge (20), a pair of side edges (21) (22) and a bottom edge (23) in similar configuration as above described for the first radial member (14) and the second radial member (15). The first of the pair of side edges (21) can be connected as above described to the elongate body (7) locating the second side edge (22) a distance outward from the longitudinal axis (8) of the elongate body (7). As a non-limiting example, each of the third radial member (26) and the fourth radial member (27) can have a substantially rectangular configuration having a height (28b) between the first of the pair of side edges (21) and the second of the pair of side edges (22) in the range of about 0.1 cm and about 0.4 cm. The top edge (20) of each of the third radial member (26) and the fourth radial member (27) can terminate substantially in alignment with the first implant end (11) of the elongate body (7). The bottom edge (23) of the third radial member (26) and the fourth radial member (27) can terminate substantially in alignment with second implant end (12) of the elongate body (7). As to certain embodiments, the bottom edge (23) of the third radial member (26) and the fourth radial member (27) can further include the angle element (24) which angles the second of the pair of side edges (22) toward the first implant end (11) of the elongate body (7). The angle element (24) can have a degree angle (25) from the perpendicular with the longitudinal axis (8) in a range of about fifteen degrees to about thirty degrees; however, the invention is not so limited and with respect to certain embodiments of the invention there may be no angle element (24) or the angle element may be greater or less than within the range of about fifteen degrees to about thirty degrees. Additionally, the angle element (24) can be similar as shown in the figures or can be dissimilar between the radial members of a particular sacroiliac joint implant (6) depending on the application.

Again referring primarily to FIGS. 2-6, and without limitation to forgoing, the third radial member (26) and the fourth radial member (27) can have a lesser height (28*b*) than the first radial member (14) and second radial member (15). While the structure of the third radial member (26) and the fourth radial member (27) appear similar to the first radial member (14) and the second radial member (15), the function can be substantially different. The first radial member (14) and the second radial member (15) have a configuration (height, length, thickness, surface area, and location in relation to the external surface of the elongate body (7), as above described) capable of or allowing placement non-transversely between the articular surfaces (16) (and not across) or within an implant receiving space (29) surgically produced within the region bounded by the articular surfaces (16) by removal of a portion the sacroiliac joint (1), as further described below, capable upon placement between the articular surfaces (16) or within the implant receiving space (29) of substantially immobilizing or immobilizing the sacroiliac joint (1).

By contrast, the third radial member (26), and as to those embodiments having a fourth radial member (27), can have a configuration (height, length, thickness, surface area, and location on the external surface of the elongate body (7), as above described) capable of being forcibly urged a depth into the cortical bone or the cancellous bone of the sacrum (4) or the ilium (5) or placed within the radial member receiving channel (74) of the implant receiving space (29) upon non-transversely locating the sacroiliac joint implant (6) between the articular surfaces (16) of the sacroiliac joint (1). The height of the third radial member (26) and the fourth radial member (27) can be sufficient to resist rotation of the implanted sacroiliac joint implant (6) to allow boney fusion of the cancellous bone to the sacroiliac implant (6) or through apertures of the third radial member (26) or the fourth radial member (27) or both similar to the first radial member (14) and second radial member (15). Now referring primarily to FIG. 2, each radial member (14)(15)(26)(27) extending outwardly from the elongate body (7) can terminate in a radial member cross piece (98) disposed in substantially perpendicular relation to the surfaces of the radial member.

Again referring primarily to FIGS. 2-6, particular embodiments of the sacroiliac joint implant (6) can further include one or more aperture elements (31) which communicate between the opposed faces (17)(18) of the first radial member (14) or the second radial member (15) or both. The amount of open space of an aperture element (31) can be defined by an aperture perimeter (32) which can be of numerous and varied configurations of sufficient dimension to allow the surfaces of the ilium (5) or sacrum (4)(or both) adjacent to the first radial member (14) or the second radial member (15)(or both) of the sacroiliac joint implant (6) to grow a distance into the aperture element (31) or through the aperture element (31) or fuse within the aperture element (31) or fuse into material placed within the aperture element, the material can include: osseointegratable, osteoinductive, osteoconductive, osteogenic materials or biologically active agents, or combinations and permutation thereof. As a non-limiting example, the aperture perimeter (32) can be of generally oval configuration resulting in an oval aperture element (31) located in the first radial member (14) or the second radial member (15)(or both)(or located in additional radial members depending upon the embodiment) with the length of the oval aperture element (31) aligned with the length of the first radial member (14) or second radial member (15) and being about one quarter to about two thirds the length of the radial member and having a width of the oval aperture element (31) located between the sides (21)(22) of the first radial member (14) or second radial member (15) and being about one quarter to about two thirds the height (28*a*). Additionally, the elongate body (7) can further include aperture elements (31) which communicate between the external surfaces between the radial members (14)(15)(26)(27).

Figure 7:
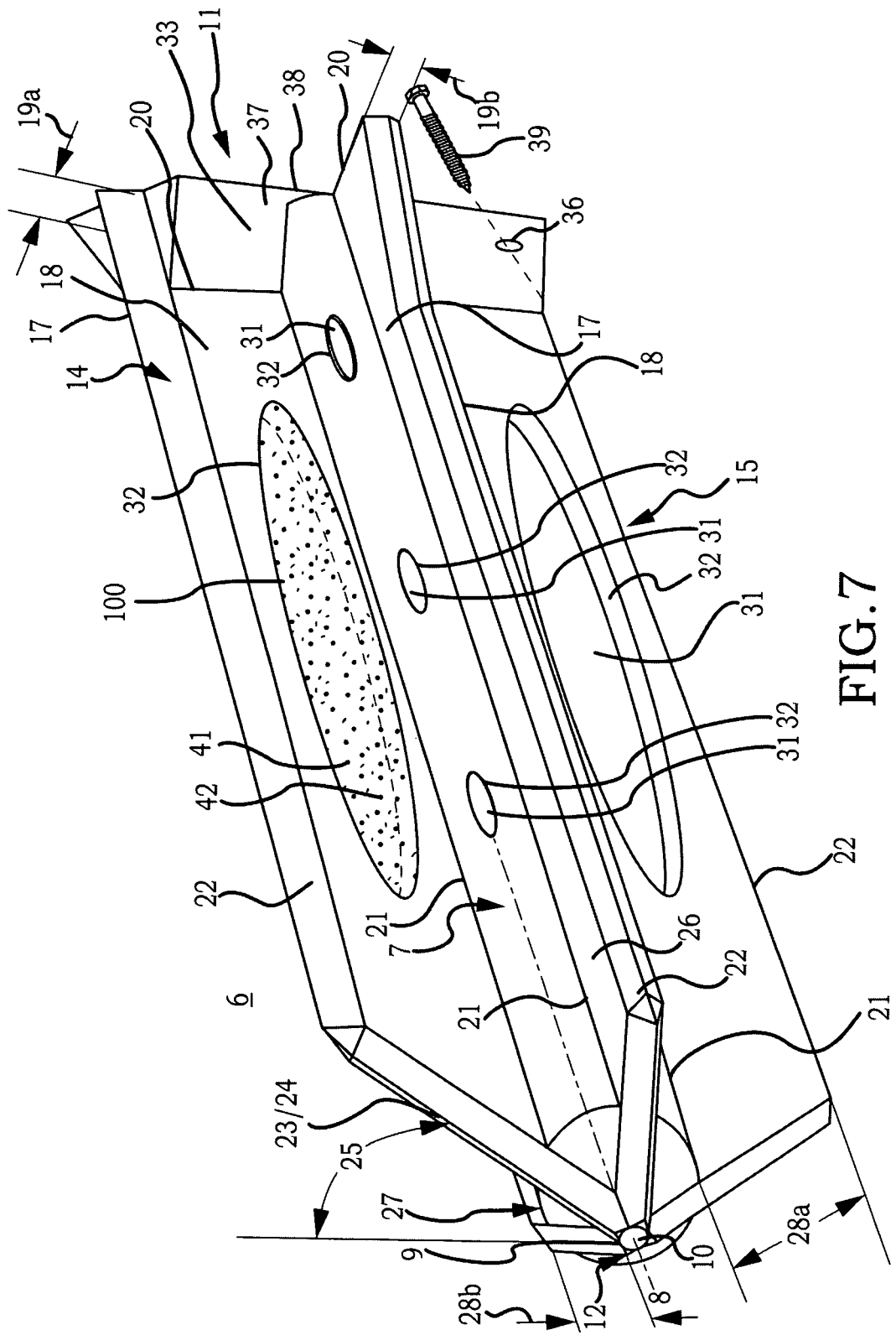
FIG. 7 is a perspective view of a second particular embodiment of the sacroiliac joint implant.

Again referring primarily to FIGS. 2-7, embodiments of the sacroiliac joint implant (6) can further include an anti-migration element (33) coupled to the first implant end (11) of the elongate body (7). The anti-migration element (33) can take the form of an enlarged terminal portion of the first end of the elongate body (7)(as shown in FIGS. 2-6), an increase in the height (28) of one or more of the radial members (such as flaring outward as shown in FIG. 7) proximate the first implant end (11) of the elongate body (7). As one non-limiting example, the anti-migration element (33) can take the form of an end cap (34) having a generally circular configuration with the center substantially aligned with the longitudinal axis (8) of the elongate member (7) and extending radially outward sufficient distance to prevent advancement of the second implant end (12) of the sacroiliac joint implant (6) further into the sacroiliac joint (1) subsequent to implantation in the implant receiving space (29). While the end cap (34) shown is generally circular in configuration, the end cap (34) can have end cap perimeter (35) which defines an oval, square, rectangle, or other configuration useful in fixing the location of the sacroiliac joint implant (6) in relation the sacroiliac joint (1). Additionally, the anti-migration element (33) can have sufficient dimensions to further include one or more bores (36) which communicate between the opposed surfaces (37)(38) of the anti-migration element (33) and dimensioned to receive mechanical fasteners (39)(such threaded members, barbed members, locking members or the like) which can be driven or rotated to engage a portion of the mechanical fastener with the sacrum (4) or the ilium (5). Now referring primarily to FIG. 2, the anti-migration element (33) can also take the form of tapered elements on a part or the entirety of the external surface which taper outward from the surface allowing insertion of embodiments of the sacroiliac joint implant (6) but opposes backward travel. Now referring primarily to FIG. 7, the anti-migration element (33) can take the form of tapered terminal end (33/99) of the sacroiliac joint implant (6) which resists forward or backward travel of the sacroiliac joint implant (6).

The elongate body (7) along with the other elements of the sacroiliac joint implant (6) above described can be fabricated or formed from a plurality of pieces or as a single piece of biocompatible material or a combination of biocompatible and biodegradable materials of suitably dimensioned particles, sheets, or other constructional forms or formable or moldable materials suitably bound or formed or molded to provide configurations in accordance with the invention.

Figure 8:
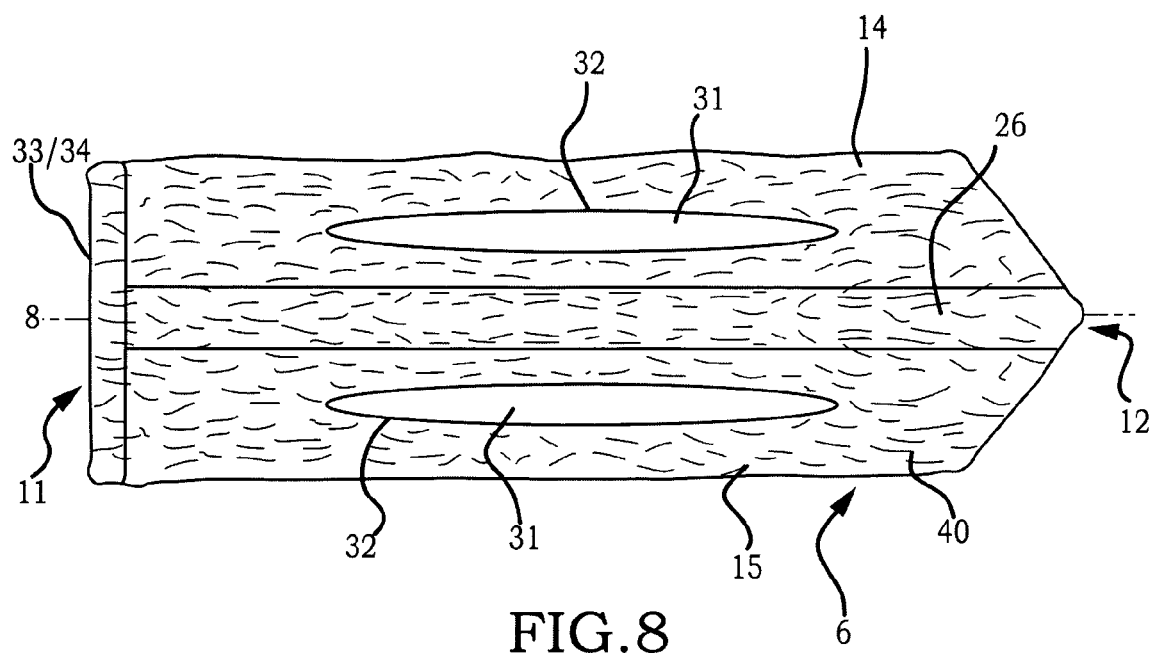
FIG. 8 is a first side view of another particular embodiment of the fixation fusion implant having a coat material which facilitates osseointegration of the fixation fusion implant with the bone.
Figure 9:
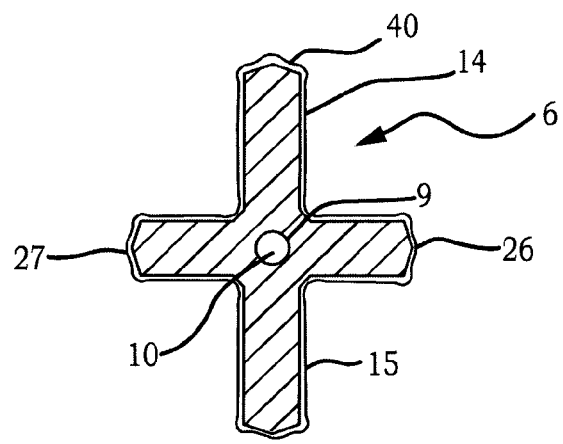
FIG. 9 is a cross section 8-8 as shown in FIG. 8 of that particular embodiment of the fixation fusion implant.
Figure 10:
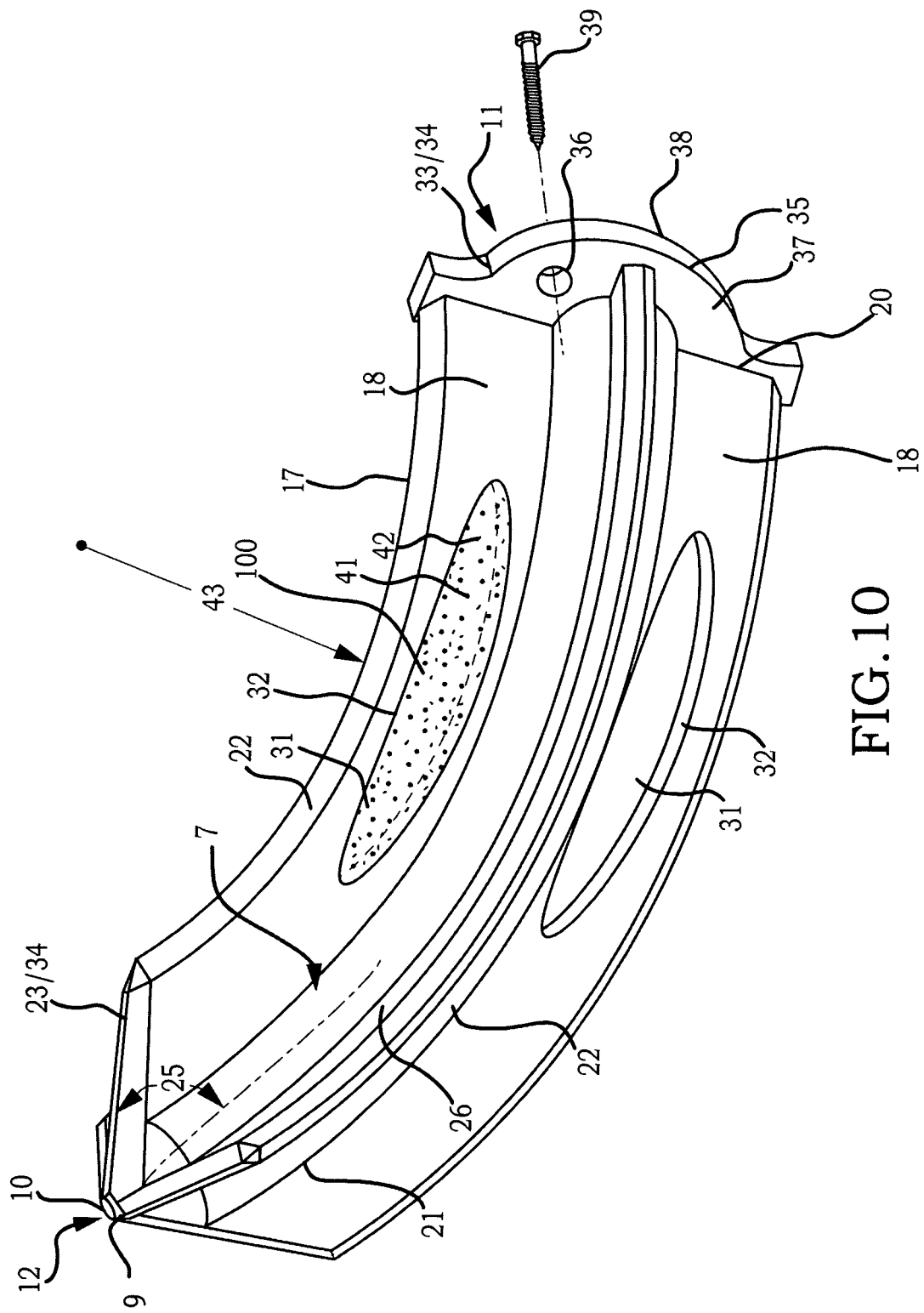
FIG. 10 is a perspective view of an embodiment of the sacroiliac joint implant having an amount of curvature along the longitudinal axis.
Figure 11:
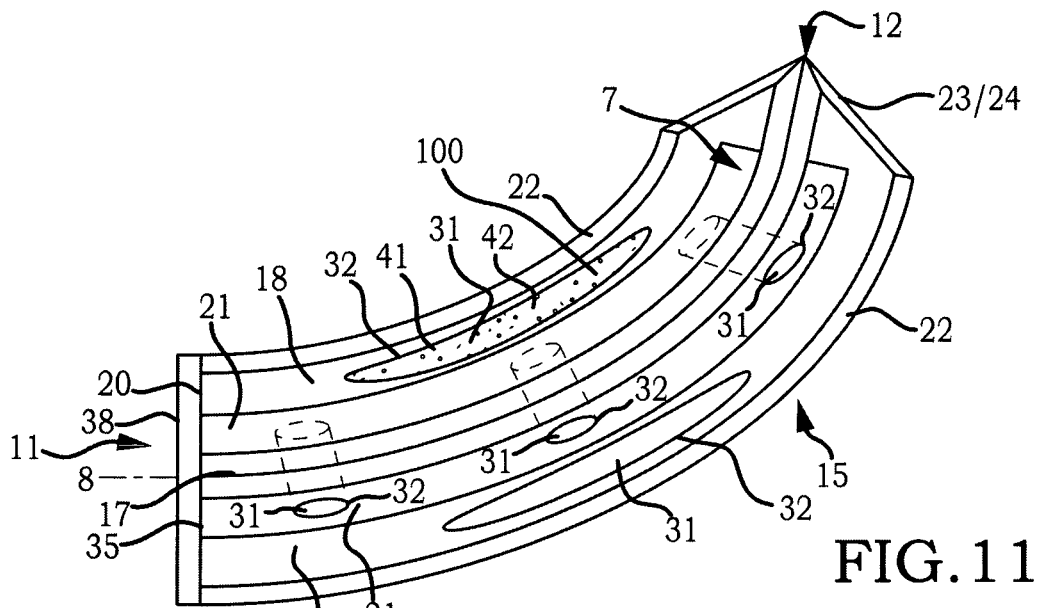
FIG. 11 is a first side view of the particular embodiment of the fixation fusion implant shown in FIG. 10.
Figures 12, 13:
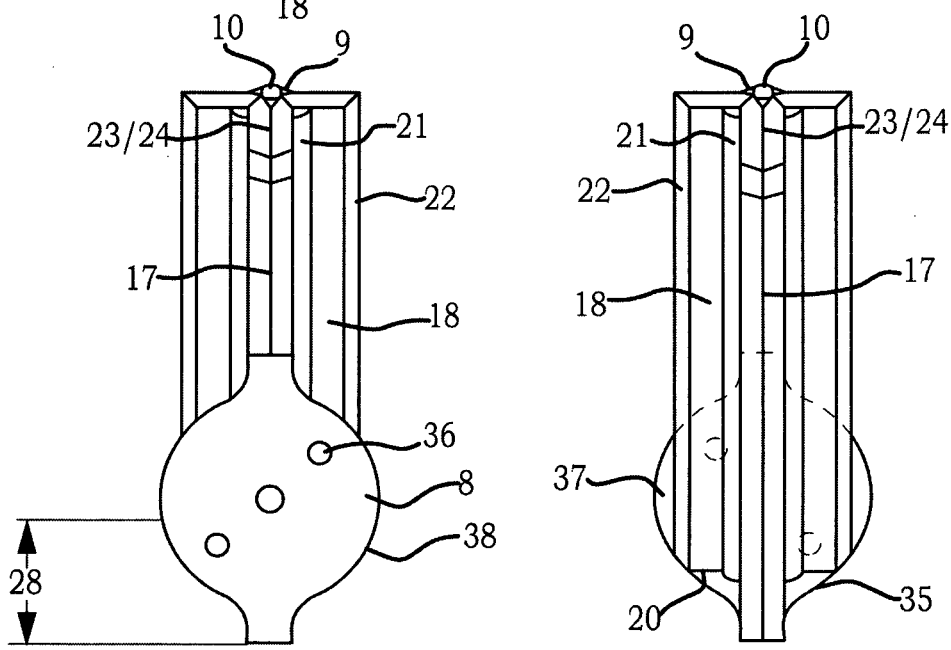
FIG. 12 is a first implant end view of a particular embodiment of the fixation fusion implant shown in FIG. 11.
FIG. 13 is a second implant end view of a particular embodiment of the fixation fusion implant shown in FIG. 11.
Figure 14:
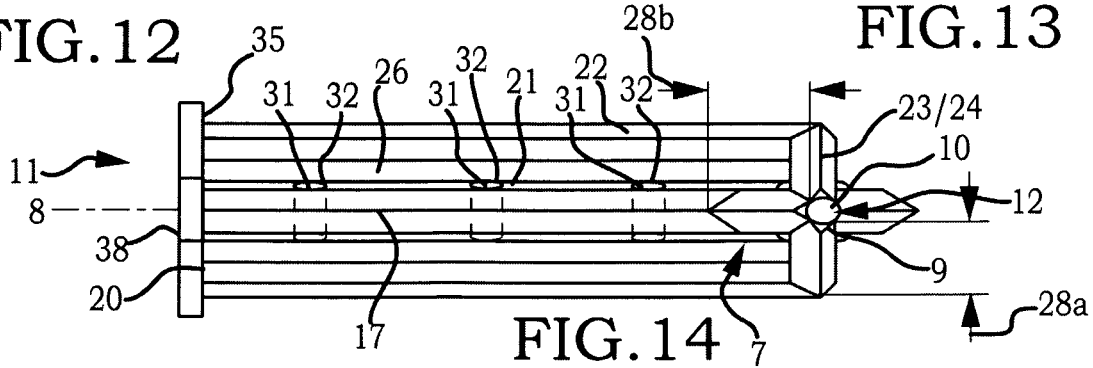
FIG. 14 is second side view of the particular embodiment of the fixation fusion implant shown in FIG. 11 rotated about 90 degrees about the longitudinal axis.

Now referring primarily to FIGS. 8 and 9, embodiments of the sacroiliac joint implant (6) can further include a coat (40) coupled, generated or integral to all or a part of the external surface of the sacroiliac joint implant (6). The coat (40) can be of any composition that can be coupled to the sacroiliac joint implant (6) capable of biocompatible osseointegration with the bone of the ilium (5) and sacrum (4), such as pure alumina, titanium-dioxide, hydroxyapatite, calcium triphosphate, or the like. As a non-limiting example, the coat (40) can be applied by plasma spraying with a plasma torch, plasmatron or a plasma gun. Alternately, the coat (40) can be achieved by producing a surface roughness, porosity, or irregularity of the sacroiliac joint implant (6) by sand blasting, bead blasting, molding, or the like. The coat (40) can have a thickness in the range of about 40 μm and about 100 μm. Again, embodiments of the sacroiliac joint implant (6) can be configured as a material having interconnecting pores throughout such as TRABECULAR METAL available from Zimmer, P.O. Box 708, 1800 West Center Street, Warsaw, Ind. 46581-0708 or a metallic foam such as a titanium foam available from the National Research Council Canada, 1200 Montreal Road, Bldg. M-58, Ottawa, Ontario, Canada or fully-engineered, porous, titanium structures such as TRABECULITE available from Tecomet, 115 Eames Street, Wilmington, Mass. 01887.

Again referring primarily to FIG. 2 and FIGS. 3-6, embodiments of the invention can further include one or more biologically active agent(s) (41) which can be applied directly to the external surface of the sacroiliac joint implant (6) or can be mixed with a biocompatible material or biocompatible biodegradable material or biocompatible osseointegratable material (collectively numeric indicator (100) which can be applied to the external surface of the sacroiliac joint implant (6) or otherwise made a part of the sacroiliac joint implant (6). As to particular embodiments of the fixation fusion implant (6), the biologically active agent(s)(41) can be mixed with an amount of a biocompatible biodegradable material or osseointegrateable material (100) and located within one or more of the aperture elements (31).

"Biocompatible" for the purposes of this invention means the ability of any material to perform the intended function of an embodiment of the invention without eliciting any undesirable local or systemic effects on the recipient and can include non-biodegradable materials such as: ceramic; metals or steels such as titanium alloys or rigid polymeric materials or rigid laminate materials or composites which include suitably dimensioned particles of metals or steels dispersed within rigid laminate materials, or suitably sized particles of biocompatible materials suitably bound or formed to provide configurations, polyurethanes, polyisobutylene, ethylene-alpha-olefin copolymers, acrylic polymers and copolymers, vinyl halide polymers and copolymers, polyvinyl esters, polyvinylidene chloride, polyacrylonitrile, polyvinyl ketones, polyvinyl aromatics such as polystyrene, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyesters, epoxy resins, rayon-triacetate, cellophane, polyether ether ketone (PEEK), polyetherketoneketone (PEKK), bone-from-wood available from the Istituto di Scienza e Tecnologia dei Mareriali Ceramici, Faenza, Italy, or the like, or biodegradable materials, as herein described.

"Biodegradable" for the purposes of this invention means the ability of any biocompatible material to breakdown within the physiological environment of the sacroiliac joint by one or more physical, chemical, or cellular processes at a rate consistent with providing treatment of a condition of the sacroiliac joint at a therapeutic level controllable by selection of a polymer or mixture of polymers (also referred to as polymeric materials), including, but not limited to: polylactide polymers (PLA), copolymers of lactic and glycolic acids (PLGA), polylactic acid-polyethylene oxide copolymers, poly(ε-caprolactone-co-L-lactic acid (PCL-LA), glycine/PLA copolymers, PLA copolymers involving polyethylene oxides (PEO), acetylated polyvinyl alcohol (PVA)/polycaprolactone copolymers, hydroxybutyrate-hydroxyvalerate copolymers, polyesters such as, but not limited to, aspartic acid and different aliphatic diols, poly(alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA), aliphatic-aromatic homopolymers, and poly(anhydride-co-imides), poly (phosphoesters) by matrix or pendant delivery systems, poly (phosphazenes), poly(iminocarbonate), crosslinked poly (ortho ester), hydroxylated polyester-urethanes, or the like.

"Biologically active agents" for the purposes of this invention means those agents or mixture of agents which can be varied in kind or amount to provide a therapeutic level effective to mediate the formation or healing of bone, cartilage, tendon, or to reduce, inhibit, or prevent a symptom of a condition of the sacroiliac joint subsequent to placement of an embodiment of the fixation fusion implant within the sacroiliac joint (1) such as infection or pain and without limitation can include agents that influence the growth of bone, demineralized bone matrix, stem cells, alleografts, autografts, xenografts, bone forming protein whether naturally occurring, synthetic, or recombinate, growth factors, cytokines, bone morphogenetic protein 2, bone morphogenetic protein 7, analgesics, anesthetics, anti-inflammatory agents, antibacterials, antivirals, antifungals, antiprotozoals, anti-infectives, antibiotics such as aminoglycosides such as gentamicin, kanamycin, neomycin, and vancomycin; amphenicols such as chloramphenicol; cephalosporins, such as cefazolin HCl; penicillins such as ampicillin, penicillin, carbenicillin, oxycillin, methicillin; lincosamides such as lincomycin; polypeptide antibiotics such as polymixin and bacitracin; tetracyclines such as tetracycline, minocycline, and doxycycline; quinolones such as ciprofloxacin, moxifloxacin, gatifloxacin, and levofloxacin; anti-viral drugs such as acyclovir, gancyclovir, vidarabine, azidothymidine, dideoxyinosine, dideoxycytosine; analgesics, such as codeine, morphine, ketorolac, naproxen, an anesthetic, lidocaine; cannabinoids; antifungal agents such as amphotericin; anti-angiogenesis compounds such as anecortave acetate; retinoids such as tazarotene, steroidal anti-inflammatory agents such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide; or allograft cellular matrix containing viable mesenchymal stem cells such as OSTEOCEL PLUS available from NuVasive, Inc., 7475 Lusk Blvd., San Diego, Calif. 92121 USA, and any of their derivatives, whether separately or in combinations thereof.

As to particular embodiments of the inventive fixation fusion implant (6) the biologically active agent(s)(41) can be dispersed throughout a biocompatible or biocompatible biodegradable material (or mixture of biocompatible materials or mixture of biocompatible biodegradable materials) by mixing biologically active agent(s)(41) into the melted biocompatible or biodegradable polymer and then solidifying the resulting material by cooling, having the biologically active agent(s)(41) substantially uniformly dispersed throughout. The biodegradable material or biocompatible material or mixture thereof can be selected to have a melting point that is below the temperature at which the biologically active agent(s)(41) becomes reactive or degrades. Alternatively, the biologically active agent(s)(41) can be dispersed throughout the biocompatible or biodegradable material by solvent casting, in which the biocompatible or biodegradable material is dissolved in a solvent, and the biologically active agent(s)(41) dissolved or dispersed in the solution. The solvent is then evaporated, leaving the biologically active agent(s)(41) in the matrix of the biocompatible or biodegradable material. Solvent casting requires that the biocompatible or biodegradable material be soluble in organic solvents. Alternatively, the fixation fusion implant (6) can be placed in a solvent having a concentration of the biologically active agent(s)(41) dissolved and in which the fixation fusion implant (6) or the biocompatible or biocompatible biodegradable material located in the aperture elements, or applied to the external surface, swells. Swelling of the fixation fusion implant (6) or portions thereof draws in an amount of the biologically active agent(s) (41). The solvent can then be evaporated leaving the biologically active agent(s)(41) within the biocompatible or biocompatible biodegradable material. As to each method of dispersing the biologically active agent(s) (41) through out the biocompatible or biodegradable biocompatible material of or coupled to the fixation fusion implant (6), therapeutic levels of biologically active agent(s) (41) can be included in biocompatible biodegradable material to provide therapeutically effective levels of the biologically active agent to the sacroiliac joint (1) to treat a particular sacroiliac joint condition.

Other non-active agents (42) may be included in the biocompatible biodegradable material for a variety of purposes. For example, buffering agents and preservatives may be employed. Preservatives which may be used include, but are not limited to, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. Examples of buffering agents that may be employed include, but are not limited to, sodium carbonate, sodium borate, sodium phosphate, sodium acetate, sodium bicarbonate, and the like, as approved by the FDA or other appropriate agencies in the United States or foreign countries, for the desired route of administration. Electrolytes such as sodium chloride and potassium chloride may also be included in the formulation.

A non-limiting example, embodiments of the fixation fusion implant (6) having a biocompatible biodegradable portion with biologically active agent(s)(41) for treating the sacroiliac joint (1) can be made by dispersing a biologically active agent(s)(41) in a biocompatible biodegradable material as above described to provide biologically active agent(s) (41) release characteristics at a therapeutic level. Upon implantation of the fixation fusion implant (6) in the sacroiliac joint (1) as described below, the biocompatible biodegradable portion of the fixation fusion implant (6) can substantially continuously release biologically active agent (41) to provide a localized amount of bone morphogenetic protein 2 at therapeutic levels of about 1 milligram to about 4 milligrams to facilitate bone regrowth. It is to be understood that this specific example of providing an embodiment of the fixation fusion implant (6) which delivers an amount of bone morphogenetic protein 2 to facilitate bone regrowth, is not intended to be limiting, and embodiments of the fixation fusion implant (6) can be utilized to deliver numerous and varied active agent(s)(41) individually or in combination to treat a wide range of conditions of the sacroiliac joint (1) subsequent to implantation of embodiments of the fixation fusion implant (6).

Now referring primarily to FIGS. 10-15 and 30, particular embodiments of the invention can further include an amount of curvature (43) between the first implant end (11) and the second implant end (12) of the fixation fusion implant (6). The amount of curvature (43) can vary from embodiment to embodiment of the fixation fusion implant (6) depending on the application between a substantially linear elongate body (7) as above described to including an amount of curvature (43) which defines a radius to facilitate placement in the cranial portion (87) and a caudal portion (86) between the articular surfaces (16) of the sacroiliac joint (1) or in the corresponding implant receiving space (29). As one non-limiting embodiment the radius can be within a range of about 2 cm and about 6 cm.

Figure 15:
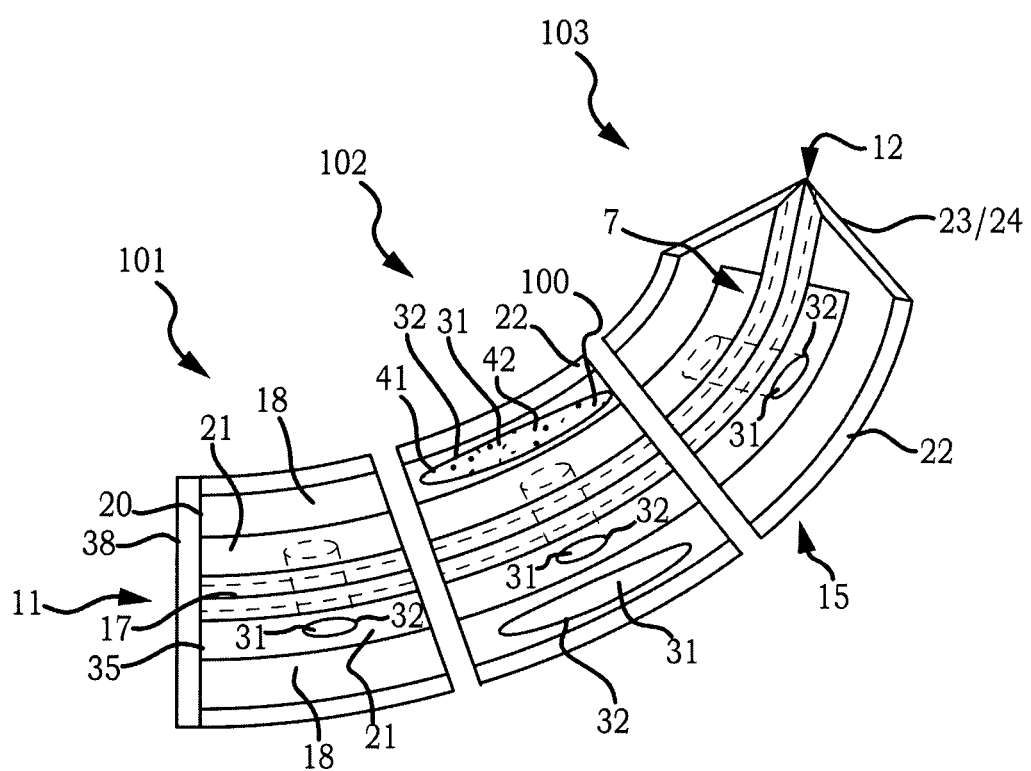
FIG. 15 is a side view of the embodiment of the sacroiliac joint implant shown in FIG. 10 produced in a plurality of implantable parts.

Now referring primarily to FIG. 15, certain embodiments of the invention having an amount of curvature can be provided in a plurality of implant segments (101)(102)(103) which can be individually implanted within the articular region (44) as shown in FIG. 25, 27, or 29 by the method below described.

Additionally, embodiments of the sacroiliac joint implant (6) can be configured to house a bone growth stimulator (105). Useful implantable growth stimulators can directly engage the anode of a battery and a single or double titanium cathode wire implanted within or in close proximity to the sacroiliac joint implant (6). The cathode wire can be disposed a distance into the host bone, bone graft, or portions of the device, preferably with the cathode ends contacting and or anchored into living bone. Embodiments of the invention can include a metal implant with an insulation material, such as PEEK, to prevent cathode-metal contact, while permitting cathode-bone contact. The battery can be placed in an extrafascial, subcutaneous pocket for removable placement. A suitable growth stimulator is available from Biomet Trauma 100 Interpace Pkwy #1, Parsippany, N.J. 07054-1149.

Understandably, a plurality of inventive sacroiliac joint implants (6) whether separately or in joined relation, whether the same or different embodiments, can be utilized with conventional or the inventive methods of implantation herein described for fixation and fusion of the sacroiliac joint (1). As one example, a plurality of elongate bodies (7) can be joined in fixed, substantially fixed or movable relation to provide an embodiment of the sacroiliac joint implant (6).

Now referring primarily to FIGS. 16-24, a non-limiting method of accessing an articular region (44) between the articulating surfaces (16) of the sacroiliac joint (1) and placing a sacroiliac joint implant (6) non-transversely between the articulating surfaces (16) within the articular region (44) of the sacroiliac joint (1) to dispose the sacrum (4) and the ilium (5) in substantially immobilized relation by corresponding engagement of the sacroiliac joint implant (6) by the articulating surfaces (16) of the sacroiliac joint (1). The particular example of the method described is sufficient to enable a person of ordinary skill in the art to utilize embodiments of the sacroiliac joint implant (6) and is not intended to be limiting with respect to the order of steps or the use of all or any of the steps or combination of one or more steps into one steps or performing any one step as substeps, or other similar, equivalent, or conventional steps to implant embodiments of the sacroiliac joint implant within the sacroiliac joint (1).

Figure 16:
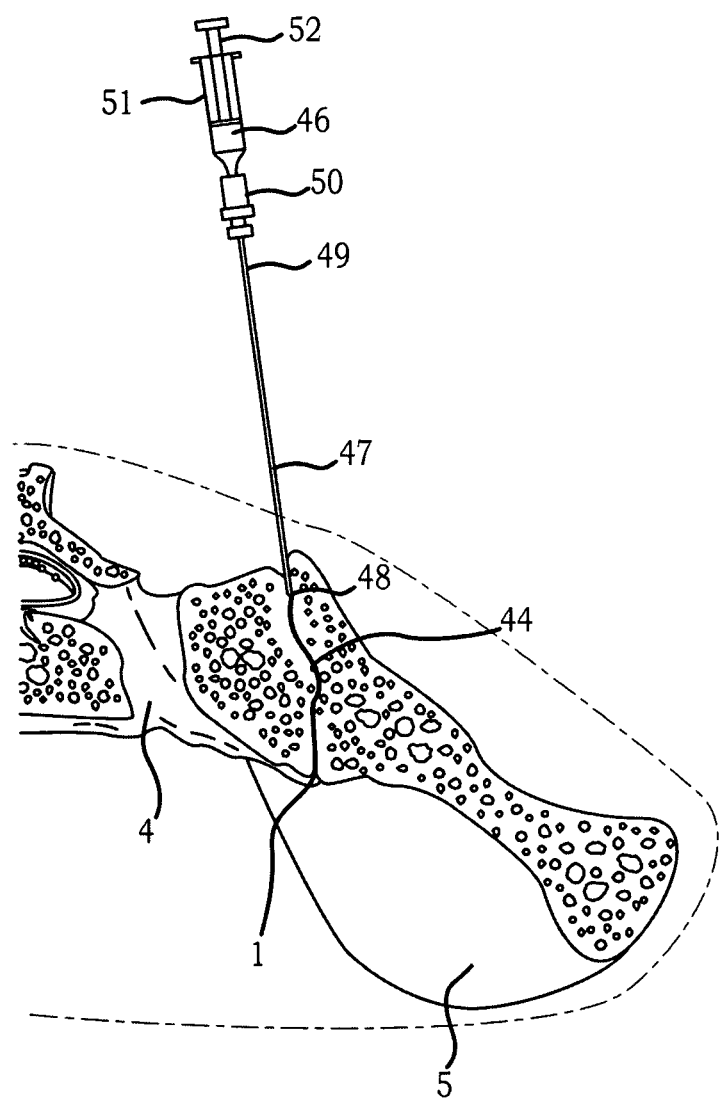
FIG. 16 is a cross section view through the sacroiliac joint which illustrates a method of implanting an embodiment of the sacroiliac joint implant the step including insertion of a needle into the articular plane of the sacroiliac joint to inject a radiographic dye to allow fluoroscopic visualization of the sacroiliac joint.

Now referring primarily to FIG. 16, an embodiment of the method can include the step of placing a patient under sedation prone on a translucent operating table (or other suitable surface). The sacroiliac joint (1) can be locally anesthetized to allow for injecting a radiographic contrast (46) (as a non-limiting example, Isoview 300 radiographic contrast) under fluoroscopic guidance into the inferior aspect of the sacroiliac joint (1) to outline the articular surfaces (16) of the sacroiliac joint (1). Injection of the radiographic contrast (46) within the sacroiliac joint (1) can be accomplished utilizing a tubular member (47) (such as a syringe needle) having first tubular member end (48) which can be advanced between the articulating surfaces (16) of the sacroiliac joint (1) and having a second tubular member end (49) which removably couples to a hub (50). The hub (50) can be configured to removably couple to a syringe barrel (51) (or other device to contain and deliver an amount of radiographic contrast (46)). In the example of a syringe barrel (51), the syringe barrel (51) can have an internal volume capable of receiving an amount of the radiographic contrast (46) sufficient for outlining the lateral articular surfaces (16) of the sacroiliac joint (1). A plunger (52) can be slidingly received within the barrel (51) to deliver the radiographic contrast (46) through the tubular member (47) into the sacroiliac joint (1). The tubular member (47) can have a gauge in the range of about 16 gauge and about 20 gauge and can further be incrementally marked on the external surface to allow determination of the depth at which the first needle end (48) has advanced within the sacroiliac joint (1). As the first needle end (48) advances into the sacroiliac joint (1) the radiographic dye (46) can be delivered from within the syringe barrel (51) into the sacroiliac joint (1) to allow visualization of the sacroiliac joint (1) and location of the tubular needle (47) within the sacroiliac joint (1).

Figure 17:
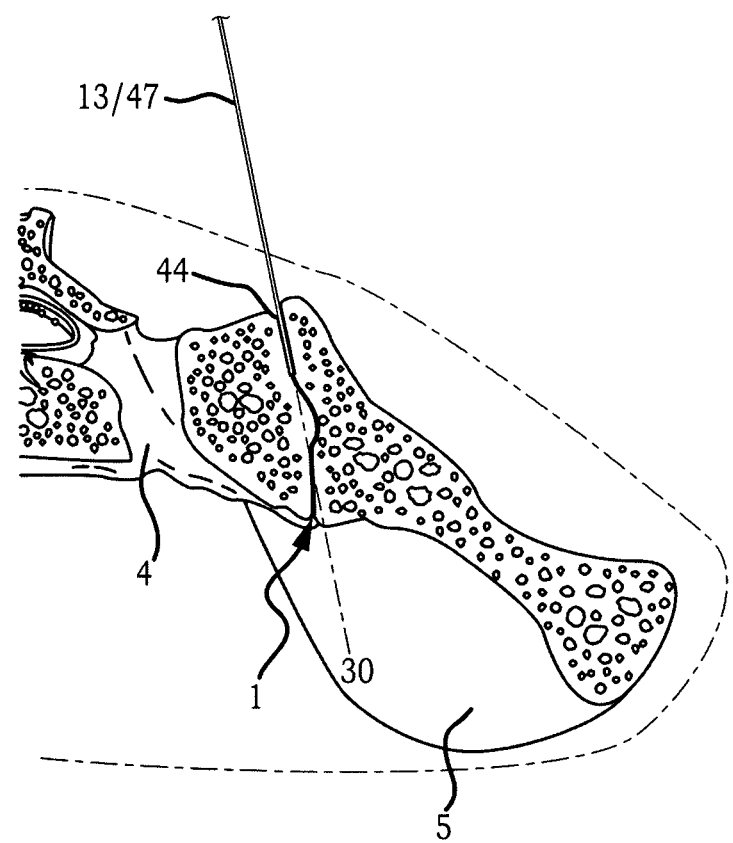
FIG. 17 is a cross section view through the sacroiliac joint which illustrates a method of implanting an embodiment of the sacroiliac joint implant the step including fixing the tubular needle within the sacroiliac joint as a guide wire.

Now referring primarily to FIG. 17, once the first tubular member end (48) has been sufficiently advanced into the sacroiliac joint (1) and the articular surfaces (16) of the sacroiliac joint (1) have been sufficiently visualized, the hub (50) can be removed from the tubular member (47) leaving the tubular member (47) fixed within the sacroiliac joint (1) as a initial guide for tools subsequently used to locate or place the sacroiliac joint implant (6) non-transversely between the articulating surfaces (16) of the sacroiliac joint (1) or in removal of a portion of the sacroiliac joint (1) within the region defined by the articular surfaces (16) to generate an implant receiving space (29). Alternately, one or more guide pins (13) can be inserted along substantially the same path of the tubular member (47) for fixed engagement within the sacroiliac joint (1) and used in subsequent steps as a guide(s).

Figure 18:
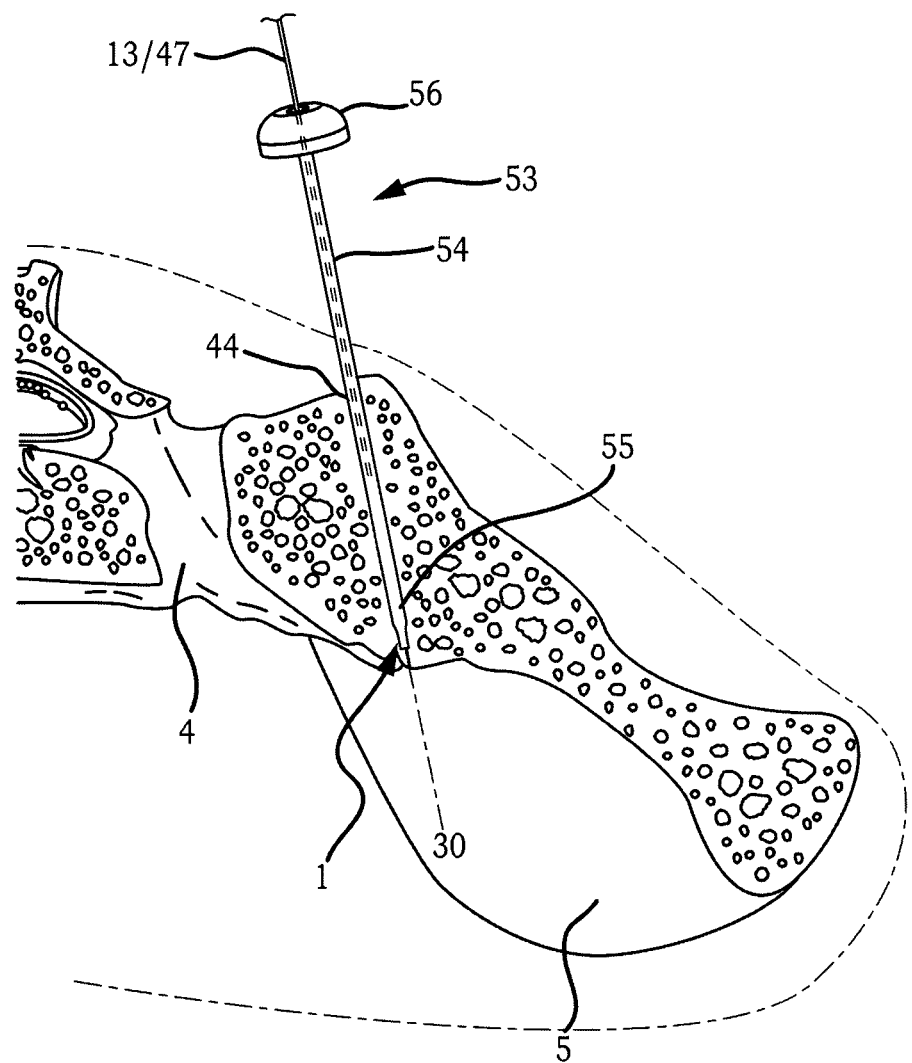
FIG. 18 is a cross section view through the sacroiliac joint which illustrates a method of implanting an embodiment of the sacroiliac joint implant the step including advancing a body of a cannulated probe along the needle fixed in the sacroiliac joint to fixed location at the anterior portion of the sacroiliac joint.

Now referring primarily to FIG. 18, a small incision can be made in the skin at the posterior superior (or as to certain embodiments inferior) aspect of the sacroiliac joint (1), extending proximal and distal to the tubular member (47) along the line of the sacroiliac joint (1) to provide a passage to access the interarticular space between the articulating surfaces (16) of the sacroiliac joint (1). A cannulated probe (53) can be slidingly engaged with the tubular member (47) (or guide pin (13)) extending outwardly from the sacroiliac joint (1) (while the sacroiliac joint may be shown in the figures as being substantially linear for illustrative purposes, it is to be understood that the normal irregular features of the sacroiliac joint have not been removed). The cannulated probe (53) can have a probe body (54) of generally cylindrical shape terminating in a spatulate tip (55) at the end advanced into the sacroiliac joint (1). A removable cannulated probe handle (56) couples to the opposed end of the probe body (54). The spatulate tip (55) can be guided along the tubular needle (47) (or guide wire (13)) into the posterior portion of the sacroiliac joint (1) and advanced to the anterior portion of the sacroiliac joint (1) under lateral fluoroscopic visualization. The cannulated probe handle (56) can then be removed providing the generally cylindrical probe body (54) extending outwardly from the sacroiliac joint (1) through the incision made in the skin.

Figure 19:
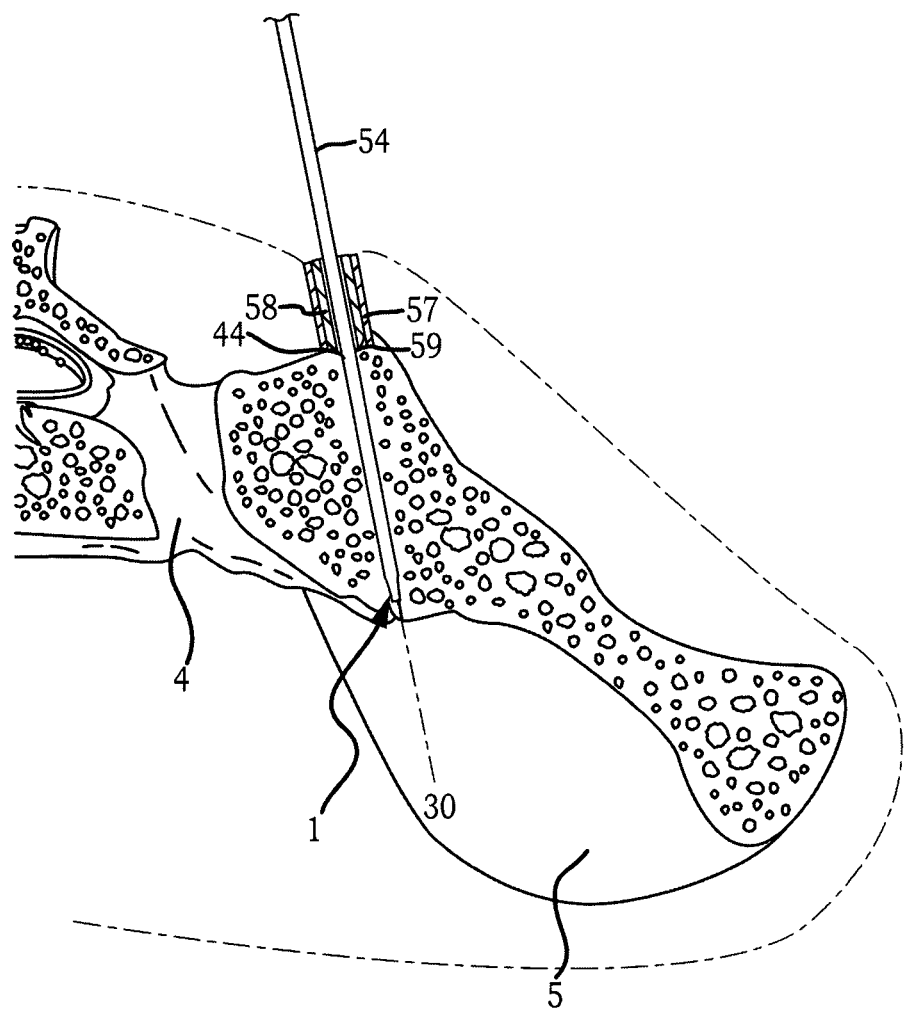
FIG. 19 is a cross section view through the sacroiliac joint which illustrates a method of implanting an embodiment of the sacroiliac joint implant the step including advancing an tissue dialator along the body of the cannulated probe fixed in the sacroiliac joint to allow placement of a cannula against the surface of the sacrum and ilium to expose the sacroiliac joint.

Now referring primarily to FIG. 19, a passage from the incision to the sacroiliac joint (1) can be generated by inserting a cannula (57) into the incision. A soft tissue dilator (58) having a blunt end (59) can be advanced over the probe body (54), or a plurality of soft tissue dilators of increasing size, until the blunt end (59) of the soft tissue dilator (58) and the corresponding cannula end (45) contact the posterior aspect of the sacroiliac joint (1). The soft tissue dilator (58) can be removed from within the cannula (57). The external surface of the cannula (57) can be sufficiently engaged with the surrounding tissue to avoid having the tissue locate with in the hollow inside of the cannula (57). A non-limiting embodiment of the cannula (57) provides a tubular body having substantially parallel opposed side walls which terminate in a radius at both ends (lozenge shape) into which a plurality of different jigs can be inserted.

Figure 20A:
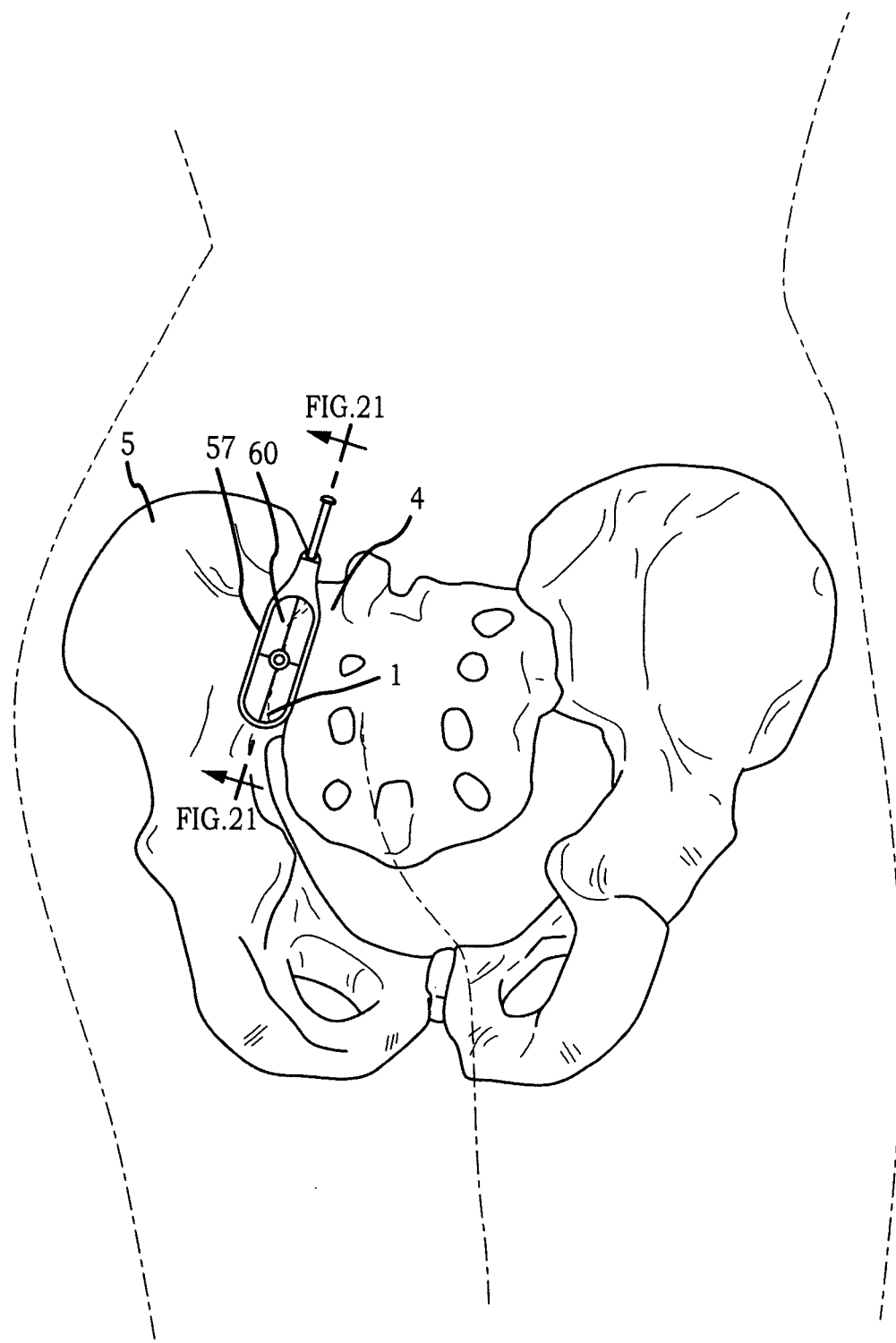
FIG. 20A is a posterior view of the pelvic region showing fixed placement of the cannula in relation to the sacroiliac joint having inserted within a cannula alignment jig.
Figure 20B:
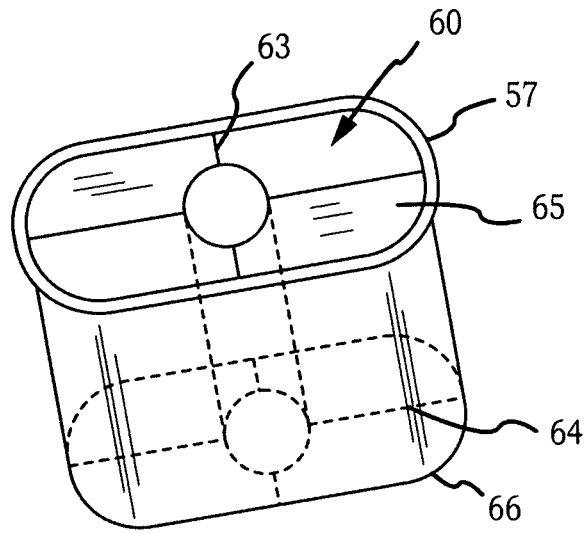
FIG. 20B is a perspective view of the cannula jig insert shown in FIG. 20A having cross hairs.
Figure 20C:
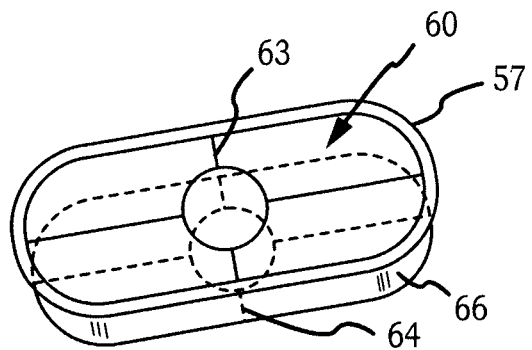
FIG. 20C is a perspective view of the cannula shown in FIG. 20B having a cannula alignment jig inserted within having alignable cross hairs.

Now referring primarily to FIG. 20A-20C, a cannula alignment jig (60) can be advanced over the probe body (54) (or guide pins (13)) and received within the cannula (57). Substantially, identical cross hairs (63)(64) can be disposed on the upper jig surface (65) and the lower jig surface (66). Alignment of the cross hairs (63)(64) under x-ray with the sacroiliac joint (1) can confirm that the cannula (57) has proper orientation in relation to the paired articular surfaces (16) of the sacroiliac joint (1). The cannula (57) properly oriented with the paired articular surfaces (16) can than be disposed in fixed relation to the sacroiliac joint by placement of fasteners through the cannula (57) into the sacrum (4) or the ilium (5).

Figure 21A:
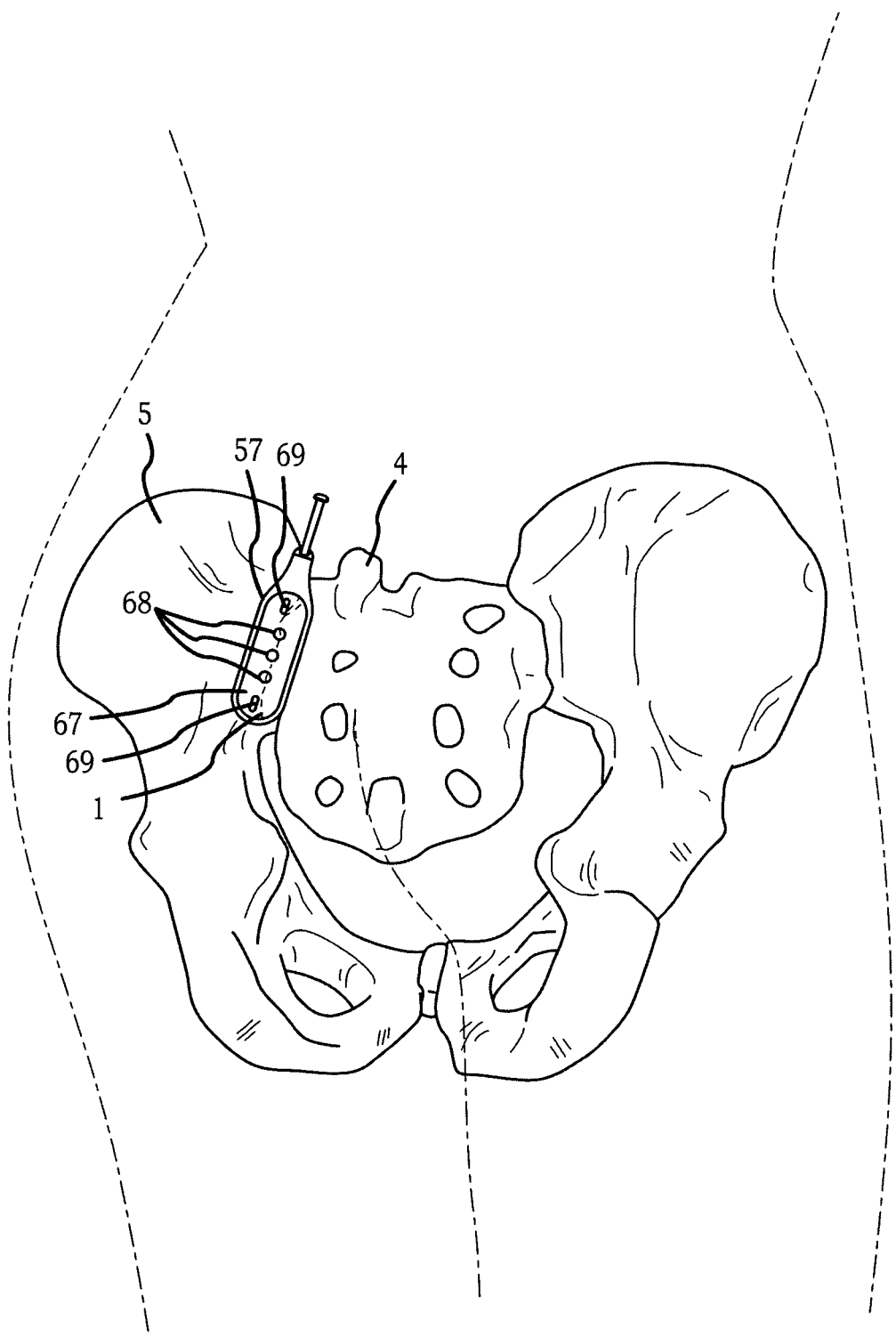
FIG. 21A is a posterior view of the pelvic region showing fixed placement of the cannula in relation to the sacroiliac joint having within a first drill jig.
Figure 21B:
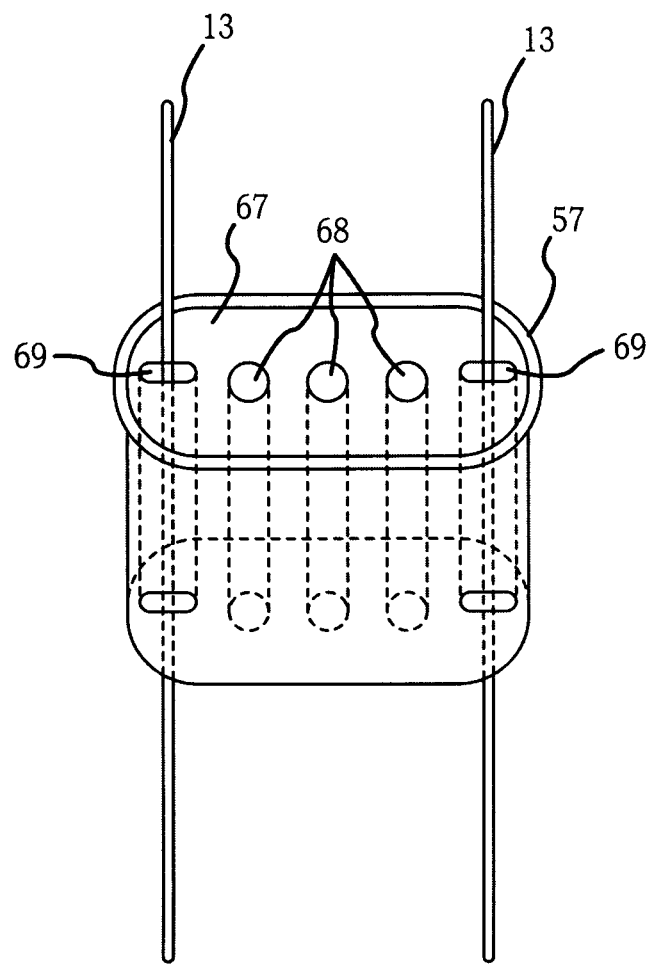
FIG. 21B is a perspective view of the cannula of FIG. 21A having within the first drill jig.

Now referring to FIGS. 21A and 21B, a first drill jig (67) can be advanced over the probe body (54) (or guide pins (13)) and received within the cannula (57). The probe body (54) (or guide pins (13)) extending outwardly from the sacroiliac joint (1) passes through a drill guide hole (68) of the first drill jig (67) (or a plurality of guide pins (13) can extend through a corresponding plurality of guide pin holes (69)). The drill guide hole (68) can take the form of a circular hole as shown in the Figures, a slot, or other configuration to restrict the movement of the drill bit (62) within the drill jig (60) and provide a guide for a drill bit (62) in relation to the sacroiliac joint (1).

Figure 22:
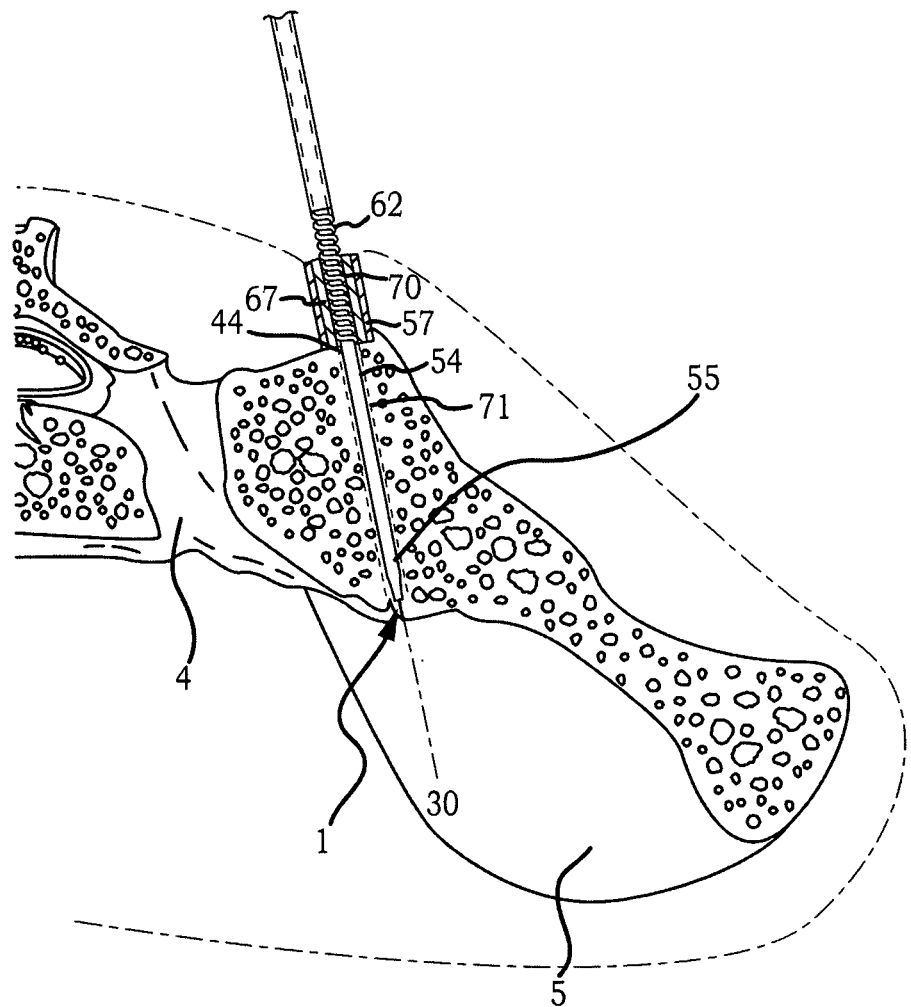
FIG. 22 is a cross section view through the sacroiliac joint which illustrates a method of implanting an embodiment of the fixation fusion implant the step including replacement of the tissue dialator with a first drill jig which receives a cannulated drill for production of a first bore hole substantially along the articular plane of the sacroiliac joint.

Now referring to FIG. 22, a cannulated drill bit (70) can be advanced over the probe body (54) and within a drill guide hole (68) of the first drill jig (67). The cannulated drill bit (70) under fluoroscopic guidance can be advanced into the interarticular region (44) between the articulating surfaces (16) of the sacroiliac joint (1) to produce a first bore (71) (shown in broken line) to a determined depth. As to certain embodiments of the method, an amount of articular cartilage or other tissues from between the articular surfaces (16) of the sacroiliac joint (1) can be removed sufficient to allow embodiments of the sacroiliac joint implant (6) to be implanted in replacement of the removed articular cartilage or tissue. Because the method removes the degenerative articular cartilage or tissue between the articular surfaces (16) of the sacroiliac joint (1), the articular surfaces (16) of the sacroiliac joint (1) can remain intact or substantially intact allowing the sacroiliac joint implant (6) to be non-transversely located between the articular surfaces (16) of the sacroiliac joint (1). Understandably, other instruments can be utilized separately or in combination with a cannulated drill bit (62) for the removal of articular cartilage or tissue between articular surfaces (16) such as: box chisels, burs, hole saws, curettes, lasers (such as $CO_2$, Neodymium/YAG (yttrium-aluminum-garnet), argon, and ruby), electrosurgical equipment employing electromagnetic energy (the cutting electrode can be a fine micro-needle, a lancet, a knife, a wire or band loop, a snare, an energized scalpel, or the like) where the energy transmitted can be either monopolar or bipolar and operate with high frequency currents, for example, in the range of about 300 kHz and about 1000 kHz whether as pure sinusoidal current waveform where the "crest factor" can be constant at about 1.4 for every sinus waveform, and a voltage peak of approximately 300 V to enable a "pure" cutting effect with the smallest possible coagulation effect or as amplitude modulated current waveforms where the crest factor varies between 1.5 and 8, with decreasing crest factors providing less of a coagulation effect. Electrosurgical waveforms may be set to promote two types of tissue effects, namely coagulation (temperature rises within cells, which then dehydrate and shrink) or cut (heating of cellular water occurs so rapidly that cells burst). The proportion of cells coagulated to those cut can be varied, resulting in a "blended" or "mixed" effect. Additionally, a fully rectified current, or a partially rectified current, or a fulguration current where a greater amount or lateral heat is produced can be employed to find the articular surfaces of the joint and aid in advancing a probe or guide wire into a position in between the articulating surfaces. These currents can effectively degrade the cartilage and allow advance into the joint without grossly penetrating much beyond the cartilage.

Figure 23:
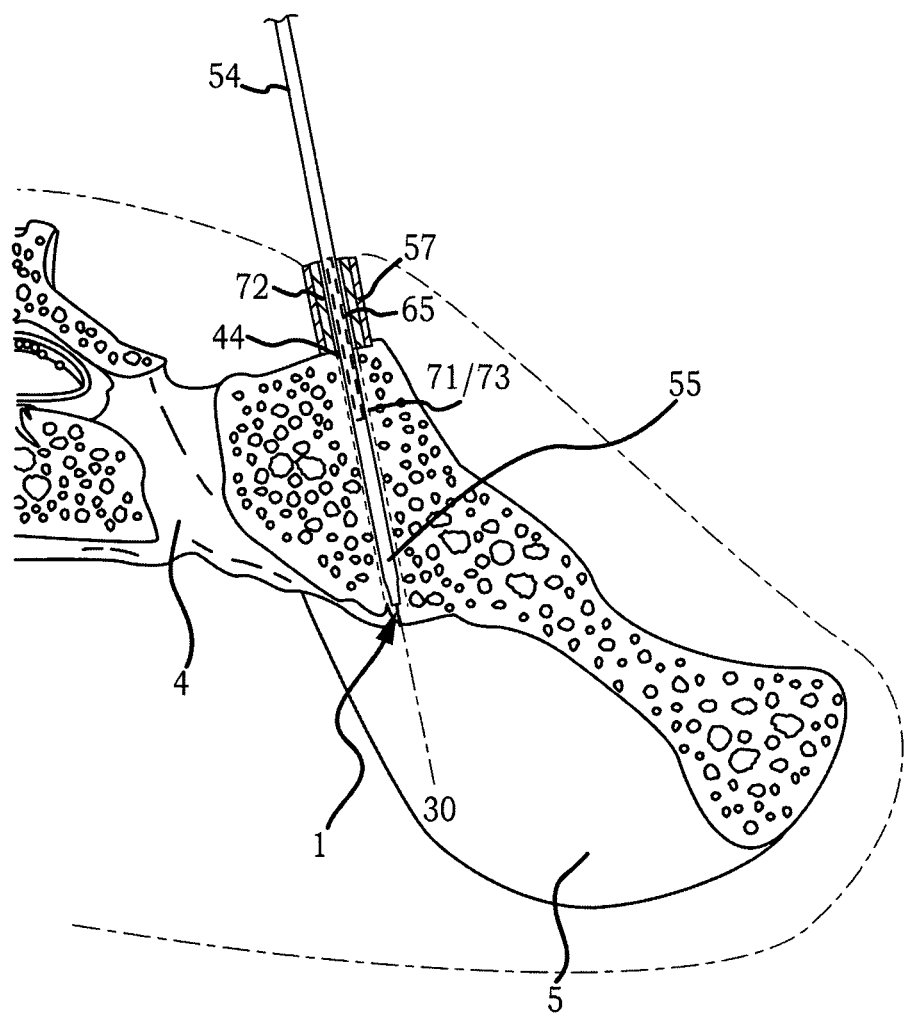
FIG. 23 is a cross section view through the sacroiliac joint which illustrates a method of implanting an embodiment of the sacroiliac implant the step including replacement of the first drill jig with a second drill jig which allows additional bore holes to be produced in relation to the first bore hole each substantially along the articular plane of the sacroiliac joint.

Now referring to FIG. 23, as to certain embodiments of the invention, the first drill jig (67) can be removed from within the cannula (57) and a second drill jig (72) can be advanced over the probe body (54) and received within the cannula (57); however, the invention is not limited to any particular number of drill jigs and as to certain embodiments of the method the first drill jig (67) can include all the required drill guide hole(s) (68)(or slots or other configurations of the drill guide) and as to other embodiments of the method a plurality of drill jigs can be utilized in serial order to provide all the drill guide holes (68). As to the particular embodiment of the invention shown by the Figures, the first drill jig (67) can provide one or more additional drill guide holes (68) which guide in relation to the first bore (71) a second or more cannulated drills (62) of the same or different configuration to be inserted within and advanced into the sacroiliac joint (1) to produce a second bore (73)(generally shown in broken line as 71/73) or a plurality of bores within the sacroiliac joint (1) spaced apart in predetermined pattern to allow removal of sufficient articular cartilage (16) or other tissue from the interarticular space of sacroiliac joint (1) for placement of embodiments of the sacroiliac joint implant (6) within the region defined by and between the paired articular surfaces (16) of the sacroiliac joint (1). As to certain methods of the invention, the first drill jig (67) or the second drill jig (72) or a plurality of drill jigs can be utilized in serial order to remove a portion of the sacroiliac joint (1) for generation of an implant receiving space (29). As these embodiments of the method, articular cartilage or other tissues and sufficient subchondral bone can be removed from between the articular surfaces (16) of the sacroiliac joint (1) sufficient to allow placement of certain embodiments of the sacroiliac joint implant (6) and one or more radial member receiving channels (74) can be cut into at least one of the articular surfaces (16) of said sacroiliac joint (1) sufficient to receive other embodiments of the sacroiliac implant (6). The one or more radial member receiving channels (74) can be cut a depth into the subchondral, cortical bone or cancellous bone of the sacrum (4) or ilium (5).

Now referring primarily to FIG. 24, in a subsequent step, the last in the serial presentation of drill jigs (67)(72) can be removed from within the cannula (57) and a broach jig (75) can be advanced over the probe body (54) to locate within the cannula (57). The broach jig (75) can include a broach guide hole (76) which receives a first broach end (77) of a cannulated broach (78) advanced over the probe body (54). The first broach end (77) can have a configuration which can be advanced into the sacroiliac joint (1). As to certain embodiments of the method, the first broach end (77) can be adapted to remove an amount of articular cartilage and other tissue from the betweent the articular surfaces (16) within the articular region (44) of the sacroiliac joint (1) for non-transverse placement of a sacroiliac joint implant (6) having an elongate body (7), or having an elongate body (7) and a first radial member (14), or an elongate body (7) having a first and second radial members (14)(15) between the articular surfaces (16) of the sacroiliac joint (1). As to other embodiments of the method, the cannulated broach (78) can remove a sufficient a portion of the sacroiliac joint (1) to generate an implant receiving space (29) to receive embodiments of the sacroiliac joint implant (6) having an elongate body (7), an elongate body (7) and at least one radial member (14) adapted for non-transverse placement between the articular surfaces (16) or at least one radial member (26) adapted to extend into the bone of the sacrum (4) or the ilium (5). As a non-limiting example, FIG. 24 shows a broach (78) configured to remove a portion of the sacroiliac joint (1) to produce a implant receiving space (29) to receive embodiments of the sacroiliac joint implant (6) having and elongate body (7) to which a first radial member (14) and a second radial member (15) extend along the longitudinal axis (8) of the elongate body (7) in substantially opposed relation adapted to locate between the articular surfaces (16) of the sacroiliac joint (1) and further having a third radial member (26) and a fourth radial member (27) which extend along the longitudinal axis (8) of the elongate member (7) in substantially opposed relation adapted to correspondingly extend correspondingly into the bone of the sacrum (4) and the ilium (5).

Now referring primarily to FIGS. 25 and 26A, 26B, and 26C, the implant receiving space (29) and the sacroiliac joint implant (6) can be configured having related dimension relations such that placement of the sacroiliac joint implant (6) within the implant receiving space (29) disposes the sacrum (4) and the ilium (5) in substantially immobilized relation and substantially avoids alteration of the positional relation of the sacrum (4) and the ilium (5) from the normal condition, or avoids driving together or driving apart the sacrum (4) from the ilium (5) outside of or substantially outside of the normal positional relation. An intention in selecting configurations of the sacroiliac joint implant (6) and the implant receiving space (29) being immobilization of the sacrum (4) in relation to the ilium (5) while maintaining the sacroiliac joint (1) in substantially normal or substantially normal positional relation, or returning the sacroiliac joint (1) to a substantially normal positional relation to correct a degenerative condition of the sacroiliac joint (1).

As a non-limiting example, configurations of an implant receiving space (29) allow embodiments of the sacroiliac joint implant (6) to be placed non-transversely between the caudal portion (86) of the articular surfaces (16) of the sacroiliac joint (1). While certain embodiments of the sacroiliac joint implant (6) may only provide an elongate body (7) which locates within a correspondingly configured implant receiving space (29) to engage at least a portion of the bone of the ilium (5); the invention is not so limited, and can further include at least a first radial member or a first and a second radial member at least a portion of the external surface of the first radial member (14) engaging a portion of the bone (73) of the sacrum (4) and the ilium (5). As to those embodiments of the sacroiliac joint implant (6) which have a third radial member (26) and a fourth radial member (27) the implant receiving space (29) an further include one more radial member receiving channels (74)) which correspondingly allow the third and fourth radial members (26)(27) to extend into the bone of the sacrum (4) or the ilium (5)(whether subchondral, cortical, cancellous, or the like), or impact of the sacroiliac joint implant (6) into the implant receiving space (29) without the radial member receiving channels (74) can forcibly urge the radial members (26)(27) into the bone of the sacrum (4) and the ilium (5). Mechanical fasteners (39)(such as treaded members) can be inserted through the bores (36) in the anti-migration element (33) and into the sacrum (4) and ilium (5) to fix location of the fixation fusion implant (6) within the implant receiving space (29).

Now referring to FIGS. 27 and 28A, 28B and 28C, as second a non-limiting example, configurations of an implant receiving space (29) allow embodiments of the sacroiliac joint implant (6) to be placed non-transversely between the cranial portion (86) of the articular surfaces (16) of the sacroiliac joint (1) by the similar procedures or steps as above described with the incision and generation of the passage to the superior articular portion of the sacroiliac joint (1).

Now referring to FIGS. 29 and 30, configurations of an implant receiving space (29) allow embodiments of the sacroiliac joint implant (6) to be placed non-transversely between the cranial portion (87) and caudal portion (86) of the articular surfaces (16) of the sacroiliac joint (1) by the similar procedures or steps as above described with the incision and generation of the passage to the inferior articular portion of the joint.

Now referring primarily to FIG. 31, which shows an embodiment of the sacroiliac joint implant (6) having a portion of the axial bore (9) adapted to fixedly mate with a portion of an alignment tool (79). The alignment tool (79) can have a fixed or adjustably fixed configuration which aligns a cannulated alignment guide (80) with one of the bores (36) through the sacroiliac joint implant (6). An insertion tool (81) can be slidingly engaged with the cannulated alignment guide (80). An elongate member (85) can be removably fixedly attached to the first insertion tool end (82) proximate the bore (36) in the sacroiliac joint implant (6). The second insertion tool end (83) can be forcibly advanced in the cannulated alignment guide (80) to advance the elongate member (81) to pass through the bore (36) to dispose the elongate member (81) in transverse relation to said articular surfaces (16) correspondingly engaged with sacroiliac joint implant (6). As a non-limiting example, the elongate member (81) can have a spiral thread (84) coupled to the external surface and by rotation of the second end (83) of the insertion tool (81) the elongate member (85) can be drawn through the bore (36) of the sacroiliac joint implant (1) in transverse relation to said articular surfaces (16) correspondingly engaged with sacroiliac joint implant (6). By further operation of the elongate member (85) the articular surfaces (16) of the sacroiliac joint (1) can be drawn against the external surfaces of the sacroiliac joint implant (6).

Now referring primarily to FIG. 32, embodiments of the invention can further comprise a coupling element (87) connected to the first end (11) of the sacroiliac joint implant (6). As a non-limiting example, the coupling element (87) can be disposed in fixed relation to the first end (11) of the sacroiliac joint implant (6) by threaded engagement of a fastener portion (88); however, the invention is not so limited and the fastener portion (88) can be connected to the first end (11) of the sacroiliac joint implant (6) by any method such as welding, spin welding, adhesive, or the like. The coupling element (87) can further provide a coupling portion (89) configured to join with a numerous and wide variety of cross sectional geometries of spanning members (90). As a non-limiting example, the coupling portion (89) can be configured as cylindrical cup (91) pivotally coupled to the fastener portion (88). A spiral thread can be coupled to the internal surface of the cylindrical cup (91) to rotationally receive a spirally threaded body (92). The side wall (93) of the cylindrical cup (91) can include a pass through element (94) in which part of a spanning member (90) can be received. The part of the spanning member (90) received within the pass through element (94) can be placed in fixed relation to the cylindrical cup (91) by rotational engagement of the spirally threaded body (92).

Now referring primarily to FIG. 33, as a further non-limiting example, each of a pair of sacroiliac joints (1) can receive an embodiment of the sacroiliac joint implants (6), above-described, each having a coupling element (87) coupled to the first end (11). Each of the coupling elements (87) can receive the opposed ends (95) of a spanning member (90). Additionally, the spanning member (90) in fixed relation to the sacroiliac joint implants (6) can be connected to a plurality of additional spanning members (96) which can as a non-limiting example be placed in positional relation to the vertebral column (97) to allow support of additional implants which can be anchored between vertebrae.

Now referring primarily to FIG. 34, as a further non-limiting example, a first coupling element (87) can be joined to the first end (11) of an embodiment of a sacroiliac joint implant (6) as above described and the fastener portion (88) of a second coupling element (87) can be disposed directly into the bone of the sacrum (4) or the ilium (5), or both. The opposed ends (95) of a spanning element (90) in the form of a flat plate can be can provide apertures (96) through which the fastener portion (88) of the coupling element (87) can pass. The corresponding parts of the external surface of the coupling portion (89) and the spanning member (90) can be engaged to fix the location of the spanning member (90) allowing for coupling of the lumbar spine to the stabilized pelvis by a plurality of fixation elements to further increase stability.

The method can further employ the use of intraoperative neurophysiological monitoring to reduce the risk to the patient of iatrogenic damage to the nervous system, particularly the peripheral nerves, or to provide functional guidance to the surgeon.

Example 1

An embodiment of the inventive sacroiliac joint implant having a configuration substantially as shown by FIGS. 3-6 and as above-described was inserted into a patient under direct visualization and with assisted lateral fluoroscopy. The procedure was performed for the purpose of assessing in an actual reduction to practice the ability of the inventive sacroiliac joint implant to be safely implanted between inferior or caudal portion the articular surfaces of the sacroiliac joint substantially as shown in FIG. 25 to confirm the that implantation of the sacroiliac joint implant into a implant receiving space configured substantially as above-described acts to immobilize the sacroiliac joint. The sacroiliac joint implant as above-described implanted into the inferior (caudal) portion of the sacroiliac joint proved to immediately immobilize the sacroiliac joint.

As can be easily understood from the foregoing, the basic concepts of the present invention may be embodied in a variety of ways. The invention involves numerous and varied embodiments of sacroiliac joint fusion system which includes sacroiliac joint implants and methods of implanting the sacroiliac joint implants including the best mode to provide fixation and fusion of the sacroiliac joint.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "an implant" should be understood to encompass disclosure of the act of "implanting"—whether explicitly discussed or not—and, conversely, were there effectively disclosure of the act of "implanting", such a disclosure should be understood to encompass disclosure of "an implant" and even a "means for implanting a member." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

For the purposes of the present invention, ranges may be expressed herein as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. Moreover, the term "about" means as to any numeric value a deviation about that numeric value of up to ten percent.

Moreover, for the purposes of the present invention, the term "a" or "an" entity refers to one or more of that entity; for example, "a member" or "an elongate member" refers to one or more member(s) or at least one member. As such, the terms "a" or "an", "one or more" and "at least one" can be used interchangeably herein.

Thus, the applicant(s) should be understood to claim at least: i) the sacroiliac joint implants as herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. A sacroiliac joint implant for non-transverse placement between articular surfaces of a sacroiliac joint to dispose a sacrum and an ilium in substantially immobilized relation, the implant comprising:

a distal end, a proximal end opposite the distal end, an axial bore extending distally from the proximal end, and a length extending between the distal end and the proximal end;

a first perpendicular flange extending the length of the implant and including a first planar top surface;

a second perpendicular flange opposite of and substantially parallel to the first perpendicular flange, the second perpendicular flange extending the length of the implant and including a second planar top surface;

a first connecting member coupled to and extending substantially perpendicularly between the first perpendicular flange and the second perpendicular flange, the first connecting member extending at least the length of the implant and comprising:

a distal edge that slopes from a distal most ti to a distal end of the first perpendicular flange; and at least one passage that extends transversely through the first connecting member between the distal end and the proximal end, the at least one passage dimensioned to allow an elongate member to be received within the at least one passage to anchor the implant to the articular surfaces, wherein the second perpendicular flange further includes an anti-migration element at a proximal end of the second perpendicular flange, the anti-migration element including a tapering of the proximal end of the second perpendicular flange in order to resist movement of the implant within the articular surfaces.

2. A sacroiliac joint implant for non-transverse placement between articular surfaces of a sacroiliac joint to dispose a sacrum and an ilium in substantially immobilized relation, the implant comprising:

a distal end, a proximal end opposite the distal end, an axial bore extending distally from the proximal end, and a length extending between the distal end and the proximal end;

a first perpendicular flange extending the length of the implant and including a first planar top surface;

a second perpendicular flange opposite of and substantially parallel to the first perpendicular flange, the second perpendicular flange extending the length of the implant and including a second planar top surface;

a first connecting member coupled to and extending substantially perpendicularly between the first perpendicular flange and the second perpendicular flange, the first connecting member extending at least the length of the implant and comprising:

a distal edge that slopes from a distal most tip to a distal end of the first perpendicular flange; and at least one passage that extends transversely through the first connecting member between the distal end and the proximal end, the at least one passage dimensioned to allow an elongate member to be received within the at least one passage to anchor the implant to the articular surfaces, wherein a proximal end of the first connecting member further includes an outward flaring portion that is configured to resist movement of the implant within the articular surfaces.

3. The sacroiliac joint implant as in claim 2, wherein the at least one passage includes a first passage that extends generally distally from the proximal end and extends through the outward flaring portion.

4. The sacroiliac joint implant as in claim 3, wherein the at least one passage includes a second passage that extends between respective openings on opposite sides of the first connecting member, the second passage being positioned distal of the outward flaring portion.

5. A sacroiliac joint implant for non-transverse placement between articular surfaces of a sacroiliac joint to dispose a sacrum and an ilium in substantially immobilized relation, the implant comprising:

a distal end, a proximal end opposite the distal end, an axial bore extending distally from the proximal end, and a length extending between the distal end and the proximal end;

a first perpendicular flange extending the length of the implant and including a first planar top surface;

a second perpendicular flange opposite of and substantially parallel to the first perpendicular flange, the second perpendicular flange extending the length of the implant and including a second planar top surface;

a first connecting member coupled to and extending substantially perpendicularly between the first perpendicular flange and the second perpendicular flange, the first connecting member extending at least the length of the implant and comprising:

a distal edge that slopes from a distal most tip to a distal end of the first perpendicular flange; and at least one passage that extends transversely through the first connecting member between the distal end and the proximal end, the at least one passage dimensioned to allow an elongate member to be received within the at least one passage to anchor the implant to the articular surfaces, wherein the at least one passage includes a passage length that is more than about one fourth of the length of the implant.

6. A sacroiliac joint implant for non-transverse placement between articular surfaces of a sacroiliac joint to dispose a sacrum and an ilium in substantially immobilized relation, the implant comprising:

a distal end, a proximal end opposite the distal end, an axial bore extending distally from the proximal end, and a length extending between the distal end and the proximal end;

a first perpendicular flange extending the length of the implant and including a first planar top surface;

a second perpendicular flange opposite of and substantially parallel to the first perpendicular flange, the second perpendicular flange extending the length of the implant and including a second planar top surface;

a first connecting member coupled to and extending substantially perpendicularly between the first perpendicular flange and the second perpendicular flange, the first connecting member extending at least the length of the implant and comprising:

a distal edge that slopes from a distal most tip to a distal end of the first perpendicular flange; and at least one passage that extends transversely through the first connecting member between the distal end and the proximal end, the at least one passage dimensioned to allow an elongate member to be received within the at least one passage to anchor the implant to the articular surfaces, wherein the at least one passage includes a passage length that is between about one fourth to about two thirds of the length of the implant.

7. A sacroiliac joint implant for non-transverse placement between articular surfaces of a sacroiliac joint to dispose a sacrum and an ilium in substantially immobilized relation, the implant comprising:

a distal end, a proximal end opposite the distal end, an axial bore extending distally from the proximal end, and a length extending between the distal end and the proximal end;

a first perpendicular flange extending the length of the implant and including a first planar top surface;

a second perpendicular flange opposite of and substantially parallel to the first perpendicular flange, the second perpendicular flange extending the length of the implant and including a second planar top surface;

a first connecting member coupled to and extending substantially perpendicularly between the first perpendicular flange and the second perpendicular flange, the first connecting member extending at least the length of the implant and comprising:

a distal edge that slopes from a distal most tip to a distal end of the first perpendicular flange; and at least one passage that extends transversely through the first connecting member between the distal end and the proximal end, the at least one passage dimensioned to allow an elongate member to be received within the at least one passage to anchor the implant to the articular surfaces, wherein the at least one passage includes a passage height that is more than about one fourth of a height of the first connecting member.

8. A sacroiliac joint implant for non-transverse placement between articular surfaces of a sacroiliac joint to dispose a sacrum and an ilium in substantially immobilized relation, the implant comprising:

a distal end, a proximal end opposite the distal end, an axial bore extending distally from the proximal end, and a length extending between the distal end and the proximal end;

a first perpendicular flange extending the length of the implant and including a first planar top surface;

a second perpendicular flange opposite of and substantially parallel to the first perpendicular flange, the second perpendicular flange extending the length of the implant and including a second planar top surface;

a first connecting member coupled to and extending substantially perpendicularly between the first perpendicular flange and the second perpendicular flange, the first connecting member extending at least the length of the implant and comprising:

a distal edge that slopes from a distal most tip to a distal end of the first perpendicular flange; and at least one passage that extends transversely through the first connecting member between the distal end and the proximal end, the at least one passage dimensioned to allow an elongate member to be received within the at least one passage to anchor the implant to the articular surfaces, wherein the at least one passage includes a passage height that is between about one fourth to about two thirds of a height of the first connecting member.

9. A sacroiliac joint implant for non-transverse placement between articular surfaces of a sacroiliac joint to dispose a sacrum and an ilium in substantially immobilized relation, the implant comprising:

a distal end, a proximal end opposite the distal end, an axial bore extending distally from the proximal end, and a length extending between the distal end and the proximal end;

a first perpendicular flange extending the length of the implant and including a first planar top surface;

a second perpendicular flange opposite of and substantially parallel to the first perpendicular flange, the second perpendicular flange extending the length of the implant and including a second planar top surface;

a first connecting member coupled to and extending substantially perpendicularly between the first perpendicular flange and the second perpendicular flange, the first connecting member extending at least the length of the implant and comprising:

a distal edge that slopes from a distal most tip to a distal end of the first perpendicular flange; and at least one passage that extends transversely through the first connecting member between the distal end and the proximal end, the at least one passage dimensioned to allow an elongate member to be received within the at least one passage to anchor the implant to the articular surfaces, wherein the at least one passage includes a passage length that is about one fourth to about two thirds of the length of the implant and the at least one passage includes a passage height that is about one fourth to about two thirds of a height of the first connecting member.

10. A sacroiliac joint implant for non-transverse placement between articular surfaces of a sacroiliac joint to dispose a sacrum and an ilium in substantially immobilized relation, the implant comprising:

a distal end, a proximal end opposite the distal end, an axial bore extending distally from the proximal end, and a length extending between the distal end and the proximal end;

a first perpendicular flange extending the length of the implant and including a first planar top surface;

a second perpendicular flange opposite of and substantially parallel to the first perpendicular flange, the second perpendicular flange extending the length of the implant and including a second planar top surface;

a third perpendicular flange that is opposite of and parallel to the first perpendicular flange, the third perpendicular flange extending the length of the implant, the second perpendicular flange being substantially centered between the first perpendicular flange and the third perpendicular flange;

a first connecting member coupled to and extending substantially perpendicularly between the first perpendicular flange and the second perpendicular flange, the first connecting member extending at least the length of the implant and comprising:

a distal edge that slopes from a distal most tip to a distal end of the first perpendicular flange; and at least one passage that extends transversely through the first connecting member between the distal end and the proximal end, the at least one passage dimensioned to allow an elongate member to be received within the at least one passage to anchor the implant to the articular surfaces, and a second connecting member coupled to and extending substantially perpendicularly between the second perpendicular flange and the third perpendicular flange, the second connecting member extending the length of the implant and comprising a second distal edge that slopes from the distal most tip to a distal end of the third perpendicular flange.

11. The sacroiliac joint implant as in claim 10, further comprising at least one second passage that extends transversely through the second connecting member between the distal end and a proximal end, the at least one second passage dimensioned to allow the elongate member to be received within the at least one second passage to anchor the implant to the articular surfaces.

12. The sacroiliac joint implant as in claim 11, wherein the at least one second passage communicates between respective openings on opposite sides of the second connecting member.

13. The sacroiliac joint implant as in claim 12, wherein the opposite sides of the second connecting member are substantially parallel along at least a portion of the length.

14. The sacroiliac joint implant as in any of claim 1-2, or 5-10, in which the implant is curved along the length of the implant.

15. A sacroiliac joint implant for non-transverse placement between articular surfaces of a sacroiliac joint to dispose a sacrum and an ilium in substantially immobilized relation, the implant comprising:
   a distal end, a proximal end opposite the distal end, an axial bore extending distally from the proximal end, and a length extending between the distal end and the proximal end;
   a first perpendicular flange extending the length of the implant and including a first planar top surface;
   a second perpendicular flange opposite of and substantially parallel to the first perpendicular flange, the second perpendicular flange extending the length of the implant and including a second planar top surface;
   a first connecting member coupled to and extending substantially perpendicularly between the first perpendicular flange and the second perpendicular flange, the first connecting member extending at least the length of the implant and comprising:
      a distal edge that slopes from a distal most tip to a distal end of the first perpendicular flange; and
   at least one passage that extends transversely through the first connecting member between the distal end and the proximal end, the at least one passage dimensioned to allow an elongate member to be received within the at least one passage to anchor the implant to the articular surfaces,
   wherein the implant is curved along the length of the implant and defines a radius along the length of the implant, a ratio of the radius to the length of the implant being between about one third to about one.

16. The sacroiliac joint implant as in any of claim 1-2, 5-10, or 15, in which the at least one passage extends transversely to the extension of the axial bore.

17. The sacroiliac joint implant as in any of claim 1-2, 5-10, or 15, in which the first planar top surface is an uninterrupted planar surface.

18. The sacroiliac joint implant as in any of claim 1-2, 5-10, or 15, in which the first connecting member is generally rectangular.

19. The sacroiliac joint implant as in any of claim 1-2, 5-10, or 15, in which the first and the second perpendicular flange include a tapered edge along the length of the implant.

20. The sacroiliac joint implant as in any of claim 1-2, 5-10, or 15, in which the first and the second perpendicular flange and the first connecting member define an I-beam shape.

21. The sacroiliac joint implant as in any of claim 1-2, 5-10, or 15, in which the distal edge extends distally beyond the length of the implant.

22. A sacroiliac joint implant for non-transverse placement between articular surfaces of a sacroiliac joint to dispose a sacrum and an ilium in substantially immobilized relation, the articular surfaces comprising a cranial portion and a caudal portion, the implant comprising:
   a distal end, a proximal end opposite the distal end, and a length extending between the distal end and the proximal end;
   a first arcuate edge extending the length of the implant;
   a second arcuate edge opposite the first arcuate edge and extending the length of the implant, wherein the first arcuate edge defines a first curvature along the length of the implant that matches a second curvature that is defined by the second arcuate edge along the length of the implant;
   a first planar connecting member extending a first distance between the first arcuate edge and the second arcuate edge and extending the length of the implant, the first planar connecting member including opposite planar surfaces disposed a second distance apart at the distal end and a third distance apart at the proximal end, the first arcuate edge extending the second distance between the opposite planar surfaces at the distal end, the first arcuate edge extending the third distance between the opposite planar surfaces at the proximal end;
   at least one passage extending transversely through the first planar connecting member, the at least one passage dimensioned to allow an elongate member to be received within the at least one passage to anchor the implant to the articular surfaces,
   wherein the first curvature defines a radial path along the length of the implant of between about 2 centimeters and about 6 centimeters.

23. A sacroiliac joint implant for non-transverse placement between articular surfaces of a sacroiliac joint to dispose a sacrum and an ilium in substantially immobilized relation, the articular surfaces comprising a cranial portion and a caudal portion, the implant comprising:
   a distal end, a proximal end opposite the distal end, and a length extending between the distal end and the proximal end;
   a first arcuate edge extending the length of the implant;
   a second arcuate edge opposite the first arcuate edge and extending the length of the implant, wherein the first arcuate edge defines a first curvature along the length of the implant that matches a second curvature that is defined by the second arcuate edge along the length of the implant, wherein the first curvature defines a radius along the length of the implant, a ratio of the radius to the length of the implant being between about one third to about one;
   a first planar connecting member extending a first distance between the first arcuate edge and the second arcuate edge and extending the length of the implant, the first planar connecting member including opposite planar surfaces disposed a second distance apart at the distal end and a third distance apart at the proximal end, the first arcuate edge extending the second distance between the opposite planar surfaces at the distal end, the first arcuate edge extending the third distance between the opposite planar surfaces at the proximal end;
   at least one passage extending transversely through the first planar connecting member, the at least one passage dimensioned to allow an elongate member to be received within the at least one passage to anchor the implant to the articular surfaces.

24. A sacroiliac joint implant for non-transverse placement between articular surfaces of a sacroiliac joint to dispose a sacrum and an ilium in substantially immobilized relation, the articular surfaces comprising a cranial portion and a caudal portion, the implant comprising:
   a distal end, a proximal end opposite the distal end, and a length extending between the distal end and the proximal end;
   a first arcuate edge extending the length of the implant;

a second arcuate edge opposite the first arcuate edge and extending the length of the implant;

a first planar connecting member extending a first distance between the first arcuate edge and the second arcuate edge and extending the length of the implant, the first planar connecting member including opposite planar surfaces disposed a second distance apart at the distal end and a third distance apart at the proximal end, the first arcuate edge extending the second distance between the opposite planar surfaces at the distal end, the first arcuate edge extending the third distance between the opposite planar surfaces at the proximal end;

at least one passage extending transversely through the first planar connecting member, the at least one passage dimensioned to allow an elongate member to be received within the at least one passage to anchor the implant to the articular surfaces;

a third arcuate edge extending the length of the implant;

a fourth arcuate edge opposite the third arcuate edge and extending the length of the implant; and a second planar connecting member extending a sixth distance between the third arcuate edge and the fourth arcuate edge and extending the length of the implant, the second planar connecting member including opposite planar surfaces disposed a seventh distance apart, the first arcuate edge and the second arcuate edge extending the sixth distance between the opposite planar surfaces of the planar connecting member, the second planar connecting member coupled to the first planar connecting member and being in substantially orthogonal relation to the first planar connecting member.

25. The sacroiliac joint implant as in claim 24, wherein the first distance is greater than the sixth distance.

26. The sacroiliac joint implant as in claim 24, wherein the first distance is at least double the sixth distance.

27. The sacroiliac joint implant as in claim 24, wherein the first arcuate edge defines a first curvature along the length of the implant that matches a second curvature that is defined by the second arcuate edge along the length of the implant.

28. The sacroiliac joint implant as in any of claim 22-23 or 24, in which the first curvature and the second curvature are consistent along the length of the implant.

29. The sacroiliac joint implant as in any of claim 22-23 or 24, in which the first distance is greater than the second distance.

30. The sacroiliac joint implant as in any of claim 22-23 or 24, in which the second distance and the third distance are substantially equal.

31. The sacroiliac joint implant as in any of claim 22-23 or 24, in which the third distance is greater than the second distance.

32. The sacroiliac joint implant as in any of claim 22-23 or 24, in which the second arcuate edge extends a fourth distance between the opposite planar surfaces at the distal end and extends a fifth distance between the opposite planar surfaces at the proximal end.

33. The sacroiliac joint implant as in claim 32, wherein the second distance is substantially equal to the fourth distance, the third distance is substantially equal to the fifth distance, and the third and the fifth distances are greater than the second and the fourth distances.

34. The sacroiliac joint implant as in claim 32, wherein the second and the third distances are greater than the fourth and the fifth distances such that the first planar connecting member defines a wedge-shape that tapers between the first arcuate edge and the second arcuate edge.

35. The sacroiliac joint implant as in any of claims 1-2, 5-10, 15, 22-23, or 24, in which the at least one passage comprises a pair of openings, each of the pair of openings including a closed perimeter and being positioned on opposite sides of the implant.

36. A system for treating a patient body having a sacroiliac joint, a spine, and a pelvis by delivery of an implant non-transversely between articular surfaces of the sacroiliac joint to dispose a sacrum and an ilium in substantially immobilized relation, the system comprising:
   a) the sacroiliac joint implant as in any of claims 16-2, 5-10, 15, 22-23, or 24; and
   b) a first coupling element connected to the proximal end of the sacroiliac joint implant, the first coupling element comprising a first coupling portion configured to join with an at least one spanning member;
   wherein the first coupling portion is configured to fix a location of the at least one spanning member allowing for coupling of either: i) the spine to the pelvis such that the sacroiliac joint implant is operably coupled with at least one spine fixation element via the at least one spanning member; ii) the sacroiliac joint implant to a second sacroiliac joint implant such that the sacroiliac joint implant is operably coupled with the second sacroiliac joint implant via the at least one spanning member; or iii) the sacroiliac joint implant to a second, coupling element disposed into either of the sacrum or ilium such that the sacroiliac joint implant is operably coupled with the second coupling element via the at least one spanning member.

37. A system for treating patient body having a sacroiliac joint, a spine, and a pelvis by delivery of an implant non-transversely between articular surfaces of the sacroiliac joint to dispose a sacrum and an ilium in substantially immobilized relation, the system comprising:
   a) the sacroiliac joint implant as in any of claims 16-2, 5-10, 15, 22-23, or 24; and
   b) an alignment tool comprising an alignment guide and a distal portion configured to fixedly mate with the proximal end of the sacroiliac joint implant, wherein the alignment tool comprises a fixed or adjustably fixed configuration such that the alignment guide is configured to align the elongate member to, pass through the at least one passage.

* * * * *

UNITED STATES PATENT AND TRADEMARK OFFICE
CERTIFICATE OF CORRECTION

PATENT NO. : 8,979,928 B2  
APPLICATION NO. : 12/998712  
DATED : March 17, 2015  
INVENTOR(S) : Edward Jeffrey Donner Page 1 of 1

It is certified that error appears in the above-identified patent and that said Letters Patent is hereby corrected as shown below:

IN THE CLAIMS:

- In claim 1, column 23, line 16, delete "ti" and replace with --tip--.
- In claim 14, column 27, line 8, delete "claim" and replace with --claims--.
- In claim 16, column 27, line 42, delete "claim" and replace with --claims--.
- In claim 17, column 27, line 45, delete "claim" and replace with --claims--.
- In claim 18, column 27, line 48, delete "claim" and replace with --claims--.
- In claim 19, column 27, line 51, delete "claim" and replace with --claims--.
- In claim 20, column 27, line 54, delete "claim" and replace with --claims--.
- In claim 21, column 27, line 57, delete "claim" and replace with --claims--.
- In claim 28, column 29, line 40, delete "claim" and replace with --claims--.
- In claim 29, column 29, line 43, delete "claim" and replace with --claims--.
- In claim 30, column 29, line 46, delete "claim" and replace with --claims--.
- In claim 31, column 29, line 49, delete "claim" and replace with --claims--.
- In claim 32, column 29, line 52, delete "claim" and replace with --claims--.
- In claim 37, column 30, line 53, delete the "," after "to.".
- In claim 36, column 30, line 21, delete "16-2," and replace with --1-2,--.
- In claim 37, column 30, line 41, after "treating" insert --a--.
- In claim 37, column 30, line 46, delete "16-2," and replace with --1-2,--.

Signed and Sealed this  
Eleventh Day of August, 2015

Michelle K. Lee  
*Director of the United States Patent and Trademark Office*